US012559548B2

(12) United States Patent
Cashman et al.

(10) Patent No.: US 12,559,548 B2
(45) Date of Patent: Feb. 24, 2026

(54) ANTIBODIES TO MISFOLDED TDP-43 AND METHODS OF USE

(71) Applicants: THE UNIVERSITY OF BRITISH COLUMBIA, Vancouver (CA); PROMIS NEUROSCIENCES INC., Toronto (CA)

(72) Inventors: Neil R. Cashman, Vancouver (CA); Johanne Kaplan, Sherborn, MA (US)

(73) Assignees: The University of British Columbia, Vancouver (CA); ProMIS Neurosciences Inc., Toronto (CA)

( * ) Notice: Subject to any disclaimer, the term of this patent is extended or adjusted under 35 U.S.C. 154(b) by 1116 days.

(21) Appl. No.: 17/413,881

(22) PCT Filed: Dec. 16, 2019

(86) PCT No.: PCT/CA2019/051823
§ 371 (c)(1),
(2) Date: Jun. 14, 2021

(87) PCT Pub. No.: WO2020/118458
PCT Pub. Date: Jun. 18, 2020

(65) Prior Publication Data
US 2022/0056118 A1 Feb. 24, 2022

Related U.S. Application Data

(60) Provisional application No. 62/923,789, filed on Oct. 21, 2019, provisional application No. 62/779,904, filed on Dec. 14, 2018.

(51) Int. Cl.
| | |
|---|---|
| *C07K 16/18* | (2006.01) |
| *C07K 7/06* | (2006.01) |
| *G01N 33/68* | (2006.01) |

(52) U.S. Cl.
CPC .............. *C07K 16/18* (2013.01); *C07K 7/06* (2013.01); *G01N 33/68* (2013.01); *C07K 2317/24* (2013.01); *C07K 2317/34* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 9,587,014 | B2 * | 3/2017 | Nitsch .................... | A61K 49/16 |
| 9,994,634 | B2 | 6/2018 | Lewis et al. | |
| 2017/0298124 | A1 | 10/2017 | Chen | |

FOREIGN PATENT DOCUMENTS

| | | |
|---|---|---|
| WO | 2013/061163 A2 | 5/2013 |
| WO | 2018/226590 A1 | 3/2020 |

OTHER PUBLICATIONS

Kwong LK et al. Novel monoclonal antibodies to normal and pathologically altered human TDP-43 proteins. Acta Neuropathol Commun. Mar. 31, 2014; 2:33.
Mompean M. et al. The TDP-43 N-terminal domain structure at high resolution. FEBS J. Apr. 2016; 283(7):1242-60.
Wang A. et al. A single N-terminal phosphomimic disrupts TDP-43 polymerization, phase separation, and RNA spicing. EMBO J. Mar. 1, 2018; 37(5).
Romano V. et al. The structural integrity of TDP-43 N-terminus is required for efficient aggregate entrapment and consequent loss of protein function. Prion. 2015; 9(1): 1-9.
Pokrishevsky, Edward. Induction of wild-type SOD1 misfoldeing, aggregation and its cell-to-cell propagation. Thesis submitted Mar. 2017.
Cashman N. et al. Targeting of misfolded, pathogenic TDP-43 with rationally designed antibodies. Alzheimer's Demen. 2020;16(Suppl. 9).
Cashman N. et al. Generation of Antibodies Selective for Misfolded Disease-Associated TDP-43. American Academy of Neurology Abstract Website. Apr. 14, 2020; 94 (Suppl. 15).
Pokrishevsky E. et al. TDP-43 or FUS-induced misfolded human wild-type SOD1 can propagate intercellularly in a prion-like fasion. Scientific Reports. Mar. 1, 2016.
Pokrishevsky E. et al. Tryptophan residues in TDP-43 and SOD1 mediate the cross-seeding and toxicity of SOD1. Jul. 28, 2020. bioRxiv preprint doi: https://doi.org/10.1101/2020.07.27.224188.
Kuo PH et al. The Crystal Structure of TDP-43 RRM1-DNA Complex Reveals the Specific Recognition for UG- and TG-Rich Nucleic Acids. Nucleic Acids Res., 2014, vol. 42, 4712.
Hie F. et al. Solution structure of RRM domain in TAR DNA-binding protein-43. Worldwide Protein Data Bank, May 28, 2020. DOI: 10.2210/pdb1wf0/pdb.
Mompean M. et al. The TDP-43 N-Terminal Domain Structure at High Resolution. FEBS J., 2016, 283, 1242.
Arai T. et al. TDP-43 is a component of ubiquitin-positive tau-negative inclusions in frontotemporal lobar degeneration and amyotrophic lateral sclerosis. Biochem. Biophys. Res. Commun., 2006, 351, 602-611.
Sephton CF et al. TDP-43 Is a Developmentally Regulated Protein Essential for Early Embryonic Development. Biol. Chem. 2010, vol. 285, No. 9, 6826-6834.
Abel O. et al. ALSoD: a user-friendly online bioinformatics tool for amyotrophic lateral sclerosis genetics. Hum Mutat 2012;33:1345-51.
Hamley IW. PEG-Peptide Conjugates. American Chemical Society. 2014; 15, 1543-1559.

(Continued)

*Primary Examiner* — Zachariah Lucas
*Assistant Examiner* — Sarah A Alsomairy
(74) *Attorney, Agent, or Firm* — Smart & Biggar LP; Carmela De Luca; Alissa Hyppolite

(57) ABSTRACT

The disclosure pertains to antibodies that specifically bind W68 in the context of DAGWGNL (SEQ ID NO: 1). Also provided are isolated peptides, isolated nucleic acids, immunogens, compositions, kits, and methods of using said reganents to detect misfolded TDP-43.

20 Claims, 14 Drawing Sheets

Specification includes a Sequence Listing.

(56)                References Cited

OTHER PUBLICATIONS

Afroz T. et al. Functional and dynamic polymerization of the ALS-linked protein TDP-43 antagonizes its pathologic aggregation. Nat Comm (2017) 8:45.

Porta S. et al. Patient-derived frontotemporal lobar degeneration brain extracts induce formation and spreading of TDP-43 pathology in vivo. Nature Comm (2018) 9:4220.

Brettschneider J. et al. Sequential distribution of pTDP-43 pathology in behavioral variant frontotemporal dementia (bvFTD). Acta Neuropathol (2014) 127: 423.

Feiler MS et al. TDP-43 is intercellularly transmitted across axon terminals. J Cell Biol (2015) 211: 897.

Braak H. et al. Amyotrophic lateral sclerosis—a model of corticofugal axonal spread. Nat Rev Neurol. Dec. 2013, 9(12): 708-714.

Wang W. et al. The Inhibition of TDP-43 Mitochondrial Localization Blocks its Neuronal Toxicity. Nat Med Aug. 2016; 22(8):869-878.

Nonaka T. et al. Prion-like Properties of Pathological TDP-43 Aggregates from Diseased Brains. Cell Reports 4, 124-134, Jul. 11, 2013.

De Boer EMJ et al. TDP-43 proteinopathies: a new wave of neurodegenerative diseases. J Neurol Neurosurg Psychiatry 2021; 92:86-95.

Chou CC et al. TDP-43 pathology disrupts nuclear pore complexes and nucleocytoplasmic transport in ALS/FTD. Nat Neurosci. Feb. 2018; 21(2): 228-239.

Munch C. et al. Prion-like propagation of mutant superoxide dismutase-1 misfolding in neuronal cells. PNAS Mar. 1, 2011, vol. 108, No. 9, pp. 3548-3553.

Grad Li et al. Intermolecular transmission of superoxide dismutase 1 misfolding in living cells. PNAS, Sep. 27, 2011, vol. 108, No. 39, pp. 16398-16403.

Tamaki Y. et al. Elimination of TDP-43 inclusions linked to amyotrophic lateral sclerosis by a misfolding-specific Intrabody with a dual proteolytic signals. Scientific Reports, 2018, 8:6030.

Sonobe Y. et al. Translation of dipeptide repeat proteins from the C9ORF72 expanded repeat is associated with cellular stress. Neurobiol Dis. Aug. 2018, 116:155-165.

Pokrishevsy E. et al. Aberrant Localization of FUS and TDP43 is Associated with Misfolding of SOD1 in Amyotrophic Lateral Sclerosis. PLoS One, Apr. 2012, vol. 7, Issue 4.

Neumann M. et al. Ubiquitinated TDP-43 in Frontotemporal Lobar Degeneration adn Amyotrophic Lateral Sclerosis. Science, vol. 314, Oct. 6, 2006, pp. 130-133.

Endo R. et al. TDP-43 and DISC1 Co-Aggregation Disrupts Dendritic Local Translation and Mental Function in FTLD. Biological Psychiatry. Mar. 2008. DOI: 10.1016/j.biopsych.2018.03.008.

Roberts, M.J. et al. Chemistry for peptide and protein PEGylation. Advanced Drug Delivery Reviews, 2012, vol. 64, pp. 116-127.

Francois-Moutal, Liberty et al. Structural Insights Into TDP-43 and Effects of Post-translational Modifications. Frontiers in Molecular Neuroscience, vol. 12, No. 17, Dec. 2019.

Pozzi, Silvia et al. Virus-mediated delivery of antibody targeting TAR DNA-binding protein-43 mitigates associated neuropathology. The Journal of Clinical Investigation. Vol. 129, No. 4, 2019.

Press-release ( ProMIS Neurosciences), Apr. 30, 2020.

Press-release ( ProMIS Neurosciences), Oct. 30, 2020.

Presentation at J.P. Morgan 39th Annual Healthcare Conference 2021, Jan. 2021.

* cited by examiner

A

B

C

D

A

B

C

D

E

A    G3BP1 staining – Stress granule marker

B    3F11 antibody staining

ANTIBODIES TO MISFOLDED TDP-43 AND METHODS OF USE

RELATED APPLICATIONS

This is a Patent Cooperation Treaty Application which claims the benefit of 35 U.S.C. § 119 based on the priority of U.S. Provisional Patent Application Nos. 62/779,904, filed Dec. 14, 2018; and 62/923,789, filed Oct. 21, 2019; each of these applications being incorporated herein in their entirety by reference.

INCORPORATION OF SEQUENCE LISTING

A computer readable form of the Sequence Listing "pp 54811PC00PC00_ST25" (58,887 bytes), submitted via EFS-WEB and created on Dec. 12, 2019, is herein incorporated by reference.

FIELD

The present disclosure relates to TDP-43 antibodies and more specifically to antibodies for detecting misfolded TDP-43 and methods of detecting misfolded TDP-43.

BACKGROUND

Transactive response (TAR) element DNA binding protein of 43 kDa (TDP-43), is a 414 amino acid protein, and is comprised of an N-terminal ubiquitin like domain (NTD, residues 1-80), two RNA recognition motifs (RRMs) composed of residues 106-177 (RRM1), and residues 192-259 (RRM2), and a C-terminal domain (CTD, residues 274-414). The NTD flanks a domain that directs nuclear localization (NLS motifs in residues 82-98, NLS1 K82RK84 and K95VKR98). RRM2 includes a nuclear export signal (NES) from residue 239 to 250.

TDP-43 is predominantly a nuclear protein that plays a central role in RNA metabolism. TDP-43 has become a focal point of research in the amyotrophic lateral sclerosis (ALS) and frontotemporal dementia (FTD) disease spectrum, since pathogenic inclusions within affected neurons can contain post-translationally modified TDP-43. The CTD of TDP-43 is particularly relevant to disease, as it is where nearly all familial ALS/FTD-associated mutations are found in TDP-43.

Other mutations include D169G which is located in RRM1 between beta strands 4 and 5, A90V which is a mutation in the NLS region, and the mutations K263E and N267S which are in the linker between RRM2 and the C-terminal domain.

RRM1 and RRM2 have been structurally determined by NMR. For example, RRM1 is available in the Protein Data Bank (PDB), a database of atomic resolution three dimensional structural data, as PDB entry 4IUF, while RRM2 is available as PDB entry 1WF0, and the NTD is available as PDB entry 5MRG, 2N4P and 6B1G.

The structure of 4IUF is reported in Kuo et al. [1]. The structure of 1WF0 is reported in He et al [2]. The structure of 2N4P is reported in Mompean et al. [3].

TDP-43 was found to be hyperphosphorylated, ubiquitinated, and fragmented in neuronal inclusions of patients with both sporadic and familial forms of ALS and FTD [4].

Functional TDP-43 can exist as nuclear oligomers that are distinct from cytoplasmic aggregates formed upon cellular stress. Functional TDP-43 oligomerization is required for its RNA-splicing function. NTD-driven TDP-43 oligomerization in the nucleus can inhibit cytoplasmic mislocalization and the formation of pathologic aggregation [9].

Physiological TDP-43 oligomerization is mediated by its N-terminal domain, which can adopt dynamic, solenoid-like structures, revealed by a 2.1 A crystal structure in combination nuclear magnetic resonance spectroscopy and electron microscopy [9].

Aggregates (inclusion bodies) of TDP-43 have now been found in nearly all (approx. 97%) cases of ALS and roughly half (approx. 45%) of the cases of FTD. TDP-43 is one of the main components of the cytoplasmic inclusions found in the motor neurons of ALS patients.

Precursers of TDP-43 inclusions may have concentration far below that of functional TDP-43. The low concentration of misfolded TDP-43 makes this target elusive.

Intracerebral injections of brain derived pathological TDP-43 FTLD-TDP seeds in transgenic mice expressing cytoplasmic human TDP-43 and non-transgenic mice, and has led to the induction of de novo TDP-43 pathology which spread through the brain in a time dependent manner [10].

Antibodies that bind TDP-43 have been described.

WO2012174666 titled METHODS FOR THE PROGNOSTIC AND/OR DIAGNOSTIC OF NEURODEGENERATIVE DISEASE, METHODS TO IDENTIFY CANDIDATE COMPOUNDS AND COMPOUNDS FOR TREATING NEURODEGENERATIVE DISEASE discloses methods for diagnosing neurodegenerative diseases such as ALS and FTD through assessing the interaction between TDP-43 and NF-κB p65 using an anti-TDP-43 antibody.

WO2016086320 titled TDP-43-BINDING POLYPEPTIDES USEFUL FOR THE TREATMENT OF NEURODEGENERATIVE DISEASES disclose antibodies that bind to the RRM1 domain of TDP-43 to disrupt its interaction with NF-κB for the treatment of ALS and FTD.

Antibodies that preferentially bind misfolded TDP-43 over natively folded TDP-43 are desirable.

SUMMARY

The inventors have identified antibodies that preferentially bind TDP-43 aggregates and not natively folded nuclear or cytosolic TPD-43. The inventors have identified an epitope that is differentially accessible in misfolded TDP-43, and have raised antibodies which recognize said epitope in misfolded TDP-43 aggregates. As demonstrated herein, the epitope is available for binding in misfolded TDP-43 (solvent accessible) but is unavailable in natively folded non-disease associated TDP-43. In particular, the inventors have determined that W68 is an important residue in conferring antibody specificity for misfolded TDP-43 aggregates. Such antibodies, recognize aggregated TDP-43 that is not typically associated with stress granules and can inhibit cell to cell transmission of pathogenic TDP-43.

Accordingly, an aspect includes an isolated peptide comprising all or part of DAGWGNL (SEQ ID NO: 1), wherein the part is at least 5 amino acids and comprises GWG.

In another embodiment, the part is at least 6 contiguous amino acids of DAGWGNL (SEQ ID NO: 1).

In an embodiment, the peptide is up to 21 residues, optionally where W68 is preferably in the middle third of the peptide.

Another aspect includes an immunogen comprising a peptide, the peptide comprising all or part of DAGWGNL (SEQ ID NO: 1), wherein the part is at least 5 amino acids, optionally at least 6 amino acids of DAGWGNL (SEQ ID NO: 1).

In an embodiment, the immunogen comprises multiple peptides, each peptide comprising at least 5 amino acids, optionally at least 6 amino acids of DAGWGNL (SEQ ID NO: 1), wherein the multiple peptides are synthesized as a multiple antigenic peptide (MAP).

In another embodiment, the peptide is coupled to a carrier protein or immunogenicity enhancing component.

In another embodiment the carrier protein is bovine serum albumin (BSA) or the immunogenicity-enhancing component is keyhole limpet haemocyanin (KLH).

In an embodiment, wherein the immunogen is used to produce an antibody that selectively binds misfolded TDP-43 and/or specifically binds at least W68 in the context of DAGWGNL (SEQ ID NO: 1). In an embodiment, the antibody preferentially binds misfolded TDP-43.

A further aspect includes an antibody that binds TDP-43 and preferentially binds misfolded TDP-43 compared to native TDP-43.

In an embodiment, the antibody specifically binds at least W68 in the context of DAGWGNL (SEQ ID NO:1).

In an embodiment, the antibody is raised or screened using a peptide or immunogen described herein.

In an embodiment, the antibody is a monoclonal antibody.

In an embodiment, the antibody is a humanized antibody.

In an embodiment, the antibody is a single chain antibody.

In an embodiment, the antibody is a binding fragment selected from Fab, Fab', F(ab')$_2$, scFv, dsFv, ds-scFv, dimers, nanobodies, minibodies, diabodies, and multimers thereof.

In an embodiment, the antibody is affinity purified.

A further aspect comprises an immunoconjugate comprising an antibody described herein and a detectable label.

A further aspect comprises an isolated nucleic acid encoding amino acid residues of a peptide, immunogen, or antibody described herein, as well as vectors comprising the nucleic acid, for example, for delivering and/or expressing a peptide, immunogen or antibody described herein.

A further aspect comprises a cell recombinantly expressing a peptide, immunogen or an antibody described herein.

In an embodiment, the cell when expressing the antibody is a hybridoma.

A further aspect includes a composition comprising an isolated peptide, immunogen, antibody, immunoconjugate, isolated nucleic acid, or a cell described herein.

In an embodiment, the composition when comprising a peptide or immunogen, further comprises an adjuvant.

In an embodiment, the adjuvant is incomplete Freunds adjuvant, aluminum phosphate, aluminum hydroxide aluminum hydroxide alum, monophosphoryl lipid A and/or QS21.

Also provided is a kit comprising an isolated peptide, immunogen, antibody, immunoconjugate, isolated nucleic acid, cell, and/or composition, and a compartment for housing said reagents.

In another embodiment, the kit further comprises instructions for use in an ELISA for a method described herein.

A further aspect includes a method for making an antibody, the method comprising administering or immunizing a non-human subject with an isolated peptide (e.g. at least 5 amino acids, optionally at least 6 amino acids of DAGWGNL (SEQ ID NO: 1), immunogen, or composition described herein.

In an embodiment, the method further comprises isolating an antibody that specifically binds W68 in the context of DAGWGNL (SEQ ID NO: 1).

In an embodiment, the method further comprises forming antibody-producing hybridomas.

Another aspect includes an antibody produced by a method described herein.

A further aspect includes a method of determining if a sample contains misfolded TDP-43, the method comprising contacting the sample with an antibody described herein under conditions permissive for forming an antibody: misfolded TDP-43 complex, and detecting the presence of any complex wherein the presence of detectable complex is indicative that the sample may contain misfolded TDP-43 polypeptide.

In an embodiment, the sample is a biological sample obtained from a subject.

In an embodiment, the sample comprises blood, serum, plasma and/or solid tissue.

In an embodiment, the sample is a human sample.

In an embodiment, the subject has or is suspected of having amyotrophic lateral sclerosis (ALS) or frontotemporal dementia (FTD).

Further provided is a method of treating a subject, the method comprising administering to a subject in need thereof an effective amount of the antibody, immunoconjugate, the nucleic acid or the composition described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

DETAILED DESCRIPTION OF THE DISCLOSURE

Figure 1:
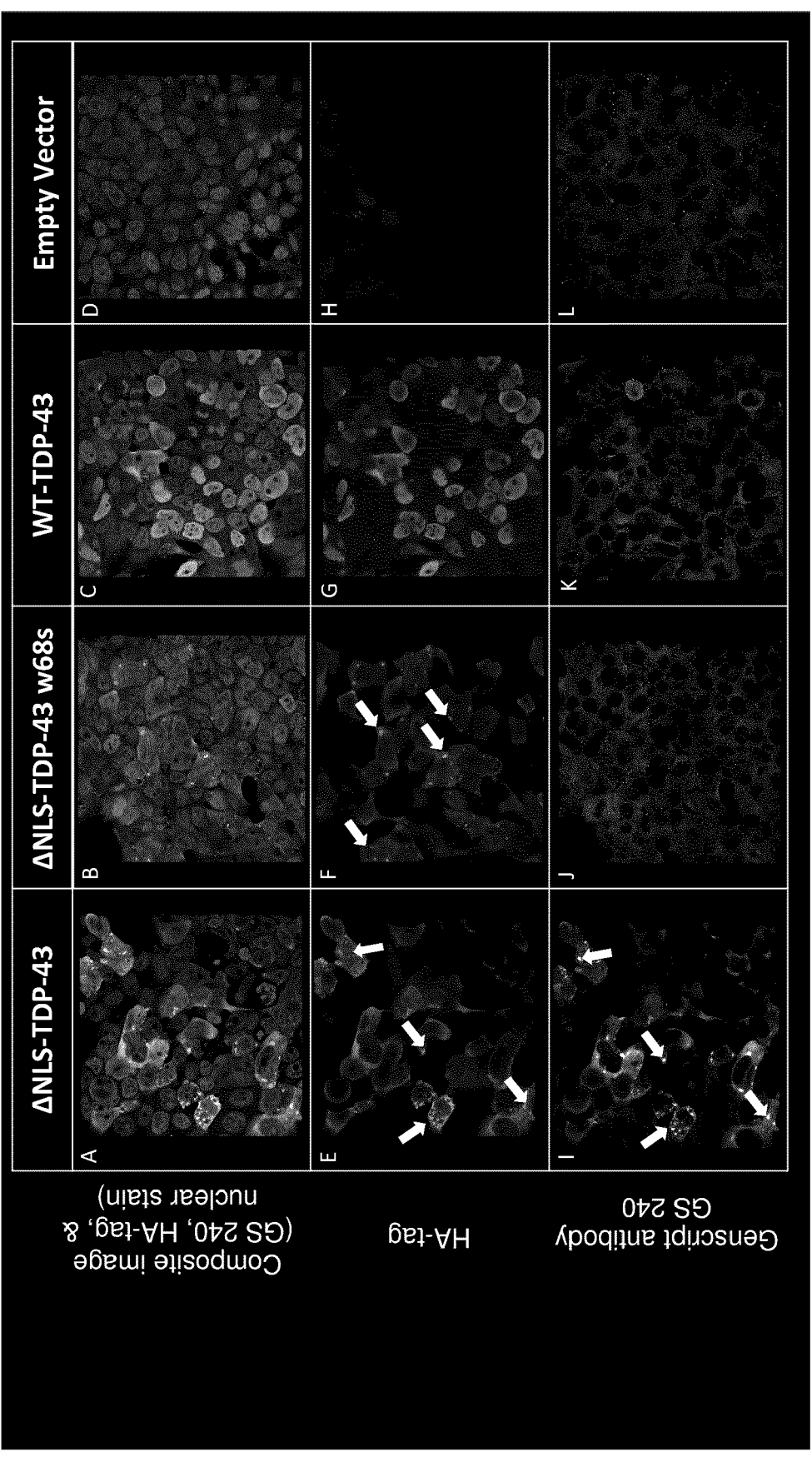
FIGS. 1A-1L show HEK-293 cells transfected with TDP-43 construct with a triple missense tandem mutation in the nuclear localization signal, wildtype TDP-43, or empty vector. The TDP-43 in the cells was detected using DAGWGNL (SEQ ID NO: 1)-peptide affinity-purified rabbit polyclonal anti-TDP-43 antibody (GS240) raised against an immunogen comprising DAGWGNL (SEQ ID NO: 1) peptide described herein, or anti-HA tag antibody reacting with the TDP-43-HA fusion construct.
Figure 2:
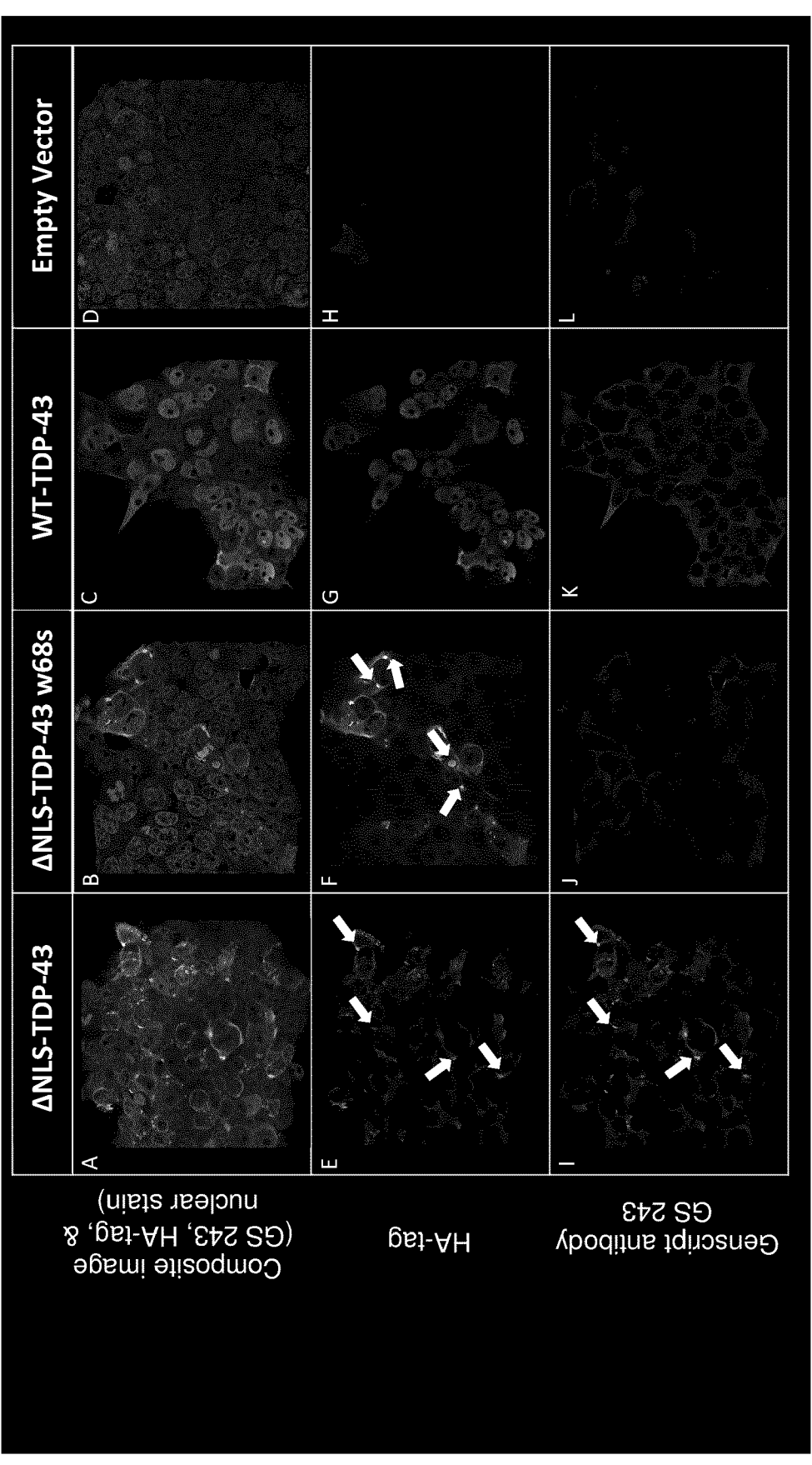
FIGS. 2A-2L show HEK-293 cells transfected with TDP-43-HA construct with a triple missense tandem mutation in the nuclear localization signal, wildtype TDP-43-HA, or empty vector. TDP-43 was detected in the cells using purified polyclonal anti-TDP-43 antibody (GS243) raised against an immunogen comprising DAGWGNL (SEQ ID NO: 1) peptide described herein, or anti-HA tag antibody.
Figure 3:
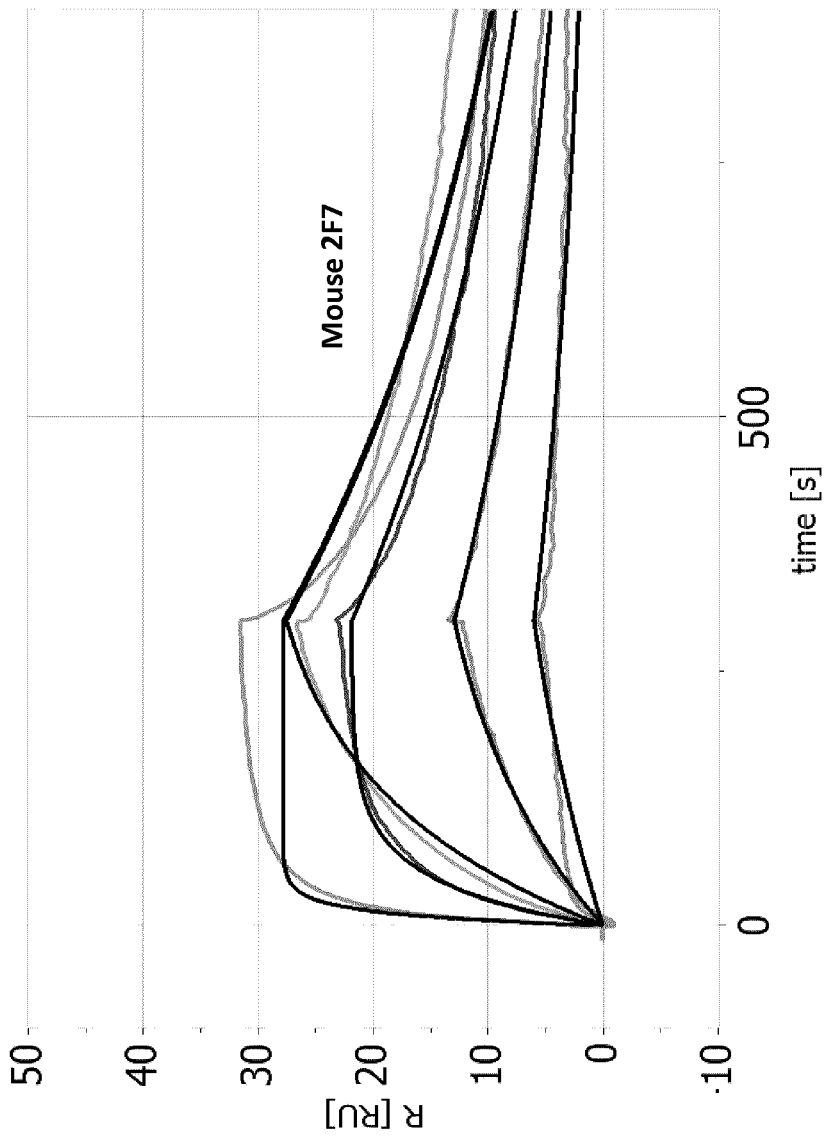
FIGS. 3A-3E are graphs showing binding kinetics of mouse (3A and 3B) and rabbit (3C, 3D and 3E) monoclonal antibodies.
Figure 3:
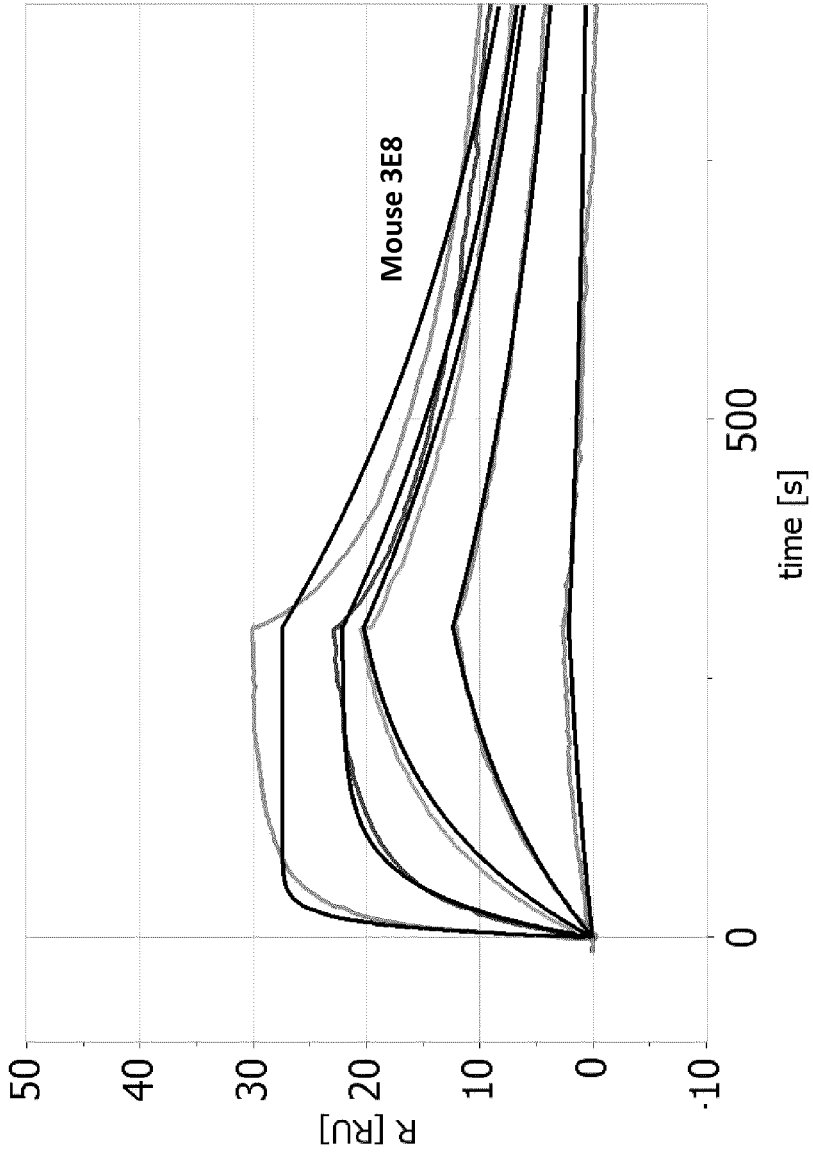
Figure 3:
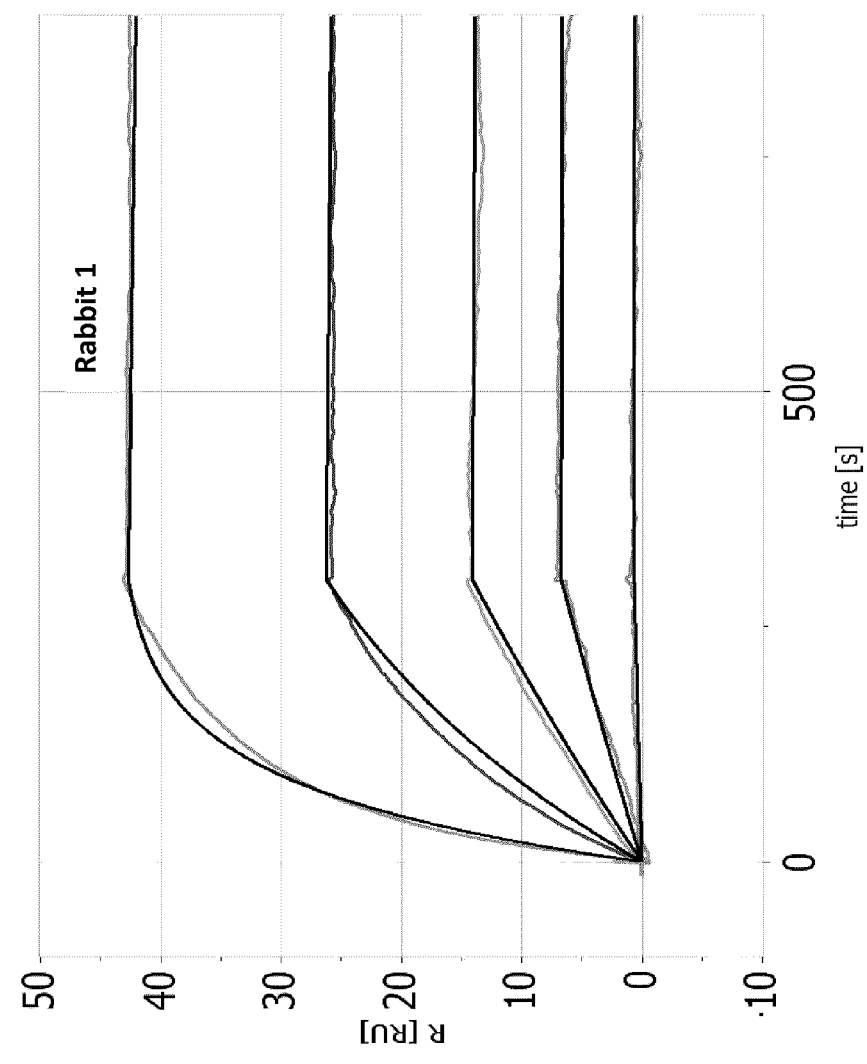
Figure 3:
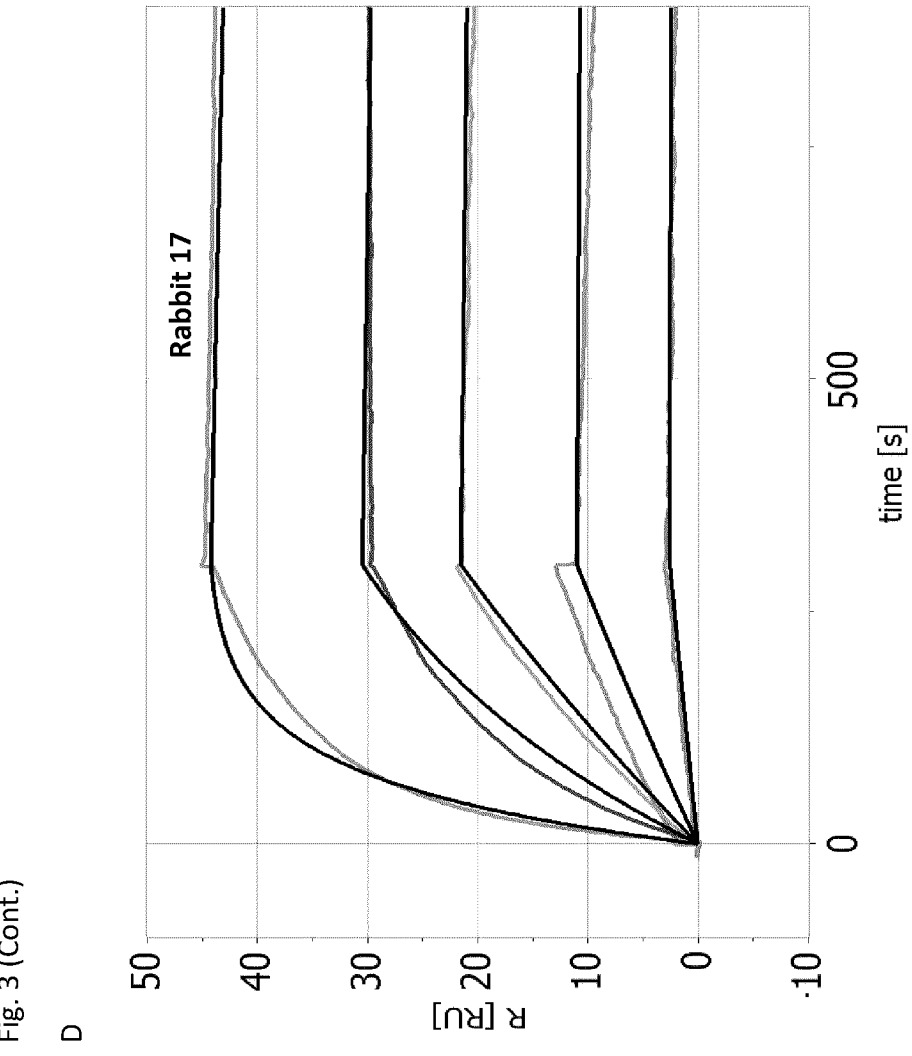
Figure 3:
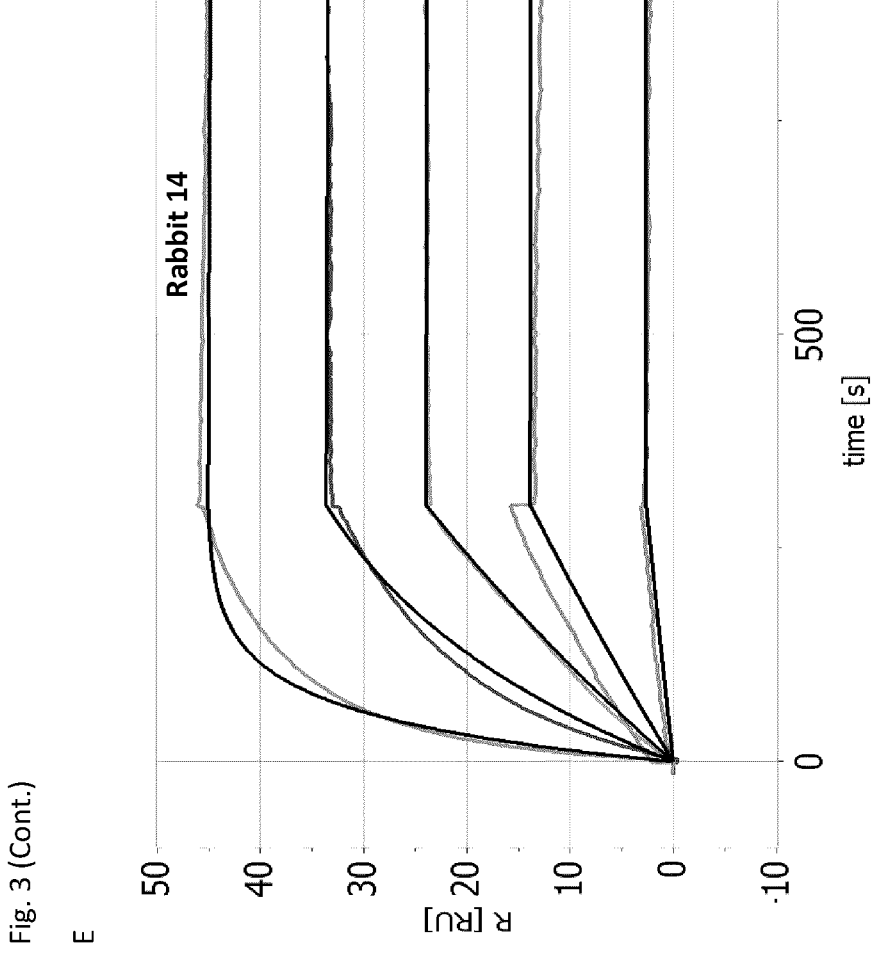

As described in the Examples, the inventors have identified an epitope that is specifically accessible in misfolded TDP-43. They have raised antibodies that specifically bind said epitope. Further they have determined the importance of W68 in the context of DAGWGNL (SEQ ID NO: 1). Antibodies raised to this peptide sequence have been shown to preferentially bind misfolded TDP-43 compared to native TDP-43.

I. Definitions

As used herein, the term "TDP-43" (transactivation response element (TAR) DNA-binding protein 43) alternately referred to as "TDP43", or "TDP" unless otherwise qualified, as used herein means all forms of TDP-43 including wildtype TDP-43, native TDP-43, as well as misfolded forms including mutant forms and analogs thereof from all species, particularly human TDP-43 (i.e. hTDP-43). Human TDP-43 is a protein of typically 414 amino acid residues and the amino acid sequence (e.g. Uniprot Accession number Q13148) and the nucleotide sequence (e.g. Accession number HGNC: 11571) have been previously characterized.

"Wild type" as used herein refers to the primary amino acid sequence of non-mutant or naturally occurring protein.

"Native" as used herein refers to the normal three dimensional structure of a specific protein or part thereof). Native TDP-43 is optionally referred to as "natively folded" TDP-43 "normally folded" TPD-43 and/or "healthy" TDP-43. Accordingly the term "native TDP-43", or "natively folded TDP-43", herein refers to TDP-43 as natively folded after nascent translation and/or multimers including but not limited to dimeric TDP-43 and trimeric TDP-43, as folded in non-disease states (e.g. healthy cells) with a molecular structure that comprises a non-covalently associated, individual TDP-43 peptide which shows native structure under in x-ray crystallography or as reconstructed from nuclear magnetic resonance spectra. Native TDP-43 forms multimers through its NTD and TDP-43 when natively folded is typically nuclear. Misfolded aggregates of TDP-43 can be and are typically cytoplasmic.

"Misfolded" as used herein refers to the secondary and tertiary structure of a polypeptide or part thereof, and indicates that the polypeptide has adopted a conformation that is not normal for that polypeptide in its properly functioning state. Although misfolding can be caused by mutations in a protein, such as amino acid deletion, substitution, or addition, wild-type sequence protein can also be misfolded in disease, and expose disease-specific epitopes for instance, as a result of microenvironmental conditions and/or amino acid modification such as nitration, oxidation, carbonylation or other modification. Other post-translational modifications include aberrant ubiquitination, phosphorylation, acetylation, sumoylation, and cleavage into C-terminal fragments. Misfolded TDP43 can be aggregated and/or cytosolic. In the context of TDP-43, native TDP-43 forms multimers through its NTD. Misfolded multimers (e.g. disease-associated oligomers) typically oligomerize through other regions of the protein, for example its LCD and/or RRM1 domains. Accordingly, "misfolded TDP-43 polypeptide", or "misfolded TDP-43" when referring to the polypeptide herein includes TDP-43 polypeptide that is oligomerized through its LCD and/or RRM1 domains, non-native dimers and trimers, as well as larger aggregates (e.g. 5 or greater subunits), which is cytosolic and/or is aggregated. Misfolded TDP-43 is prone to the formation of aggregates which results in a loss of protein function, toxicity, possession of amyloid-like features (e.g. congo red staining) and propagation of pathogenic aggregates.

The term "mutant TDP-43" refers to forms of TDP-43, and particularly endogenous forms of TDP-43 that occur as a result of genetic mutation that result for instance in amino acid substitution, such as those substitutions characteristic for instance of FTD or familial ALS including for example the mutations described in the bioinformatics tool described in [6].

The term "DAGWGNL (SEQ ID NO: 1)" means the amino acid sequence: aspartic acid, alanine, glycine, tryptophan, glycine, asparagine, and leucine as shown in SEQ ID NO: 1. Similarly GWG refers to the amino acid sequences identified by the 1-letter amino acid code. Depending on the context, the reference of the amino acid sequence can refer to a sequence in TDP-43 or an isolated peptide. The sequence DAGWGNL (SEQ ID NO: 1) corresponds to residues 65-71 in the amino acid primary sequence of TDP-43.

An "epitope" as used herein means a region of a protein that is recognized by a B cell or T-cell receptor, or an antibody or a binding fragment thereof. The epitope is optionally represented herein by a linear amino acid sequence or the region of the protein recognized by the antibody. An epitope can comprise one or more antigenic determinants. For example an antibody generated against an isolated peptide corresponding to a misfolded epitope recognizes part or all of said epitope sequence. As shown in the Examples, antibodies can require Trp68 for binding. An immunogen comprising at least 5, optionally at least 6 residues of SEQ ID NO: 1 can be used to raise antibodies that preferentially bind misfolded TDP-43 e.g. bind to SEQ ID: NO: 1 or W68 in the context of DAGWGNL (SEQ NO: 1).

Reference to "DAGWGNL (SEQ NO: 1) or a related epitope" means SEQ ID NO: 1 or a part thereof, either in the linear peptide or the region on TDP-43 that is bound by an antibody raised for example by an immunogen comprising a TDP-43 peptide sequence such as DAGWG (SEQ ID NO: 2), DAGWGN (SEQ ID NO: 3), AGWGN (SEQ ID NO: 4), AGWGNL (SEQ ID NO: 5) and GWGNL (SEQ ID NO: 6).

The term "analog" as used herein includes parts, extensions, substitutions, variants, modifications or chemical equivalents and derivatives thereof of the amino acid and nucleotide sequences of the present invention that perform substantially the same function as the peptide, protein or nucleic acid molecules of described herein in substantially the same way. Analogs of the peptides also include additions and deletions to the TDP-43 peptides. Analogs of nucleic acids include degenerate nucleotide substitutions that encode an isolated peptide of the invention. In addition, analog peptides and analog nucleotide sequences include derivatives thereof.

The term "amino acid" includes all of the naturally occurring amino acids as well as modified L-amino acids as well as D-amino acids. The atoms of the amino acid can for example include different isotopes. For example, the amino acids can comprise deuterium substituted for hydrogen, nitrogen-15 substituted for nitrogen-14, and carbon-13 substituted for carbon-12 and other similar changes.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-group size for one another. Examples of conservative amino acid substitution include:

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "antibody" as used herein is intended to include monoclonal antibodies, polyclonal antibodies, single chain, humanized and other chimeric antibodies, or fully human antibodies, as well as binding fragments thereof. Also included are vectorized antibodies or intrabodies. The antibody may be from recombinant sources and/or produced in transgenic animals. Also included are human antibodies that can be produced through using biochemical techniques or isolated from a library. Humanized or chimeric antibody may include sequences from one or more than one isotype or class.

The phrase "isolated antibody" refers to antibody produced in vivo or in vitro that has been removed from the source that produced the antibody, for example, an animal, hybridoma or other cell line (such as recombinant cells that produce antibody). The isolated antibody is optionally "purified", which means at least: 80%, 85%, 90%, 95%, 98% or 99% purity.

The term "binding fragment" as used herein to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, dimers, nanobodies, minibodies, diabodies, and multimers thereof. Fragments can be obtained via chemical or enzymatic treatment of an intact or complete antibody or antibody chain. Fragments can also be obtained by recombinant means (vide infra). For example, F(ab')2 fragments can be generated by treating the antibody with pepsin. The resulting F (ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques. When an antibody is said to bind to an epitope within specified residues, such as DAGWGNL (SEQ ID NO: 1), what is meant is that the antibody selectively or specifically binds to a polypeptide containing the specified residues or a part thereof for example at least 1 residue or at least 2 residues in the context of the specified residues such as (SEQ ID NO:1). Such an antibody does not necessarily contact every residue of DAGWGNL (SEQ ID NO:1), and every single amino acid substitution or deletion within said epitope does not necessarily significantly affect or equally affect binding affinity.

The term "complementarity determining region" or "CDR" as used herein refers to particular hypervariable regions of antibodies that are commonly presumed to contribute to epitope binding. Computational methods for identifying CDR sequences include Kabat, Chothia, and IMGT. The CDRs listed in the present disclosure are identified using IMGT Blast. A person skilled in the art having regard to the sequences comprised herein would also be able to identify CDR sequences based on Kabat and Chothia etc.

The term "detectable label" as used herein refers to moieties such as peptide sequences, fluorescent proteins that can be appended or introduced into a peptide, antibody or other compound described herein and which is capable of producing, either directly or indirectly, a detectable signal. For example, the label may be radio-opaque, positron-emitting radionuclide (for example for use in PET imaging), or a radioisotope, such as $^3$H, $^{13}$N, $^{14}$C, $^{18}$F, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. The detectable label may be also detectable indirectly for example using secondary antibody.

The term "epitope selectively presented or accessible in misfolded TDP-43" as used herein refers to an epitope that is selectively presented or antibody-accessible on misfolded TDP-43 as present for example in ALS or FTD (e.g. disease associated misfolded TDP-43) whether in monomeric, dimeric or aggregated forms, but not on the molecular surface of the native, correctly folded, homodimeric form of TDP-43. As shown herein, W68 is selectively presented or accessible in misfolded TDP-43.

The term "greater affinity" as used herein refers to a degree of antibody binding where an antibody X binds to target Y more strongly (Kon) and/or with a smaller dissociation constant ($k_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as KA equal to $1/k_D$ where $k_D$ is equal to $k_{on}/k_{off}$. The $k_{on}$ and $k_{off}$ values can be measured using surface plasmon resonance (measurable for example using a Biacore system).

Also as used herein, the term "immunogenic" refers to substances which elicit the production of antibodies, activate T-cells and other reactive immune cells directed against an antigenic portion of the immunogen.

An "immunogen" as used herein means a substance which provokes an immune response and/or causes production of an antibody. In addition to immunogenic compounds, conjugates and fusions described herein, including for example the isolated compounds conjugated to KLH, peptide mimetics which elicit cross-reactive antibodies to the epitopes identified, e.g. DAGWGNL and/or related epitopes such as DAGWG (SEQ NO: 2), DAGWGN (SEQ NO: 3), AGWGN (SEQ NO: 4), AGWGNL (SEQ NO: 5) and GWGNL (SEQ NO: 6) can be employed. To serve as a useful immunogen, the TDP-43 peptide desirably incorporates a minimum of about 5, 6, or 7 TDP-43 residues and a maximum of about 15, 17, 19, 20 or 21 TDP-43 amino acids, and optionally incorporates an immunogenicity enhancing agent such as KLH, optionally via a linker or scaffold as used in for example a multi-antigenic peptide (MAP).

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

"Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41 (% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5x sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

As used herein "specifically binds" in reference to an antibody means that the antibody recognizes its target antigen and binds its target with greater affinity than it does to a structurally different antigen and/or to an antigen with modified or mutated sequence. For example a multivalent antibody binds its target with $K_D$ of at least 1e-6, at least 1e-7, at least 1e-8, at least 1e-9 or at least 1e-10. Affinities greater than at least 1e-8 are preferred. An antigen binding fragment such as Fab fragment comprising one variable domain, may find its target with a 10 fold or 100 fold less affinity than a multivalent interaction with a non-fragmented antibody.

The term "selective" or "preferential" as used herein with respect to an antibody that selectively/preferentially binds a form of TDP-43 (e.g. native, or misfolded protein) means that the binding protein binds the form with at least 3 fold, or at least 5 fold, at least 10 fold, at least 20 fold, at least 100 fold, at least 250 fold, or at least 500 fold or more greater affinity. Accordingly an antibody that is more selective for a particular conformation (e.g. misfolded protein) preferentially binds the particular form of TDP-43 with at least 3 fold, or at least 5 fold, at least 10 fold, at least 20 fold, at least 100 fold, at least 250 fold, or at least 500 fold or more greater affinity compared to another form.

The term "an antibody that binds TDP-43 sequence DAGWGNL (SEQ ID NO: 1) in misfolded TDP-43" as used herein, means, an antibody, such as a binding fragment etc, that specifically or preferentially binds said sequence or any part of said sequence and not an unrelated sequence, in the context of misfolded TDP-43, relative to native TDP-43.

The term "linker" as used herein means a chemical moiety that can be covalently linked to the peptide comprising DAGWG (SEQ NO: 2), DAGWGN (SEQ NO: 3), AGWGN (SEQ NO: 4), AGWGNL (SEQ NO: 5) and GWGNL (SEQ NO: 6) or all of SEQ ID NO:1 epitope peptide. The linker can comprise glycine residues and/or PEG moieties as well as one or more functionalizable moieties such as a cysteine residue. The linker can be linked via the functionalizable moieties to a carrier protein or an immunogen enhancing component such as keyhole limpet hemocyanin (KLH). The linker can be for example 1 to 9 amino acids and can be the functionalizable moiety alone.

The term "functionalizable moiety" as used herein refers to a chemical entity with a "functional group" which as used herein refers to a group of atoms or a single atom that will react with another group of atoms or a single atom (so called "complementary functional group") to form a chemical interaction between the two groups or atoms. In the case of cysteine, the functional group can be —SH which can be reacted to form a disulfide bond. The reaction with another group of atoms can be covalent or a strong non-covalent bond, for example as in the case of biotin-streptavidin bonds, which can have Kd~1e-14. A strong non-covalent bond as used herein means an interaction with a Kd of at least 1e-9, at least 1e-10, at least 1e-11, at least 1e-12, at least 1e-13 or at least 1e-14.

Proteins and/or other agents may be functionalized (e.g. coupled/conjugated) to the peptide, either to aid in immunogenicity, or to act as a probe in in vitro studies. For this purpose, any functionalizable moiety capable of reacting (e.g. making a covalent or non-covalent but strong bond) may be used. In one specific embodiment, the functionalizable moiety is a cysteine residue which is reacted to form a disulfide bond with an unpaired cysteine on a protein of interest, which can be, for example, an immunogenicity enhancing component such as keyhole limpet hemocyanin (KLH), or a carrier protein such as Bovine serum albumin (BSA) used for in vitro immunoblots or immunohistochemical assays.

The term "animal" or "subject" as used herein includes all members of the animal kingdom including mammals, optionally including or excluding humans.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment, for example in a subject identified as carrying a mutation associated with familial forms, such as the familial form of ALS. A subject with a TDP-43 proteinopathy such as ALS can be treated to delay or slow disease progression. Subjects can be treated with a compound, antibody (including vectorized antibody or intrabody), immunogen, immunoconjugate, or composition described herein to prevent progression.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a", "an" and "the"

include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Peptides Comprising all or Part of DAGWGNL (SEQ ID NO:1) and Immunogens Related Thereto The present disclosure identifies an epitope on misfolded TDP-43 and antibodies raised using a peptide corresponding thereto preferentially recognize misfolded TDP-43. As shown in the Examples, the epitope and particularly W68, is not accessible or less accessible in natively folded TDP-43. The inventors have raised antibodies using an immunogen comprising TDP-43 peptide DAGWGNL (SEQ ID NO: 1) which corresponds to amino acid residues 65-71 on TDP-43. As shown below, antibodies were raised using said immunogen that do not appreciably react with TDP-43 mutated for this residue.

Accordingly an aspect includes an isolated peptide comprising all or part of DAGWGNL, wherein the part is at least 5 amino acids and comprises GWG.

In an embodiment, the part is at least 6 contiguous amino acids of SEQ ID NO: 1.

The peptide can comprise additional TDP-43 continuous sequence, for example up to 11 amino acids, up to 13 amino acids, up to 15 amino acids, up to 17 or 19 or up to 21 amino acids. Preferably the sequence is centered or nearly centred on W68. For example if the peptide is 21 amino acids long, W68 may be residue 8, 9, 10, 11 or 12. In one embodiment, the peptide is EGILHAPDAGWGNLVYVVNYP (SEQ ID NO: 7) or a part thereof minimally comprising GWG.

In an embodiment, the peptide comprises or is a continuous sequence from the N-terminal ubiquitin like domain of TDP-43, corresponding to residues 1-80 of TDP-43.

The isolated peptide can also comprise non-TDP-43 sequence for example a linker comprising for example 1-9 glycine and/or PEG moieties and/or a Cys residue N terminal and/or C terminal to the TDP-43 continuous sequences.

Peptides may be prepared by chemical synthesis using techniques well known in the chemistry of proteins such as solid phase synthesis or synthesis in homogenous solution.

The epitope W68 in the context of DAGWGNL (SEQ ID NO: 1), as described herein may be a potential target in misfolded propagating strains of TDP-43, and antibodies that recognize the epitope may for example be useful in detecting such propagating strains.

Another aspect includes an immunogen comprising a peptide comprising at least 5 residues, optionally at least 6 residues of DAGWGNL (SEQ ID NO: 1) optionally DAGWG (SEQ NO: 2), DAGWGN (SEQ NO: 3), AGWGN (SEQ NO: 4), AGWGNL (SEQ NO: 5) and GWGNL (SEQ NO: 6). In an embodiment, the peptide of the immunogen comprises DAGWGNL. The immunogen can also comprise a peptide with additional TDP-43 or non-TDP-43 residues as described herein. In an embodiment, the peptide comprised in the immunogen comprises or is a continuous sequence from the N-terminal ubiquitin like domain of TDP-43, corresponding to residues 1-80 of TDP-43.

As described in the Examples, an immunogen can be prepared by chemically synthesizing a peptide such as DAGWGNL (SEQ ID NO: 1), DAGWG (SEQ NO: 2), DAGWGN (SEQ NO: 3), AGWGN (SEQ NO: 4), AGWGNL (SEQ NO: 5) or GWGNL (SEQ NO: 6), optionally with a C-terminus or N-terminus cysteine residue (e.g. cDAGWGNL (SEQ ID NO: 8) or DAGWGNLc (SEQ ID NO: 9)), using techniques well known in the chemistry of proteins such as solid phase synthesis or synthesis in homogenous solution. The peptide can be N-terminally acetylated or C-terminally amidated. The peptide can be conjugated to an immunogenicity enhancing agent, for example through a C terminal or N-terminal cysteine residue or other functionalizable moiety or otherwise modified to increase immunogenicity.

In an embodiment, the immunogen comprises multiple peptides, each peptide comprising all or part of DAGWGNL (SEQ ID NO: 1), the part comprising at least at least 5, optionally at least 6 residues of DAGWGNL (SEQ ID NO: 1), wherein the multiple peptides are synthesized as a multiple antigenic peptide (MAP). A MAP is a branched poly-lysine dendrimer. Multiple epitope peptides are attached for example to one or both of the amino terminus and side-chain of the lysines.

In an embodiment, the peptide is coupled to a carrier protein or immunogenicity enhancing component. The immunogenicity enhancing component can be coupled to the compound either directly, such as through an amide bond, disulfide bond, or indirectly through a linker.

The immunogen with an immunogenicity enhancing component can be produced by conjugating the peptide and a linker comprising a functionalizable moiety such as cysteine to an immunogenicity enhancing component such as keyhole limpet hemocyanin (KLH) or a carrier such bovine serum albumin (BSA) using for example the method described in Lateef et al 2007, herein incorporated by reference. In an embodiment, the method described in Example 1 is used.

A further aspect includes an antibody that preferentially binds misfolded TDP-43, for example cytosolic and/or aggregated misfolded TDP-43 produced by an immunogen described herein.

In an embodiment, the antibody produced specifically binds at least W68 in the context of DAGWGNL (SEQ ID NO: 1).

III. Antibodies, Immunoconjugates, Cells and Nucleic Acids

The isolated peptide comprising DAGWGNL (SEQ ID NO: 1) or a related epitope and immunogens described above can be used to raise antibodies that preferentially bind misfolded TDP-43 compared to native TDP-43.

Accordingly, an aspect includes an antibody that binds misfolded TDP-43 compared to native TDP-43.

In an embodiment, the antibody binds TDP-43 sequence DAGWGNL (SEQ ID NO: 1), a related epitope thereof or a part thereof, wherein the antibody preferentially binds misfolded TDP-43 compared to native TDP-43.

In an embodiment, the antibody specifically binds W68 in the context of DAGWGNL (SEQ ID NO: 1), a related epitope thereof or a part thereof, wherein the antibody preferentially binds misfolded TDP-43 compared to native TDP-43.

In an embodiment, the antibody does not specifically bind and/or is not selective for native TDP-43. Selective binding can be measured using an ELISA or surface plasmon resonance measurement, as described herein.

In an embodiment, the antibody is isolated.

A further aspect is an antibody which specifically or selectively binds an epitope present on TDP-43, wherein the epitope comprises or consists of at least one amino acid residue predominantly involved in binding to the antibody, wherein at least one amino acid is W68 in the context of DAGWGNL (SEQ ID NO:1). In an embodiment, the epitope comprises or consists of at least three consecutive amino acid residues predominantly involved in binding to the antibody, wherein the at least three consecutive amino acids are GWG embedded within DAGWGNL (SEQ ID NO:1).

To produce monoclonal antibodies, antibody producing cells (lymphocytes) can be harvested from a subject immunized with an immunogen described herein, and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the desired epitopes and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 41:544-546 (1989); Huse et al., Science 246:1275-1281 (1989); and McCafferty et al., Nature 348: 552-554 (1990)).

The humanization of antibodies from non-human species (for example from mouse or rabbit) has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (e.g. Scotgen Limited, 2 Holly Road, Twickenham, Middlesex, Great Britain).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224:487-499, 1992). To maintain the affinity of the antibody, it is often necessary to replace certain framework residues by site directed mutagenesis or other recombinant techniques and may be aided by computer modeling of the antigen binding site (Co et al. J Immunol, 152:2968-2976, 1994).

Humanized forms of antibodies are optionally obtained by resurfacing (Pedersen et al. J Mol Biol, 235:959-973, 1994). In this approach only the surface residues of a rodent antibody are humanized.

Human antibodies specific to a particular antigen may be identified by a phage display strategy (Jespers et al. Bio/Technology, 12:899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced where members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region (JH) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Humanized or human antibodies are selected from any class of immunoglobulins including: IgM, IgG, IgD, IgA or IgE; and any isotype, including: IgG1, IgG2, IgG3 and IgG4. The humanized or human antibody may include sequences from one or more than one isotype or class. Further, these antibodies are typically produced as antigen binding fragments such as Fab, Fab' F (ab')2, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

Additionally, antibodies specific for the epitopes described herein are readily isolated by screening antibody phage display libraries. For example, an antibody phage library is optionally screened by using a disease specific epitope of the current invention to identify antibody fragments specific for the disease specific epitope. Antibody fragments identified are optionally used to produce a variety of recombinant antibodies that are useful with different embodiments of the present invention. Antibody phage display libraries are commercially available, for example, through Xoma (Berkeley, California) Methods for screening antibody phage libraries are well known in the art.

Accordingly, in an embodiment, the antibody described herein comprises a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDR-H3 comprising the sequence: AGGPTGNSHFTL (SEQ ID NO: 12), ARNPVGSVNL (SEQ ID NO: 18), ARRYTGDTYLGNFNL (SEQ ID NO: 24), GRGDI (SEQ ID NO: 36), ARDIFRTNTNL (SEQ ID NO: 48), VRSSGSDWWFHI (SEQ ID NO: 122), or VRQNYEGAY (SEQ ID NO: 132). In one embodiment, the sequence of said CDR-H3 comprises the sequence AGGPTGNSHFTL (SEQ ID NO: 12). In one embodiment, the sequence of said CDR-H3 comprises the sequence ARNPVGSVNL (SEQ ID NO: 18). In one embodiment, the sequence of said CDR-H3 comprises the sequence ARRYTGDTYLGNFNL (SEQ ID NO: 24). In one embodiment, the sequence of said CDR-H3 comprises the sequence GRGDI (SEQ ID NO: 36). In one embodiment, the sequence of said CDR-H3 comprises the sequence ARDIFRTNTNL (SEQ ID NO: 48). In one embodiment, the sequence of said CDR-H3 comprises the sequence VRSSGSDWWFHI (SEQ ID NO: 122). In one embodiment, the sequence of said CDR-H3 comprises the sequence VRQNYEGAY (SEQ ID NO: 132).

Accordingly, in an embodiment, the antibody described herein comprises a light chain variable region and a heavy chain variable region, the heavy chain variable region comprising complimentary determining regions CDR-H1, CDR-H2 and CDR-H3, the light chain variable region comprising complementarity determining regions CDR-L1, CDR-L2 and CDR-L3 and with the amino acid sequences of said CDR-H3 and CDR-L3 comprising the sequences: AGGPTGNSHFTL (SEQ ID NO: 12) and SGYKRVTTD-GIA (SEQ ID NO: 15); ARNPVGSVNL (SEQ ID NO: 18) and AGWRGARTDGVD (SEQ ID NO: 21); ARRYTGDTYLGNFNL (SEQ ID NO: 24) and AGGWRSLNA (SEQ ID NO: 27); GRGDI (SEQ ID NO: 36) and LGNYDCSSVDCGA (SEQ ID NO: 39); AGGPTGNSHFTL (SEQ ID NO: 42) and AGYKSPTTD-GIA (SEQ ID NO: 45); ARDIFRTNTNL (SEQ ID NO: 48) and LGGYDCSSRVCGA (SEQ ID NO: 51); VRSSGSDWWFHI (SEQ ID NO: 122) and QGYFSGFITT (SEQ ID NO: 125); or VRQNYEGAY (SEQ ID NO: 132) and FQSSHVPWT (SEQ ID NO: 135).

In one embodiment, the amino acid sequences of said CDR-H3 and CDR-L3 comprise the sequences: AGGPTGNSHFTL (SEQ ID NO: 12) and SGYKRVTTD-GIA (SEQ ID NO: 15). In one embodiment, the amino acid sequences of said CDR-H3 and CDR-L3 comprise the sequences: ARNPVGSVNL (SEQ ID NO: 18) and AGWR-GARTDGVD (SEQ ID NO: 21). In one embodiment, the amino acid sequences of said CDR-H3 and CDR-L3 comprise the sequences: ARRYTGDTYLGNFNL (SEQ ID NO: 24) and AGGWRSLNA (SEQ ID NO: 27). In one embodiment, the amino acid sequences of said CDR-H3 and CDR-L3 comprise the sequences: GRGDI (SEQ ID NO: 36) and LGNYDCSSVDCGA (SEQ ID NO: 39). In one embodiment, the amino acid sequences of said CDR-H3 and CDR-L3 comprise the sequences: AGGPTGNSHFTL (SEQ ID NO: 42) and AGYKSPTTDGIA (SEQ ID NO: 45). In one embodiment, the amino acid sequences of said CDR-H3 and CDR-L3 comprise the sequences: ARDIFRTNTNL (SEQ ID NO: 48) and LGGYDCSSRVCGA (SEQ ID NO: 51). In one embodiment, the amino acid sequences of said CDR-H3 and CDR-L3 comprise the sequences: VRSSGSDWWFHI (SEQ ID NO: 122) and QGYFSGFITT (SEQ ID NO: 125). In one embodiment, the amino acid sequences of said CDR-H3 and CDR-L3 comprise the sequences: VRQNYEGAY (SEQ ID NO: 132) and FQSSHVPWT (SEQ ID NO: 135).

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

```
CDR-H1:
                            SEQ ID NO: 10
GFSLSRYY;

CDR-H2:
                            SEQ ID NO: 11
IIPGGTT;

CDR-H3:
                            SEQ ID NO: 12
AGGPTGNSHFTL;

CDR-L1:
                            SEQ ID NO: 13
ESVYNNNH;

CDR-L2:
                            SEQ ID NO: 14
EAS; and

CDR-L3:
                            SEQ ID NO: 15
SGYKRVTTDGIA.
```

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

```
CDR-H1:
                            SEQ ID NO: 16
GFSFSSNYV;

CDR-H2:
                            SEQ ID NO: 17
IWFAGIVDTT;

CDR-H3:
                            SEQ ID NO: 18
ARNPVGSVNL;

CDR-L1:
                            SEQ ID NO: 19
ESVYSNNR;

CDR-L2:
                            SEQ ID NO: 20
YAS; and

CDR-L3:
                            SEQ ID NO: 21
AGWRGARTDGVD.
```

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

```
CDR-H1:
                            SEQ ID NO: 22
GFSFSSSYV;

CDR-H2:
                            SEQ ID NO: 23
SDTGINT ;

CDR-H3:
                            SEQ ID NO: 24
ARRYTGDTYLGNFNL ;

CDR-L1:
                            SEQ ID NO: 25
QSVYKNNY ;

CDR-L2:
                            SEQ ID NO: 26
KAS ; and

CDR-L3:
                            SEQ ID NO: 27
AGGWRSLNA.
```

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

```
CDR-H1:
                            SEQ ID NO: 28
EFSFSSRYW;

CDR-H2:
                            SEQ ID NO: 29
IYTGSIDAT;

CDR-H3:
                            SEQ ID NO: 30
VRGSDAWGLYFNL;

CDR-L1:
                            SEQ ID NO: 31
QSIHKNNY;

CDR-L2:
                            SEQ ID NO: 32
FAS; and

CDR-L3:
                            SEQ ID NO: 33
AGVYSGRIFA.
```

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

CDR-H1:
                                    SEQ ID NO: 34
GFSLSSYT;

CDR-H2:
                                    SEQ ID NO: 35
IYGGIGST;

CDR-H3:
                                    SEQ ID NO: 36
GRGDI;

CDR-L1:
                                    SEQ ID NO: 37
QSVYKNR;

CDR-L2:
                                    SEQ ID NO: 38
GAS; and

CDR-L3:
                                    SEQ ID NO: 39
LGNYDCSSVDCGA.

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

CDR-H1:
                                    SEQ ID NO: 40
GFSFSAYY;

CDR-H2:
                                    SEQ ID NO: 41
TIPIGRT;

CDR-H3:
                                    SEQ ID NO: 42
AGGPTGNSHFTL;

CDR-L1:
                                    SEQ ID NO: 43
ESVYNNNQ;

CDR-L2:
                                    SEQ ID NO: 44
QAS; and

CDR-L3:
                                    SEQ ID NO: 45
AGYKSPTTDGIA.

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

CDR-H1:
                                    SEQ ID NO: 46
GFSLSSYA;

CDR-H2:
                                    SEQ ID NO: 47
IYNYET;

-continued

CDR-H3:
                                    SEQ ID NO: 48
ARDIFRTNTNL;

CDR-L1:
                                    SEQ ID NO: 49
QSVYKNNG;

CDR-L2:
                                    SEQ ID NO: 50
FTS; and

CDR-L3:
                                    SEQ ID NO: 51
LGGYDCSSRVCGA.

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

CDR-H1:
                                    SEQ ID NO: 120
GFSLSSYN;

CDR-H2:
                                    SEQ ID NO: 121
IGTGGIT;

CDR-H3:
                                    SEQ ID NO: 122
VRSSGSDWWFHI;

CDR-L1:
                                    SEQ ID NO: 123
QSVYNNNN;

CDR-L2:
                                    SEQ ID NO: 124
RAS; and

CDR-L3:
                                    SEQ ID NO: 125
QGYFSGFITT.

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

CDR-H1:
                                    SEQ ID NO: 130
GFTFSSYY;

CDR-H2:
                                    SEQ ID NO: 131
INSNGGST;

CDR-H3:
                                    SEQ ID NO: 132
VRQNYEGAY;

CDR-L1:
                                    SEQ ID NO: 133
QSIVHSNGNTY;

-continued

```
CDR-L2:
                                    SEQ ID NO: 134
KVS; and

CDR-L3:
                                    SEQ ID NO: 135
FQSSHVPWT.
```

In an aspect, the disclosure provides an antibody comprising a light chain variable region and a heavy chain variable region, optionally fused, the heavy chain variable region comprising complementarity determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

```
CDR-H1:
                                    SEQ ID NO: 140
GFTFSSYY;

CDR-H2:
                                    SEQ ID NO: 141
INTNGGST;

CDR-H3:
                                    SEQ ID NO: 142
VRQNYEGAY;

CDR-L1:
                                    SEQ ID NO: 143
QSIVHSNGNTY;

CDR-L2:
                                    SEQ ID NO: 144
KVS; and

CDR-L3:
                                    SEQ ID NO: 145
FQSSHVPWT.
```

In an embodiment, the antibody comprises a heavy chain variable region comprising: i) an amino acid sequence as set forth in SEQ ID NO: 98, ii) an amino acid sequence with at least 50%, at least 60%, at least 70%, at least 80% or at least 90% sequence identity to SEQ ID NO: 98, wherein the CDR sequences are as set forth in SEQ ID NOs: 10-12, or iii) a conservatively substituted amino acid sequence of i), and/or wherein the antibody comprises a light chain variable region comprising an amino acid sequence as set forth in SEQ ID NO: 99, ii) an amino acid sequence with at least 50%, at least 60%, at least 70%, at least 80% or at least 90% sequence identity to SEQ ID NO: 99, wherein the CDR sequences are as set forth in SEQ ID NOS: 13-15, or iii) a conservatively substituted amino acid sequence of i), optionally wherein the heavy chain variable region amino acid sequence is encoded by a nucleotide sequence as set out in SEQ ID NO: 76 or a codon degenerate or optimized version thereof and/or the light chain variable region amino acid sequence is encoded by a nucleotide sequence as set out in SEQ ID NO: 77 or a codon degenerate or optimized version thereof.

In an embodiment, the antibody comprises a heavy chain variable region comprising: i) an amino acid sequence as set forth in SEQ ID NO: 100, ii) an amino acid sequence with at least 50%, at least 60%, at least 70%, at least 80% or at least 90% sequence identity to SEQ ID NO: 100, wherein the CDR sequences are as set forth in SEQ ID NOs: 16-18, or iii) a conservatively substituted amino acid sequence of i), and/or wherein the antibody comprises a light chain variable region comprising an amino acid sequence as set forth in SEQ ID NO: 101, ii) an amino acid sequence with at least 50%, at least 60%, at least 70%, at least 80% or at least 90% sequence identity to SEQ ID NO: 101, wherein the CDR sequences are as set forth in SEQ ID NOS: 19-21, or iii) a conservatively substituted amino acid sequence of i), optionally wherein the heavy chain variable region amino acid sequence is encoded by a nucleotide sequence as set out in SEQ ID NO: 78 or a codon degenerate or optimized version thereof and/or the light chain variable region amino acid sequence is encoded by a nucleotide sequence as set out in SEQ ID NO: 79 or a codon degenerate or optimized version thereof.

In an embodiment, the antibody comprises a heavy chain variable region comprising: i) an amino acid sequence as set forth in SEQ ID NO: 102, ii) an amino acid sequence with at least 50%, at least 60%, at least 70%, at least 80% or at least 90% sequence identity to SEQ ID NO: 102, wherein the CDR sequences are as set forth in SEQ ID NOS: 22-24, or iii) a conservatively substituted amino acid sequence of i), and/or wherein the antibody comprises a light chain variable region comprising an amino acid sequence as set forth in SEQ ID NO: 103, ii) an amino acid sequence with at least 50%, at least 60%, at least 70%, at least 80% or at least 90% sequence identity to SEQ ID NO: 103, wherein the CDR sequences are as set forth in SEQ ID NOS: 25-27, or iii) a conservatively substituted amino acid sequence of i), optionally wherein the heavy chain variable region amino acid sequence is encoded by a nucleotide sequence as set out in SEQ ID NO: 80 or a codon degenerate or optimized version thereof and/or the light chain variable region amino acid sequence is encoded by a nucleotide sequence as set out in SEQ ID NO: 81 or a codon degenerate or optimized version thereof.

In an embodiment, the antibody comprises a heavy chain variable region comprising: i) an amino acid sequence as set forth in SEQ ID NO: 104, ii) an amino acid sequence with at least 50%, at least 60%, at least 70%, at least 80% or at least 90% sequence identity to SEQ ID NO: 104, wherein the CDR sequences are as set forth in SEQ ID NOs: 28-30, or iii) a conservatively substituted amino acid sequence of i), and/or wherein the antibody comprises a light chain variable region comprising an amino acid sequence as set forth in SEQ ID NO: 105, ii) an amino acid sequence with at least 50%, at least 60%, at least 70%, at least 80% or at least 90% sequence identity to SEQ ID NO: 105, wherein the CDR sequences are as set forth in SEQ ID NOS: 31-33, or iii) a conservatively substituted amino acid sequence of i), optionally wherein the heavy chain variable region amino acid sequence is encoded by a nucleotide sequence as set out in SEQ ID NO: 82 or a codon degenerate or optimized version thereof and/or the light chain variable region amino acid sequence is encoded by a nucleotide sequence as set out in SEQ ID NO: 83 or a codon degenerate or optimized version thereof.

In an embodiment, the antibody comprises a heavy chain variable region comprising: i) an amino acid sequence as set forth in SEQ ID NO: 106, ii) an amino acid sequence with at least 50%, at least 60%, at least 70%, at least 80% or at least 90% sequence identity to SEQ ID NO: 106, wherein the CDR sequences are as set forth in SEQ ID NOs: 34-36, or iii) a conservatively substituted amino acid sequence of i), and/or wherein the antibody comprises a light chain variable region comprising an amino acid sequence as set forth in SEQ ID NO: 107, ii) an amino acid sequence with at least 50%, at least 60%, at least 70%, at least 80% or at least 90% sequence identity to SEQ ID NO: 107, wherein the CDR sequences are as set forth in SEQ ID NOS: 37-39, or iii) a conservatively substituted amino acid sequence of i), optionally wherein the heavy chain variable region amino acid sequence is encoded by a nucleotide sequence as set out in SEQ ID NO: 84 or a codon degenerate or optimized version thereof and/or the light chain variable region amino acid sequence is encoded by a nucleotide sequence as set out in SEQ ID NO: 85 or a codon degenerate or optimized version thereof.

In an embodiment, the antibody comprises a heavy chain variable region comprising: i) an amino acid sequence as set forth in SEQ ID NO: 108, ii) an amino acid sequence with at least 50%, at least 60%, at least 70%, at least 80% or at least 90% sequence identity to SEQ ID NO: 108, wherein the CDR sequences are as set forth in SEQ ID NOs: 40-42, or iii) a conservatively substituted amino acid sequence of i), and/or wherein the antibody comprises a light chain variable region comprising an amino acid sequence as set forth in SEQ ID NO: 109, ii) an amino acid sequence with at least 50%, at least 60%, at least 70%, at least 80% or at least 90% sequence identity to SEQ ID NO: 109, wherein the CDR sequences are as set forth in SEQ ID NOS: 43-45, or iii) a conservatively substituted amino acid sequence of i), optionally wherein the heavy chain variable region amino acid sequence is encoded by a nucleotide sequence as set out in SEQ ID NO: 86 or a codon degenerate or optimized version thereof and/or the light chain variable region amino acid sequence is encoded by a nucleotide sequence as set out in SEQ ID NO: 87 or a codon degenerate or optimized version thereof.

In an embodiment, the antibody comprises a heavy chain variable region comprising: i) an amino acid sequence as set forth in SEQ ID NO: 110, ii) an amino acid sequence with at least 50%, at least 60%, at least 70%, at least 80% or at least 90% sequence identity to SEQ ID NO: 110, wherein the CDR sequences are as set forth in SEQ ID NOS: 46-48, or iii) a con-servatively substituted amino acid sequence of i), and/or wherein the antibody comprises a light chain variable region comprising an amino acid sequence as set forth in SEQ ID NO: 111, ii) an amino acid sequence with at least 50%, at least 60%, at least 70%, at least 80% or at least 90% sequence identity to SEQ ID NO: 111, wherein the CDR sequences are as set forth in SEQ ID NOS: 49-51, or iii) a conservatively substituted amino acid sequence of i), optionally wherein the heavy chain variable region amino acid sequence is encoded by a nucleotide sequence as set out in SEQ ID NO: 88 or a codon degenerate or optimized version thereof and/or the light chain variable region amino acid sequence is encoded by a nucleotide sequence as set out in SEQ ID NO: 89 or a codon degenerate or optimized version thereof.

In an embodiment, the antibody comprises a heavy chain variable region comprising: i) an amino acid sequence as set forth in SEQ ID NO: 128, ii) an amino acid sequence with at least 50%, at least 60%, at least 70%, at least 80% or at least 90% sequence identity to SEQ ID NO: 128, wherein the CDR sequences are as set forth in SEQ ID NOS: 120-122, or iii) a conservatively substituted amino acid sequence of i), and/or wherein the antibody comprises a light chain variable region comprising an amino acid sequence as set forth in SEQ ID NO: 129, ii) an amino acid sequence with at least 50%, at least 60%, at least 70%, at least 80% or at least 90% sequence identity to SEQ ID NO: 129, wherein the CDR sequences are as set forth in SEQ ID NOS: 123-125, or iii) a conservatively substituted amino acid sequence of i), optionally wherein the heavy chain variable region amino acid sequence is encoded by a nucleotide sequence as set out in SEQ ID NO: 126 or a codon degenerate or optimized version thereof and/or the light chain variable region amino acid sequence is encoded by a nucleotide sequence as set out in SEQ ID NO: 127 or a codon degenerate or optimized version thereof.

In an embodiment, the antibody comprises a heavy chain variable region comprising: i) an amino acid sequence as set forth in SEQ ID NO: 138, ii) an amino acid sequence with at least 50%, at least 60%, at least 70%, at least 80% or at least 90% sequence identity to SEQ ID NO: 138, wherein the CDR sequences are as set forth in SEQ ID NOs: 130-132, or iii) a conservatively substituted amino acid sequence of i), and/or wherein the antibody comprises a light chain variable region comprising an amino acid sequence as set forth in SEQ ID NO: 129, ii) an amino acid sequence with at least 50%, at least 60%, at least 70%, at least 80% or at least 90% sequence identity to SEQ ID NO: 129, wherein the CDR sequences are as set forth in SEQ ID NOS: 133-135, or iii) a conservatively substituted amino acid sequence of i), optionally wherein the heavy chain variable region amino acid sequence is encoded by a nucleotide sequence as set out in SEQ ID NO: 136 or a codon degenerate or optimized version thereof and/or the light chain variable region amino acid sequence is encoded by a nucleotide sequence as set out in SEQ ID NO: 137 or a codon degenerate or optimized version thereof.

In an embodiment, the antibody comprises a heavy chain variable region comprising: i) an amino acid sequence as set forth in SEQ ID NO: 148, ii) an amino acid sequence with at least 50%, at least 60%, at least 70%, at least 80% or at least 90% sequence identity to SEQ ID NO: 148, wherein the CDR sequences are as set forth in SEQ ID NOs: 140-142, or iii) a conservatively substituted amino acid sequence of i), and/or wherein the antibody comprises a light chain variable region comprising an amino acid sequence as set forth in SEQ ID NO: 149, ii) an amino acid sequence with at least 50%, at least 60%, at least 70%, at least 80% or at least 90% sequence identity to SEQ ID NO: 149, wherein the CDR sequences are as set forth in SEQ ID NOs: 143-145, or iii) a conservatively substituted amino acid sequence of i), optionally wherein the heavy chain variable region amino acid sequence is encoded by a nucleotide sequence as set out in SEQ ID NO: 146 or a codon degenerate or optimized version thereof and/or the light chain variable region amino acid sequence is encoded by a nucleotide sequence as set out in SEQ ID NO: 147 or a codon degenerate or optimized version thereof.

In an embodiment, the antibody comprises a heavy chain variable region comprising a conservatively substituted amino acid sequence as set forth in any in one of SEQ ID NOS: 98, 100, 102, 104, 106, 108, 110, 128, 138, or 148. In an embodiment, the antibody comprises a heavy chain variable region comprising a conservatively substituted amino acid sequence as set forth in any in one of SEQ ID NOs: 99, 101, 103, 105, 107, 109, 111, 129, 139, or 149. For example, the heavy chain variable region and/or the light chain variable region, optionally framework region 1, 2 and/or 3, can include 1, 2, 3, 4 or 5 conservative amino acid substitutions.

In an embodiment, the antibody is a monoclonal antibody. In an embodiment, the antibody is a chimeric antibody such as a humanized antibody. In an embodiment, the antibody is a single chain antibody.

In an embodiment, the antibody is affinity purified.

In an embodiment, the antibody is raised or screened using an isolated peptide or immunogen described herein.

Another aspect includes an antibody that competes for binding to human misfolded TDP43 with an antibody described herein, optionally an antibody comprising a CDR set described herein.

Competition between antibodies can be determined for example using an assay in which an antibody under test is assessed for its ability to inhibit specific binding of a reference antibody to the common antigen. A test antibody competes with a reference antibody if an excess of a test antibody (e.g., at least a 2 fold, 5, fold, 10 fold or 20 fold) inhibits binding of the reference antibody by at least 50%, at least 75%, at least 80%, at least 90% or at least 95% as measured in a competitive binding assay.

A further aspect is an antibody conjugated to a detectable label. In an embodiment, the detectable label is a positron-emitting radionuclide. A positron-emitting radionuclide can be used for example in PET imaging.

Accordingly, an embodiment provides an immunoconjugate comprising an antibody described herein and a detectable label.

A further aspect relates to an antibody complex comprising an antibody described herein and/or a binding fragment thereof and misfolded TDP-43. A further aspect is an isolated nucleic acid encoding an antibody or part thereof described herein.

Nucleic acids encoding a heavy chain or a light chain are also provided, for example encoding a heavy chain comprising CDR-H1, CDR-H2 and/or CDR-H3 regions described herein or encoding a light chain comprising CDR-L1, CDR-L2 and/or CDR-L3 regions described herein and more particularly in Table 3.

For example, the nucleic acid sequence comprises any one of SEQ ID NOS: 76-89, SEQ ID NOs: 126-127, SEQ ID NOs: 136-137 and/or SEQ ID NOS: 146-147.

The present disclosure also provides variants of the nucleic acid sequences that encode the antibody disclosed herein.

For example, the variants include nucleotide sequences that hybridize to the nucleic acid sequences encoding the antibody disclosed herein under at least moderately stringent hybridization conditions or codon degenerate or optimized sequences. In another embodiment, the variant nucleic acid sequences have at least 50%, at least 60%, at least 70%, most preferably at least 80%, even more preferably at least 90% and even most preferably at least 95% sequence identity to nucleic acid sequences comprising any one of SEQ ID NOs: 76-89, SEQ ID NOS: 126-127, SEQ ID NOS: 136-137 and/or SEQ ID NOs: 146-147.

A further aspect provides an isolated nucleic acid encoding the amino acid residues of an isolated peptide, immunogen, or antibody described herein.

Another aspect is an expression cassette or vector comprising the nucleic acid herein disclosed. In an embodiment, the vector is an isolated vector.

The vector can be any vector, including vectors suitable for producing an antibody and/or binding fragment thereof or expressing a peptide sequence described herein.

The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes/peptides or antibodies described herein.

In an embodiment, the vector is suitable for expressing for example single chain antibodies (e.g. intrabodies). Suitable regulatory sequences may be derived from a variety of sources, including bacterial, fungal, viral, mammalian, or insect genes. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. In an embodiment, the regulatory sequences direct or increase expression in neural tissue and/or cells. In an embodiment, the vector is a viral vector. The recombinant expression vectors may also contain a marker gene which facilitates the selection of host cells transformed, infected or transfected with a vector for expressing an antibody or epitope peptide described herein. The recombinant expression vectors may also contain expression cassettes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, MA) and pRIT5 (Pharmacia, Piscataway, NJ) which fuse glutathione S-transferase (GST), maltose E binding protein, or protein A, respectively, to the recombinant protein.

Also provided in another aspect is a cell expressing an antibody described herein. In an embodiment, the cell is an isolated and/or recombinant cell, expressing an antibody described herein or comprising a vector herein disclosed. In an embodiment, the cell is a fused cell such as a hybridoma.

The recombinant cell can be generated using any cell suitable for producing a polypeptide, for example suitable for producing an antibody and/or binding fragment thereof. For example to introduce a nucleic acid (e.g. a vector) into a cell, the cell may be transfected, transformed or infected, depending upon the vector employed.

Suitable host cells include a wide variety of prokaryotic and eukaryotic host cells. For example, the proteins described herein may be expressed in bacterial cells such as _E. coli_, insect cells (using baculovirus), yeast cells or mammalian cells.

In an embodiment, the cell is a eukaryotic cell selected from a yeast, plant, worm, insect, avian, fish, reptile and mammalian cell.

In another embodiment, the mammalian cell is a myeloma cell, a spleen cell, or a hybridoma cell.

In an embodiment, the cell is a neural cell.

Yeast and fungi host cells suitable for expressing an antibody or peptide include, but are not limited to _Saccharomyces cerevisiae, Schizosaccharomyces pombe_, the genera _Pichia_ or _Kluyveromyces_ and various species of the genus _Aspergillus_. Examples of vectors for expression in yeast _S. cerivisiae_ include pYepSec1, pMFa, pJRY88, and pYES2 (Invitrogen Corporation, San Diego, CA). Protocols for the transformation of yeast and fungi are well known to those of ordinary skill in the art.

Mammalian cells that may be suitable include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

In an embodiment, the cell is a fused cell such as a hybridoma cell, the hybridoma cell producing an antibody specific and/or selective for an epitope or epitope sequence described herein, including for example that selectively binds misfolded TDP-43.

A further aspect is a hybridoma cell line producing an antibody specific for an epitope described herein.

IV. Compositions

A further aspect is a composition comprising an isolated peptide, immunogen, antibody, or immunoconjugate described herein. Also provided is a composition comprising two or more of an isolated peptide, immunogen, antibody, or immunoconjugate described herein.

In an embodiment, the composition comprises a diluent. Suitable diluents for nucleic acids and vectors include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

In an embodiment comprising a peptide, compound or immunogen described herein, the composition comprises an adjuvant.

In an embodiment, the adjuvant is selected from alum, monophosphoryl lipid A and QS21.

Adjuvants that can be used for example, include Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Aluminum hydroxide, aluminum sulfate and aluminum phosphate (collectively commonly referred to as alum) are routinely used as adjuvants. A wide range of extrinsic adjuvants can provoke potent immune responses to immunogens. These include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In an embodiment, the adjuvant is aluminum hydroxide. In another embodiment, the adjuvant is aluminum phosphate. Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immuno-stimulating agents such as muramyl peptides (for example, N-acetylmuramyl-L-threonyl-D-isoglutamine (thr-MDP),- acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-AI-D-isoglu-L-Ala-dipalmitoxy propylamide (DTP-DPP) theramide (TM), or other bacterial cell wall components.

The adjuvant may be administered with an immunogen as a single composition. Alternatively, an adjuvant may be administered before, concurrent and/or after administration of the immunogen.

In an embodiment, the composition comprises an antibody or part thereof described herein. In another embodiment, the composition comprises an antibody or part thereof described herein and a diluent. In an embodiment, the composition is a sterile composition.

In some embodiments the composition is sterile.

In an embodiment, the composition is for a method described herein such as detecting misfolded TDP-43.

In an embodiment, the composition comprises a pharmaceutically acceptable carrier, diluent, and/or excipient. In an embodiment, the composition is a pharmaceutical composition, for example for a method described herein such as for treating a subject in need thereof e.g. a subject with a TDP-43 proteinopathy.

The composition can comprise one or more antibodies described herein.

V. Kits and Packages

A further aspect relates to a kit or package comprising i) an isolated peptide, ii) an immunogen, iii) an antibody, iv) an immunoconjugate v) an isolated nucleic acid, or vi) composition, comprised in a vial such as a sterile vial or other housing and optionally a reference agent and/or instructions for use thereof.

In an embodiment, the kit is an ELISA. In an embodiment, the kit is a multiplex assay or a planar array kit, for example similar to those available through MesoScale, Quanterix or Singulex or for performing a method described herein.

In an embodiment, the kit comprises an antibody described herein contained in a container such as a sterile vial.

In an embodiment, the kit comprises instructions for use for an ELISA or a method described herein.

VI. Methods

Included are methods for making the isolated peptides, immunogens and antibodies described herein.

In particular, provided are methods of making an antibody selective for W68 in the context of DAGWGNL (SEQ ID NO:1) or related epitope. In an embodiment, the method comprises administering an isolated peptide, immunogen, or composition described herein to a non-human subject and isolating antibodies that selectively bind the TDP-43 peptide of the immunogen and/or misfolded TDP-43. For example, isolating the antibody can involve one or more methods described in the application.

In an embodiment, the method comprises isolating antibodies that selectively bind the TDP-43 peptide of the immunogen and/or misfolded TDP-43 from an expression library encoding immunoglobulin genes, or portions thereof. Optionally, the expression library is a phage display library.

A further aspect includes a method of inducing an immune response in a non-human subject, comprising administering to the subject a compound, immunogen and/or composition comprising a compound described herein; and optionally isolating cells and/or antibodies that specifically bind the compound or immunogen administered.

In an embodiment, the method further comprises isolating an antibody that specifically binds W68 in the context of DAGWGNL (SEQ ID NO: 1) or a related epitope.

In an embodiment, the method further comprises forming an antibody-producing hybridoma. For example as discussed above, monoclonal antibodies can be made using a method described herein.

A further aspect provides an antibody produced by the methods described herein.

A further aspect provides a method of detecting whether a sample comprises misfolded TDP-43.

In an embodiment, the method comprises:

a. contacting the sample with the antibody described herein under conditions permissive to produce an antibody: misfolded TDP-43 polypeptide complex; and b. detecting the presence of any complex;

wherein the presence of detectable complex is indicative that the sample may contain misfolded TDP-43 polypeptide.

In another embodiment, the method comprises:

(a) contacting a test sample of said subject with an antibody described herein, under conditions permissive to produce an antibody-antigen complex;

(b) measuring the amount of the antibody-antigen complex in the test sample; and (c) comparing the amount of antibody-antigen complex in the test sample to a control;

wherein detecting antibody-antigen complex in the test sample as compared to the control indicates that the sample comprises misfolded TDP-43.

The measuring may for example by immunofluorescence. The methods may also include colocalization staining for example pan-TDP-43 staining.

In an embodiment, the sample is a biological sample. In an embodiment, the sample comprises blood, serum, plasma, brain tissue, spinal cord tissue or an extract thereof and/or CSF. The sample can also be a fraction. For example, the sample can comprise extracellular vesicles from brain, CSF and/or blood. In an embodiment, the sample is obtained from a human subject.

In an embodiment, the sample is from a subject with ALS. In another embodiment, the sample is from a subject with FTD. In an embodiment, the sample is from limbic-predominant age-related TDP-43 encephalopathy (LATE).

A number of methods can be used to determine if misfolded TDP-43 polypeptides is present in a sample using the antibodies described herein, including immunoassays such as flow cytometry, dot or slot blots, Western blots, ELISA, and immunoprecipitation followed by SDS-PAGE immunocytochemistry. Other immune based methods that can be used include singleplex and multiplex immunoassay platforms.

Singleplex bead-based platforms can be used in which individual immunocomplexes are isolated on paramagnetic beads and detected. Suitable bead-based singleplex platforms include those available from Quanterix.

Multiplex immunoassay platforms suitable for these purposes include bead- or particle-based platforms, and planar array platforms.

Bead- or particle-based platforms can be used in which the capture antibody is immobilized on a particle such as a fluorescently dyed bead or paramagnetic bead, and analyte is detected with a second detection antibody. Suitable bead-based multiplex platforms include for example Luminex® from AbCam, FirePlex™ from AbCam, and those available from Quanterix.

Planar array platforms can be used in which the capture antibody is immobilized in a micro-arrayed format on a solid surface such as a membrane, a glass surface, or an individual well of for example a 96- or 384-well plate, and analyte is detected with a second detection antibody. For spatial separation of micro-arrayed platforms, spot coordinates can be used to identify detected analyte. Suitable planar array platforms include those available from for example Quaternix or Mesoscale.

Bead- or particle-based assays utilizing a fluorescently labeled detection antibody may be followed by single-molecule counting in which the detection antibodies are eluted from the immunocomplex and quantified by detecting and counting individual fluorescent molecules using capillary fluidics and a laser. Suitable technologies include those available from for example Singulex.

Surface plasmon resonance can be used to assess conformation specific binding.

A labelled antibody described herein can also be administered to a subject to detect the location of misfolded TDP-43.

Also provided is a method of inhibiting misfolded TDP-43 cell to cell transmission, the method comprising administering an antibody described herein to a subject in need thereof, e.g a subject suspected of having, at risk of developing or diagnosed with a TDP-43 proteinopathy.

Also provided is a method of treating a TDP-43 proteinopathy, the method comprising administering to a subject in need thereof an effective amount of an antibody, immunoconjugate, composition comprising said antibody of immunoconjugate, of the disclosure described herein.

In an embodiment, the TDP-43 proteinopathy is selected from amyotrophic lateral sclerosis (ALS), frontotemporal lobar degeneration (FTLD-TDP), primary lateral sclerosis, progressive muscular atrophy, and limbic-predominant age-related TDP-43 encephalopathy (LATE).

A further aspect is a method of treating a subject comprising administering to a subject in need thereof an effective amount of an antibody or immunoconjugate of the disclosure described herein, or a composition comprising said antibody or immunoconjugate, optionally in combination with another TDP-43 proteinopathy treatment. Other TDP-43 proteinopathy treatments include, but are not limited to treatments for ALS such as Riluzole (Rilutek or Tiglutik™), Edaravone (Radicava™), and Nuedexta™ (combination of dextromethorphan and quinidine).

The antibody can for example be comprised in a composition as described herein for example in combination with a pharmaceutically acceptable carrier, diluent and/or excipient and formulated for example in vesicles for improving delivery. Combinations of antibodies (e.g. 2 or more antibodies) and/or immunoconjugates can also be used.

The compositions, antibodies, immunogens, and immunoconjugates described herein can be administered for example, by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

In certain embodiments, the composition is administered systemically.

Other embodiments contemplate the co-administration of the compositions, antibodies, and immunoconjugates described herein with biologically active molecules known to facilitate the transport across the blood brain barrier.

Also contemplated in certain embodiments, are methods for administering the compositions, antibodies, and immunoconjugates described herein across the blood brain barrier such as those directed at transiently increasing the permeability of the blood brain barrier as described in U.S. Pat. No. 7,012,061 "Method for increasing the permeability of the blood brain barrier", herein incorporated by reference.

Also contemplated herein is the viral delivery of the compositions and/or nucleic acids described herein for expression of one or more antibodies described herein in a subject in need thereof or in a cell. An aspect includes a method of treating a subject comprising administering to a subject in need thereof an effective amount of a vectorized antibody of the disclosure described herein, or a composition comprising said vectorized antibody, optionally in combination with another TDP-43 proteinopathy treatment. In one embodiment, the vectorized antibody is a viral vector comprising a nucleic acid encoding an antibody described therein. In one embodiment, the method is for intracellular expression of an intrabody in a subject in need thereof. Intrabodies can for example inhibit intracellular misfolded TDP-43 aggregation or promote clearance of misfolded aggregates.

The vectorized antibody can be in a composition. Non viral vectors can also be used, for example adeno-associated virus (AAV, for example AAV9) and lentiviral vectors etc. In certain embodiments, the nucleic acid and/or vector can be injected intraventricularly or intrathecally.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

TDP-43 Epitope

TDP-43 NTD comprises a ubiquitin-like domain. TDP-43 NTD Trp68 is uniquely present in TDP-43 when aligned to other ubiquitin like domain containing proteins (e.g. human ubiquitin, axin1, human and Dvl-2) [9]. It was determined that Trp68 is not solvent exposed in PDB structures such as PDBID 2N4P and 6B1G. It was hypothesized that Trp68 (i.e. position in human sequence as represented in NM_007375.3) may be solvent exposed (antibody accessible) in misfolded TDP-43. A seven amino acid peptide centered around tryptophan 68 was selected and an immunogen designed as described in Example 2.

Example 2

Immunogen Construction

The peptide DAGWGNLc (SEQ ID NO: 9) was synthesized according to standard protocols (GenScript USA Inc, Piscataway, NJ). The N-terminus of the peptide was acetylated.

The synthesized peptide was then conjugated via the C-terminal cys residue to keyhole limpet hemocyanin (KLH) (for immunizing) or BSA (for screening) to produce the immunogen used in Example 3.

Example 3

Polyclonal Antibody Generation and Selection

The immunogen comprising the peptide DAGWGNL (SEQ ID NO: 1) linked to KLH via a C-terminal cysteine was used to raise polyclonal antibodies.

Immunization

Two new zealand rabbits (designated GS240 and GS243) were immunized (primary and two boost injections per animal) using the KLH conjugated DAGWGNLc (SEQ ID NO: 9) peptide described in Example 2. After the third immunization, blood was let from each rabbit and antiserum was isolated.

Preservative (0.02% sodium azide final concentration) was added to each the isolated antiserum (unpurified antiserum). Preimmune serum was also obtained for each animal and combined with preservative (0.02% sodium azide).

Affinity Purification

The IgG fraction of each rabbit antiserum was isolated by sulphate precipitation. The precipitate was then subjected to affinity-column precipitation in which a resin was prepared with the DAGWGNL peptide. After the antiserum was incubated in the column, antibodies were eluted using a step-wise pH gradient in PBS. The final concentration was determined by BCA assay and titration was performed by ELISA. The affinity purified antibody from GS240 had a concentration of about 0.5 mg/ml and the affinity purified antibody from GS243 had a concentration of about 0.6 mg/mL.

ELISA Conditions:

ELISA plates were coated with 4 ug/well of DAGWGNL (SEQ ID NO: 1) peptide, 100 µL/well in PBS (pH 7.4) overnight at 4° C.

The secondary antibody used was anti-rabbit IgG Fc monoclonal secondary antibody conjugated to HRP (GenScript, Cat. No. A01856).

The ELISA results are presented in Tables 1A and 1B for which shows the binding of serial dilutions of the unpurified antiserums (1A) and the affinity purified antibodies (1B) generated against the immunizing peptide.

TABLE 1A

| Antiserum for DAGWGNL (SEQ ID NO: 1) | | | | | | |
|---|---|---|---|---|---|---|
| Dilution | NC | 1:1000 | 1:2000 | 1:4000 | 1:8000 | 1:16000 | 1:32000 |
| GS240 | 0.068 | 2.393 | 2.259 | 2.021 | 1.620 | 1.161 | 0.855 |
| GS243 | 0.067 | 2.649 | 2.540 | 2.535 | 2.371 | 2.291 | 1.944 |

TABLE 1A

| Antiserum for DAGWGNL (SEQ ID NO: 1) (Cont.) | | | | | |
|---|---|---|---|---|---|
| Dilution | 1:64000 | 1:128000 | 1:256000 | 1:512000 | Blank | Titer |
| GS240 | 0.552 | 0.280 | 0.191 | 0.153 | 0.054 | 1:512000 |
| GS243 | 1.714 | 1.222 | 0.686 | 0.552 | 0.077 | >1:512000 |

The titer is the highest dilution with signal/blank that is >=2.1, the OD450 in the blank is the average of two technical replicates. NC is the negative control (pre-immune serum).

33

TABLE 1B

Affinity purified antibody for DAGWGNL (SEQ ID NO: 1)

| | ng/ml | | | | | |
| --- | --- | --- | --- | --- | --- | --- |
| | 1,000 | 500 | 250 | 125 | 62.50 | 31.25 |
| | Dilution | | | | | |
| | 1:1000 | 1:2000 | 1:4000 | 1:8000 | 1:16000 | 1:32000 |
| GS240 | 2.775 | 2.762 | 2.687 | 2.520 | 2.262 | 1.956 |
| GS243 | 2.766 | 2.693 | 2.531 | 2.432 | 1.811 | 1.756 |

TABLE 1B

Affinity purified antibody for DAGWGNL (SEQ ID NO: 1) (Cont.)

| | ng/ml | | | | | |
| --- | --- | --- | --- | --- | --- | --- |
| | 15.62 | 7.81 | 3.90 | 1.95 | Blank | / |
| | Dilution | | | | | |
| | 1:64000 | 1:128000 | 1:256000 | 1:512000 | Blank | Titer |
| GS240 | 1.563 | 1.087 | 0.677 | 0.412 | 0.055 | 1:512000 |
| GS243 | 1.289 | 0.881 | 0.538 | 0.288 | 0.053 | 1:512000 |

The titer is the highest dilution with signal/blank that is >=2.1, the OD450 in the blank is the average of two technical replicates.

Example 4

Detection of Misfolded TDP-43

The affinity purified antibodies were tested for their ability to bind native TDP-43 polypeptide as well as misfolded TDP-43 polypeptide in a cell transfection assay using immunocytochemistry.

Methods

The cell culture and immunohistochemistry methods used are based on methods previously described in Pokrishevsky E, Grad L I, Cashman N R. (2016) TDP-43 or FUS-induced misfolded human wild-type SOD1 can propagate intercellularly in a prion-like fashion. Sci Rep. 2016; 6:22155. doi: 10.1038/srep22155, herein incorporated by reference.

Briefly, human embryonic kidney cells (HEK293FT; ATCC, Manassas, VA) were cultured in complete Dulbecco's Modified Eagle Medium (DMEM) containing 10% FBS, 100 U/mL penicillin, 100 µg/mL streptomycin and 2 mM L-glutamine (ThermoFisher Scientific, MA, USA) on borosilicate glass coverslips that were pre-coated with 0.01% poly-D lysine. Cells were transfected with different TDP-43 DNA plasmid constructs with the chimeric reporter protein using Lipofectamine™ LTX (ThermoFisher Scientific, MA, USA), according to manufacturer's instructions. The constructs used were: Empty Vector, HA-tagged Human TDP-43 with a triple missense tandem mutation in the nuclear localization signal (ΔNLS-TDP-43), human TDP43 with the original NLS sequence (WT-TDP43), and ΔNLS-TDP43 in which tryptophan 68 was mutated to serine (W68S).

48 hrs post transfection, cells were fixed in 4% paraformaldehyde for 1 hr at 37 C, washed quickly in cold PBS, permeabilized in 0.01% Triton X in PBS for 10 min, then blocked with 10% Normal Goat Serum (NGS) for 1 hr at room temperature. For staining, the affinity purified rabbit antibodies described in Example 3 were diluted in 10% NGS in PBS to about 0.5 ug/mL for antisera GS240 and about 0.60 ug/mL for antisera GS243, and 1 µg/ml rat anti HA tag was used (Roche Diagnostics, IN) as counterstain. Cells were incubated with both antibodies at 4° C. overnight, then washed in PBS three times before incubation with the secondary antibodies conjugated to Alexa Fluor™-568 or 647 fluorescent dyes (Life Technologies, Carlsbad, CA; 1:1000 dilution) for 1 hr at room temperature in the dark. DNA was counterstained using 2 µg/ml Bis-benzamide H33342 trihydrochloride (Hoechst 33342) for 1 min. Following four final washes in PBS the cells were mounted on a glass slide in a drop of Fluoromount-G (SouthernBiotech, Birmingham, AL). Confocal images of individual sections were captured using Leica TCS SP8™ microscope (Leica Canada) using the LAS-X™ software.

Results:

The results are presented in FIGS. 1A-1L and 2A-2L.

In FIGS. 1A, 1E, 1I, 2A, 2E and 2I, HEK293 cells transfected by an HA-tagged TDP-43 construct with a triple missense tandem mutation in the nuclear localization signal, display TDP-43 aggregates in the cytoplasm, as detected by the HA antibody. HA-positive aggregates are also apparent for ΔNLS-TDP-43 W68S transfected cells (FIGS. 1B, 1F, 1J, 2B, 2F and 2J). The affinity purified polyclonal antibodies GS240 (FIG. 1) and GS243 (FIG. 2) recognize aggregates in the ΔNLS-TDP-43 transfected cells (FIGS. 1A, 1E, 1I, 2A, 2E and 2I, comprising tryptophan 68 residue (Trp68), but do not show the same reactivity when Trp68 is mutated to serine (FIGS. 1B, 1F, 1J, 2B, 2F and 2J). Anti-DAGWGNL (SEQ ID NO: 1) polyclonal rabbit antibodies therefore have selectivity for misfolded TDP-43 NTD comprising Trp68 residue.

When HA-tagged wild-type TDP-43 is overexpressed without an alteration to the nuclear localization signal, it generally localizes to the nucleus, and nuclear TDP-43 does not bind GS240 or GS243 affinity purified sera (FIGS. 1C, 1G, 1K, 20,2G and 2K). Interestingly, GS240 and GS243 still bind wild-type TDP-43 when it is present in the cytoplasm of these cells (FIGS. 1K and 2K), suggesting that the N-terminal ubiquitin like domain (NTD) can be misfolded in WT-TDP43 when mislocalized to the cytoplasm.

GS240 and GS243 polyclonal antibodies show minimal reactivity in the absence of TDP-43 aggregates (as seen in the background staining of FIGS. 1L and 2L, empty vector transfection). Reactivity of both antibodies is selective for misfolded TDP-43 in aggregates in the cytoplasm and requires the presence of Trp68.

Example 5

Mouse Monoclonal Antibody Production

A peptide comprising DAGWGNL (SEQ ID NO: 1) such as cDAGWGNL (SEQ ID NO: 8) or DAGWGNLc (SEQ ID NO: 9) linked to KLH can be used to produce monoclonal antibodies.

Immunization Briefly, mice are immunized via a series of subcutaneous aqueous injections over an extended period, after which mice are euthanized and lymphocytes are harvested for hybridoma cell line generation.

Fusion/Hybridoma Development Lymphocytes are isolated and fused with murine SP2/0 myeloma cells in the presence of poly-ethylene glycol (PEG 1500). Fused cells are cultured using HAT selection. This method uses a semi-solid methylcellulose-based HAT selective medium to combine the hybridoma selection and cloning into one step. Single cell-derived hybridomas grow to form monoclonal colonies on the semi-solid media. Approximately 10 days after the fusion event, resulting hybridoma clones are transferred to 96-well tissue culture plates and grown in HT containing medium until mid-log growth is reached (approximately 5 days).

Hybridoma Analysis (Screening)

Tissue culture supernatants from the hybridomas can be tested by indirect ELISA on screening antigen and probed for both IgG and IgM antibodies using a Goat anti-IgG/IgM (H&L)-HRP secondary and developed with TMB substrate.

Positive cultures are retested on screening antigen to confirm secretion and on an irrelevant antigen (Human Transferrin). Clones of interest are isotyped by antibody trapping ELISA to determine if they are IgG or IgM isotype and can be tested by indirect ELISA on other peptide-BSA conjugates for example lacking try68.

Positive IgG-secreting clones are subjected to large-scale production.

Isotyping

The hybridoma antibodies are isotyped using antibody trap experiments. Trap plates are coated with 1:10,000 Goat anti-mouse IgG/IgM (H&L) antibody at 100 µL/well carbonate coating buffer pH9.6 overnight at 4 C. Primary antibody (hybridoma supernatants) is added at 100 µg/mL. Secondary Antibody is added at 1:5,000. Goat anti-mouse IgGγ-HRP or 1:10,000 Goat anti-mouse IgMµ-HRP is added at 100 µL/well in PBS-Tween for 1 hour at 37 C with shaking. All washing steps are performed for 30 mins with PBS-Tween. The substrate TMB is added at 50 µL/well, developed in the dark and stopped with equal volume 1M HCl.

Antibody-containing hybridoma tissue culture supernatants are typed for immunoglobulin type and screened against negative control peptide and BSA. IgG producing clones that do not bind the negative control peptide or BSA are tested by ELISA for binding to the peptide DAGWGNL (SEQ ID NO: 1).

Example 6

Rabbit Monoclonal Antibody Production

The DAGWGNL (SEQ ID NO: 1) peptide conjugated to KLH via a C-terminal cysteine (Peptide-KLH) was used for rabbit immunization for generation of B cells secreting monoclonal antibodies specific to the TDP-43 peptide. Based on indirect ELISA testing of the isolated B cells, B cells were selected for RNA isolation and generation of recombinant plasmid DNA. Functional, antigen-binding recombinant mAbs were be transfected and expressed for generation of purified mAb.

Immunization:

Two sets of rabbits were immunized simultaneously: one set by Fast Rabbit (28-day) immunization and one set by Standard Rabbit (78-day) immunization.

Fast Rabbit immunization: 2×New Zealand White (NZB) rabbits were immunized by subcutaneous injection (SC) with 200 µg of Peptide-KLH. At 7 and 14 days post immunization, the rabbits received $1^{st}$ and $2^{nd}$ boost injections (SC) with 100 µg of Peptide-KLH. At 21 days, test bleeding was conducted and sera was titrated by indirect ELISA probing for IgG. At 28 days, rabbits were exsanguinated for heparinized whole blood collection and downstream rabbit monoclonal antibody development. Appropriate titre is >0.300 OD at 1:64,000 dilution.

Standard Rabbit immunization: 2×New Zealand White (NZB) rabbits were immunized by subcutaneous injection (SC) with 250 µg of Peptide-KLH. At 28 and 47 days post immunization, the rabbits received 1st and 2nd boost injections (SC) with 250 µg of Peptide-KLH. At 58 days, test bleeding was conducted and sera was titrated by indirect ELISA probing for IgG. A third boost was administered (SC) at 66 days with 250 µg of Peptide-KLH. At 78 days, rabbits were exsanguinated for heparinized whole blood collection and downstream rabbit monoclonal antibody development. Appropriate titre is >0.300 OD at 1:64,000 dilution. Day number may fluctuate by +/−1-2 days.

B Cell Isolation, Enrichment and Screening-14 Days

In vitro Culture of B Cells—7 days: B cells from the rabbit(s) were isolated from the whole heparinized blood and cultured. Bio-panning was performed using the TDP43 peptide. Antigen-specific B-cells were subsequently plated for further culture and screening.

Antibody Analysis (Screening)—7 days: B cell culture supernatants from the plates were tested against BSA-conjugated TDP43 linear peptide by indirect ELISA. This was probed with a secondary antibody against rabbit IgG antibody. The top responding antigen-specific B cells were transferred to new plates. Clone supernatants were then titrated by indirect ELISA on BSA-conjugated TDP43 linear peptide and trap to rank the top clone selection.

Example 7

Monoclonal Antibody Cloning and Sequencing

Mouse mAb Cloning

Variable regions of the heavy and light chain immuno-globulin gene for several mouse hybridoma clones were identified and sequenced.

Method

Total RNA was isolated from the hybridoma cells and reverse-transcribed into cDNA using either isotype-specific anti-sense primers or universal primers. Antibody fragments of heavy chain and light chain were amplified by rapid amplification of cDNA ends (RACE). Amplified antibody fragments were cloned into a standard cloning vector separately. Colony PCR was performed to screen for clones with inserts of correct sizes. Per hybridoma cell line, 5 clones were selected and sequenced for both heavy and light chains. Sequence alignment was performed with the 5 clones to confidently determine the heavy and light chain sequences for each monoclonal antibody.

Sequences are shown in Tables 2, 3 and 4 below, with CDR1, CDR2 and CDR3 regions of heavy and light chains shown as underlined and bolded in Tables 3 and 4.

Rabbit mAb Cloning

Cloning-14 days: For the top clones, antibody RNA isolation and generation of recombinant plasmid DNA was performed. For each top clone, heavy and light chain variable regions were cloned into separate mammalian expression vectors, containing the rabbit heavy and kappa constant regions.

Expression-14 days: Heavy and light chain vectors were cotransfected into mammalian cells for small-scale transfection. Superatant was screened by indirect ELISA on BSA-conjugated TDP43 peptide to confirm functional, recombinant mAbs were generated.

Purification: Top recombinant mAbs (DNA construct containing one heavy and one light chain) were sequenced, as shown in Tables 2, 3 and 4 below, with CDR1, CDR2 and CDR3 regions of heavy and light chains shown as underlined and bolded in Tables 3 and 4. Additional mAbs were sequenced, having SEQ ID NOs: 52-75, 90-97, and 112-119.

TABLE 2

Complementarity determining region (CDR) sequences

| Clone | CDR | Amino acid sequence | SEQ ID NO: | CDR | Amino acid sequence | SEQ ID NO: |
|---|---|---|---|---|---|---|
| 1 | H1 | GFSLSRYY | 10 | L1 | ESVYNNNH | 13 |
|  | H2 | IIPGGTT | 11 | L2 | EAS | 14 |
|  | H3 | AGGPTGNSHFTL | 12 | L3 | SGYKRVTTDGIA | 15 |
| 14 | H1 | GFSFSSNYV | 16 | L1 | ESVYSNNR | 19 |
|  | H2 | IWFAGIVDTT | 17 | L2 | YAS | 20 |
|  | H3 | ARNPVGSVNL | 18 | L3 | AGWRGARTDGVD | 21 |
| 17 | H1 | GFSFSSSYV | 22 | L1 | QSVYKNNY | 25 |
|  | H2 | SDTGINT | 23 | L2 | KAS | 26 |
|  | H3 | ARRYTGDTYLGNFNL | 24 | L3 | AGGWRSLNA | 27 |
| 20 | H1 | EFSFSSRYW | 28 | L1 | QSIHKNNY | 31 |
|  | H2 | IYTGSIDAT | 29 | L2 | FAS | 32 |
|  | H3 | VRGSDAWGLYFNL | 30 | L3 | AGVYSGRIFA | 33 |
| 30 | H1 | GFSLSSYT | 34 | L1 | QSVYKNR | 37 |
|  | H2 | IYGGIGST | 35 | L2 | GAS | 38 |
|  | H3 | GRGDI | 36 | L3 | LGNYDCSSVDCGA | 39 |
| 38 | H1 | GFSFSAYY | 40 | L1 | ESVYNNNQ | 43 |
|  | H2 | TIPIGRT | 41 | L2 | QAS | 44 |
|  | H3 | AGGPTGNSHFTL | 42 | L3 | AGYKSPTTDGIA | 45 |
| 36 | H1 | GFSLSSYA | 46 | L1 | QSVYKNNG | 49 |
|  | H2 | IYNYET | 47 | L2 | FTS | 50 |
|  | H3 | ARDIFRTNTNL | 48 | L3 | LGGYDCSSRVCGA | 51 |
| 28 | H1 | GFSLSSYN | 120 | L1 | QSVYNNNN | 123 |
|  | H2 | IGTGGIT | 121 | L2 | RAS | 124 |
|  | H3 | VRSSGSDWWFHI | 122 | L3 | QGYFSGFITT | 125 |
| 3E8 | H1 | GFTFSSYY | 130 | L1 | QSIVHSNGNTY | 133 |
|  | H2 | INSNGGST | 131 | L2 | KVS | 134 |
|  | H3 | VRQNYEGAY | 132 | L3 | FQSSHVPWT | 135 |
| 2F7 | H1 | GFTFSSYY | 130 | L1 | QSIVHSNGNTY | 133 |
|  | H2 | INSNGGST | 131 | L2 | KVS | 134 |
|  | H3 | VRQNYEGAY | 132 | L3 | FQSSHVPWT | 135 |
| 3F11 | H1 | GFTFSSYY | 140 | L1 | QSIVHSNGNTY | 143 |
|  | H2 | INTNGGST | 141 | L2 | KVS | 144 |
|  | H3 | VRQNYEGAY | 142 | L3 | FQSSHVPWT | 145 |

TABLE 3

DNA sequences of variable domain regions

| Clone | Isotype | DNA sequence | SEQ ID NO: |
|---|---|---|---|
| 1 | Heavy | CAGTCGGTGGAGGAGTCCGGGGGTCGCCTGGTCACGCCTGGGACACCCCTG ACACTCACCTGCACAGTCTCTGGATTCTCCCTCAGTAGGTACTACATGACCT GGGTCCGCCAGGCTCCAGGGAAGGGGCTGGAATACATCGGGGTCATTATTC CTGGTGGTACCACATACTACGCGAGCTGGGCGAAAGGCCGATTCACCATCTC CAAAACCTCGACCACGTGGATCTGAGAATCACCAGTCCGACAACCGAGGAC ACGGCCACTTATTTCTGTGCCGGAGGTCCTACTGGTAACAGCCACTTTACAT TGTGGGGCCAGGGCACCCTGGTCACCGTCTC | 76 |
|  | Light | GTGATGACCCAGACTCCATCTTCCAAGTCTGTCCCTGTGGGAGGCACAGTCA CCATCAATTGCCAGGCCAGTGAGAGTGTTTATAATAACAACCACTTATCCTG GTATCAGCAGAAATCAGGGCAGCCTCCCAAGCTCCTGATCTACGAAGCATCC AAACTGGAATCTGGGGTCCCACCGCGGTTCAAAGGCAGTGGATCTGGGACAC AGTTCACTCTCACCATCAGCGATGTGGTGTGTGACGATGCTGCCACTTACTAC TGTTCAGGATATAAACGTGTTACTACTGATGGTATTGCTTTCGGCGGAGGGA CCGAGGTGGTGGTCAAAG | 77 |
| 14 | Heavy | CAGGAGCAGCTGGAGGAGTCCGGGGGAGACCTGGTCAAGCCTGAGGGATCC CTGACACTCACCTGCACAGCCTCTGGATTCTCCTTCAGTAGCAACTACGTGA TGTGCTGGGTCCGCCAGGCTCCAGGGAAGGGGCTGGAGTGGGTCGCATGCA TTTGGTTTGCTGGTATTGTTGATACTACTTACTACGCGACCTGGGCGAAAGGC | 78 |

TABLE 3-continued

| | | DNA sequences of variable domain regions | |
|---|---|---|---|
| Clone | Isotype | DNA sequence | SEQ ID NO: |

| Clone | Isotype | DNA sequence | SEQ ID NO: |
|---|---|---|---|
| | Light | CGATTCACCATCTCCAAAACCTCGTCGACCACGGTGACTCTGCAAATGACCA GTCTGACAGCCGCGGACACGGCCACCTATTTCTGTGCGAGAAATCCTGTTGG TAGTGTGAACTTGTGTGGGGCCAGGGCACCCTGGTCACCGTCTC GTGATGACCCAGACTCCATCTTCCAAGTCTGTCCCTGTGGGAGGCTCAGTCA CCATCAATTGCCAGGCCAGTGAGAGTGTTTATAGTAACAACCGCTTATCCTG GTATCAGCAGAAACCAGGGCAGCCTCCTAAGCTCCTGATCTATTATGCATCCA CTCTGGAATCTGGGGTCCCATCGCGGTTCAAAGGCAGTGGATTTGGGACACA CTTCACTCTCACCATCAGCGGCGCGCAGTGTGACGATGCTGCCACTTACTAC TGTGCAGGATGGAGAGGTGCTAGGACTGATGGTGTAGATTTCGGCGGAGGG ACCGAGGTGGTGGTCAAAG | 79 |
| 17 | Heavy | CAGGAGCAGCTGGTGGAGTCCGGGGGAGGCCTGGTCCAGCCTGGGGCATC CCTGACACTCACCTGCACAGCCTCTGGATTCTCCTTCAGTAGCAGCTACGTGATGTGCTGGGTCCGCCAGGCTCCAGGGAAGGGGCTGGAATGGATCACATGC AGTGATACTGGTATTAACACATGGTACGCGAGCTGGGCGAAAGGCCGATTC ACCATCTCCAAAACCTCGTCGACCACGGTGACTCTGCAAATGACCAGTCTGA CAGCCGCGGACACGGCCACCTATTTCTGTGCGAGACGTTATACTGGCGATA CTTATTTGGGAAACTTTAACTTGTGGGGCCAGGGCACCCTGGTCACCGTCTC | 80 |
| | Light | GCCCAAGTGCTGACCCAGACTCCAGCCTCGGTGTCTGCAGCTGTGGGAGGC ACAGTCACCATCAACTGCCAGGCCAGTCAGAGTGTTTATAAGAACAACTACTTATCCTGGTATCAGCAGAAACCAGGGCAGCCTCCCAAGCTCCTGATCTACAA GGCTTCCACTCTGGCATCTGGGGTCCCATCGCGGTTCAAAGGCAGTGGATCT GGGACACAGTTCACTCTCACCATCAGCGACGTGCAGTGTGACGATGCTGCCA CTTACTACTGTGCAGGCGGTTGGCGTAGTCTAAATGCTTTCGGCGGAGGGAC CGAGGTGGTGGTCAAAG | 81 |
| 20 | Heavy | CAGGAGCAGCTGGAGGAGTCCGGGGGAGACCTGGTCAAGCCTGGGGCATC CCTGACACTCACCTGCACAGCCTCTGAATTCTCCTTCAGTAGTAGATACTGGGCATGCTGGGTCCGCCAGGCTCCAGGGAAGGGGCTGGAGTGGAGCGCATG CATTTATACTGGTAGTATTGATGCTACTTACTACGCGAGCTGGGCGAAAGGC CGATTCACCATCTCCAAAACCTCGTCGACCACGGTGACTCTGCAAGTGACCA GTCTGACAGCCGCGGACACGGCCACCTATTTCTGTGTGAGGGGGAGTGATG CCTGGGGTCTCTACTTTAACTTGTGGGGCCAGGGCACCCTGGTCACCGTCTC | 82 |
| | Light | TGCTGACCCAGACTCCATCCTCCGTGTCTGCAGCTGTGGGAGGCACAGTCAC CGTCAGTTGCCAGTCCAGTCAGAGTATTCATAAGAATAATTACTTAGCCTGG TATCAGCAGAAACCAGGGCAGCCTCCCAAGCTCCTGATCTATTTTGCATCCAC TCTGGCATCTGGGGTCCCATCGCGGTTCAAAGGCAGTGGATCTGGGACACAG TTCACTCTCACCATCAGTGACTGGAGTGTGACGATGCTGCCACTTACTACTG TGCAGGCGTTTATAGTGGTCGTATTTTTGCTTTCGGCGGAGGGACCGAGGTG GTGGTCAAAG | 83 |
| 30 | Heavy | CAGTCGGTGGAGGAGTCCGGGGGTCGCCTGGTCACGCCTGGGACACCCCTG ACACTCACCTGCAAAGTCTCTGGATTCTCCCTCAGTAGCTATACAATGATCTG GGTCCGCCAGGCTCCAGGGAAGGGGCTGGAGTGGATCGGGTACATTTATGG TGGTATTGGTAGCACATGGTACGCGAGCTGGGCGAAAGGCCGATTCACCAT CTCCAAAACCTCGACCACGGTGGATCTGAAAATCACCAGTCCGACAACCGAG GACACGGCCACCTATTTCTGTGGCAGAGGGGACATCTGGGGCCAGGGCACC CTGGTCACCGTCTC | 84 |
| | Light | GTGCTGACCCAGACTGCATCCCCCCGTGTCTGCGGCTGTGGGAGGCACAGTC ACCATCAATTGCCAGTCCAGTCAGAGTGTTTATAAGAACCGCTTATCCTGGTA TCAGCAGAAACCAGGGCAGTCTCCCAAGCGCCTGATCTATGGTGCATCCACT CTGGAATCTGGGGTCCCATCGCGGTTCAAAGGCAGCGGATCTGGGACGCAG TTCACTCTCACCATCAGCGACGTGCAGTGTGACGATGCTGCCACTTACTACTG TCTAGGCAATTATGATTGTAGTAGTGTTGATTGTGGTGCTTTCGGCGGAGGG ACCGAGGTGGTGGTCAAAG | 85 |
| 38 | Heavy | CAGTCGGTGGAGGAGTCCGGGGGTCGCCTGGTCACGCCTGGGACACCCCTG ACACTCACCTGCACAGTCTCTGGATTCTCCTTCAGTGCCTACTACATGACCTG GGTCCGCCAGGCTCCAGGGAAGGGGCTGGAATTCATCGGAGTCACTATACC TATTGGCCGCACGTACTACGCGAGCTGGGCGAAAGGCCGATTCACCATCTCC AAAACCTCGACCACGGTGCATCTGAAAATCACCAGTCCGACAACCGAGGACA CGGCCGCTTATTTCTGTGCCGGAGGTCCTACTGGTAATAGCCACTTTACATT GTGGGGCCAGGGCACCCTGGTCACCGTCTC | 86 |
| | Light | GTGATGACCCAGACTCCATCTTCCAAGTCTGTCCCTGTGGGAGACACAGTTA CCATCAATTGCCAGGCCAGTGAGAGTGTTTATAATAACAACCAATTATCCTG GTATCAGCAGAAACCAGGGCAGCCTCCCAAGCTCCTGATCTACCAGGCATCC AAACTGGAATCTGGGGTCCCATCGCGGTTCAAAGGCAGTGGATCTGGGACAC AGTTCACTCTCACCATCAGCGATGTGGTGTGTGACGATGCTGCCACTTACTAC TGTGCAGGATATAAAAGTCCTACTACTGATGGTATTGCTTTTCGGCGGAGGGA CCGAGGTGGTGGTCAAAG | 87 |
| 36 | Heavy | CAGTCGGTGGAGGAGTCCGGGGGTCGCCTGGTCACGCCTGGGACACCCCTG ACACTCACCTGCACAGTCTCTGGATTCTCCCTCAGTAGCTATGCAATGAGCT GGGTCCGCCAGGCTCCAGGGAAGGGGCTGGAATGGATCGGATTCATTTATA ATTATGAAACATACTACGCGAACTGGGCGAAAGGCCGATTCACCATCTCCAA | 88 |

TABLE 3-continued

DNA sequences of variable domain regions

| Clone | Isotype | DNA sequence | SEQ ID NO: |
|---|---|---|---|
| | Light | AACCTCGACCTCGGTGGTTCTGAAAATCACCAGTCCGACAACCGACGACACG GCCACCTATTTCTGTGCCAGAGATATTTTTCGTACTAATACTAACTTGTGGGG CCAGGGCACCCTGGTCACCGTCTC | |
| | | GTGCTGACCCAGACTGCATCGCCCGTGTCTGCAGTTGTGGGAAGCACAGTCA CCATCAATTGCCAGGCCAGTCAGAGTGTTTATAAGAACAACGGCTTATCCTG GTATCAGCAGAAACCAGGGCAGCCTCCCAAAGGCCTGATCTCTTTTACATCG ACTCTGGCATCTGGGGTCTCATCGCGGTTCAAAGGCAGTGGATCTGGGACAC AGTTTACTCTCACCATCAGCGACGTGCAGTGTGACGATGCTGCCACTTACTAC TGTCTAGGCGGTTATGATTGTAGTAGTCGTGTTTGTGGTGCTTTCGGCGGAG GGACCGAGGTGGTGGTCAAAG | 89 |
| 28 | Heavy | CAGTCGCTGGAGGAGTCCGGGGGTCGCCTGGTCACGCCTGGGACACCCCTG ACACTCACCTGCACAGTCTCTGGGATTCTCCCTCAGTAGCTACAACATGGGCT GGGTCCGCCAGGCTCCAGGGGAGGGGCTGGAGTGGATCGGAGTCATTGGT ACTGGTGGTATCACACACTACGCGACCTGGGCAAAAGGCCGAGTCGCCATC TCCAGAACCTCGACCACGGTGGGTCTGCGAATGACCAGTCCGACAACCGAG GACACGGCCACCTATTTCTGTGTCAGATCTAGTGGTAGTGATTGGTGGTTTC ACATCTGGGGCCAGGGCACCCTGGTCACCGTCTC | 126 |
| | Light | GTGCTGACCCAGACTACATCGCCCGTGTCTGCAGCTGTGGGAGGCACAGTCA CCATCAGTTGCCAGTCCAGTCAGAGTGTTTATAATAACAACAACTTAGCCTG GTTTCAGCAGAAACCAGGGCAGCCTCCCAAGCTCCTGATCTACAGGGCATCC AATCTGCCATCTGGTGTCCCATCGCGGTTCAGAGGCAGTGGATCTGGGTCAC AGTTCACTCTCACAATCAGCGAAGTACAGTGTGACGATGCTGCCACTTACTAC TGTCAAGGCTATTTTAGTGGATTTATCACTACTTTCGGCGGAGGGACCGAGG TGGTGGTCAAAG | 127 |
| 3E8 | Heavy | GACGTGAAGCTCGTGGAGTCTGGGGGAGGCTTAGTGAAGCTTGGA GGGTCCCTGAAACTCTCCTGTGCAGCCTCTGGATTCACTTTCAGTAGCTATT ACATGTCTTGGGTTCGCCAGACTCCAGAGAAGAGGCTGGAGTTGGTCGCA ACCATTAATAGTAATGGTGGTAGCACCTACTATCCAGACACTGTGAAGGGCC GAATCACCATCTCCAGAGACAATGCCAAGAACACCCTGCAGTTGCAAATGA GCAGTCTGAGGTCTGAGGACACAGCCTTGTATTACTGTGTAAGACAAAACT ACGAGGGGGCTTACTGGGGCCAAGGGACTCTGGTCACTGTCTCTGCA | 136 |
| | Light | GATGTTTTGATGACCCAAACTCCACTCTCCCTGCCTGTCACTCTTGGAGATCA AGCCTCCATCTCTTGCAGATCTAGTCAGAGCATTGTACATAGTAATGGAAAC ACCTATTTAGAATGGTACCTGCAGAAACCAGGCCAGTCTCCAAAGCTCCTGAT CTACAAAGTTTCCAACCGATTTTCTGGGGTCCCAGACAGGTTCAGTGGCAGT GGATCAGGGACAGATTTCACACTCAAGATCAGCAGAGTGGAGGCTGAGGATC TGGGAGTTTATTACTGCTTTCAAAGTTCACATGTTCCGTGGACGTTCGGTGGA GGCACCAAGCTGGAAATCAAA | 137 |
| 2F7 | Heavy | GACGTGAAGCTCGTGGAGTCTGGGGGAGGCTTAGTGAAGCTTGGA GGGTCCCTGAAACTCTCCTGTGCAGCCTCTGGATTCACTTTCAGTAGCTATT ACATGTCTTGGGTTCGCCAGACTCCAGAGAAGAGGCTGGAGTTGGTCGCA ACCATTAATAGTAATGGTGGTAGCACCTACTATCCAGACACTGTGAAGGGCC GAATCACCATCTCCAGAGACAATGCCAAGAACACCCTGCAGTTGCAAATGA GCAGTCTGAGGTCTGAGGACACAGCCTTGTATTACTGTGTAAGACAAAACT ACGAGGGGGCTTACTGGGGCCAAGGGACTCTGGTCACTGTCTCTGCA | 136 |
| | Light | GATGTTTTGATGACCCAAACTCCACTCTCCCTGCCTGTCACTCTTGGAGATCA AGCCTCCATCTCTTGCAGATCTAGTCAGAGCATTGTACATAGTAATGGAAAC ACCTATTTAGAATGGTACCTGCAGAAACCAGGCCAGTCTCCAAAGCTCCTGAT CTACAAAGTTTCCAACCGATTTTCTGGGGTCCCAGACAGGTTCAGTGGCAGT GGATCAGGGACAGATTTCACACTCAAGATCAGCAGAGTGGAGGCTGAGGATC TGGGAGTTTATTACTGCTTTCAAAGTTCACATGTTCCGTGGACGTTCGGTGGA GGCACCAAGCTGGAAATCAAA | 137 |
| 3F11 | Heavy | GACGTGAAGCTCGTGGAGTCTGGGGGAGACTTAGTGAAGCTTGGAGGGTCC CTGAAACTCTCCTGTGCAGCCTCTGGATTCACTTTCAGTAGCTATTACATGTC TTGGGTTCGCCAGACTCCAGAGAAGAGGCTGGAGTTGGTCGCAGTATTAAT ACTAATGGTGGTAGCACCTACTATCCAGACACTGTGAAGGGCCGATTCACCA TCTCCAGAGACAATGCCAAGAACACCCTGTACCTGCAAATGAGCAGTCTGAA GTCTGAGGACACAGCCTTGTATTACTGTGTAAGACAAAACTACGAGGGGGCT TACTGGGGCCAAGGGACTCTGGTCACTGTCTCTGCA | 146 |
| | Light | GATGTTTTGATGACCCAAACTCCACTCTCCCTGCCTGTCAGTCTTGGAGATCA AGCCTCCATCTCTTGCAGATCTAGTCAGAGCATTGTACATAGTAATGGAAAC ACCTATTTAGAATGGTACCTGCAGAAACCAGGCCAGTCTCCAAAGCTCCTGAT CTACAAAGTTTCCAACCGATTTTCTGGGGTCCCAGACAGGTTCAGTGGCAGT GGATCAGGGACAGATTTCACACTCAAGATCAGCAGAGTGGAGGCTGAGGATC TGGGAGTTTATTACTGCTTTCAAAGTTCACATGTTCCGTGGACGTTCGGTGGA GGCACCAAGCTGGAAATCAAA | 147 |

TABLE 4

Amino acid sequences of variable domain regions

| Clone | Isotype | Amino acid sequence | SEQ ID NO: |
|---|---|---|---|
| 1 | Heavy | QSVEESGGRLVTPGTPLTLTCTVSGFSLSRYYMTWVRQAPGKGLEYIGVIIPGGTTYYASWAKGRFTISKTSTTVDLRITSPTTEDTATYFCAGGPTGNSHFTLWGQGTLVTVS | 98 |
|  | Light | VMTQTPSSKSVPVGGTVTINCQASESVYNNNHLSWYQQKSGQPPKLLIYEASKLESGVPPRFKGSGSGTQFTLTISDVVCDDAATYYCSGYKRVTTDGIAFGGGTEVVVK | 99 |
| 14 | Heavy | QEQLEESGGDLVKPEGSLTLTCTASGFSFSSNYVMCWVRQAPGKGLEWVACIWFAGIVDTTYYATWAKGRFTISKTSSTTVTLQMTSLTAADTATYFCARNPVGSVNLWGQGTLVTVS | 100 |
|  | Light | VMTQTPSSKSVPVGGSVTINCQASESVYSNNRLSWYQQKPGQPPKLLIYYASTLESGVPSRFKGSGFGTHFTLTISGAQCDDAATYYCAGWRGARTDGVDFGGGTEVVVK | 101 |
| 17 | Heavy | QEQLVESGGGLVQPGASLTLTCTASGFSFSSSYVMCWVRQAPGKGLEWITCSDTGINTWYASWAKGRFTISKTSSTTVTLQMTSLTAADTATYFCARRYTGDTYLGNFNLWGQGTLVTVS | 102 |
|  | Light | AQVLTQTPASVSAAVGGTVTINCQASQSVYKNNYLSWYQQKPGQPPKLLIYKASTLASGVPSRFKGSGSGTQFTLTISDVQCDDAATYYCAGGWRSLNAFGGGTEVVVK | 103 |
| 20 | Heavy | QEQLEESGGDLVKPGASLTLTCTASEFSFSSRYWACWVRQAPGKGLEWSACIYTGSIDATYYASWAKGRFTISKTSSTTVTLQVTSLTAADTATYFCVRGSDAWGLYFNLWGQGTLVTVS | 104 |
|  | Light | LTQTPSSVSAAVGGTVTVSCQSSQSIHKNNYLAWYQQKPGQPPKLLIYFASTLASGVPSRFKGSGSGTQFTLTISDLECDDAATYYCAGVYSGRIFAFGGGTEVVVK | 105 |
| 30 | Heavy | QSVEESGGRLVTPGTPLTLTCKVSGFSLSSYTMIWVRQAPGKGLEWIGYIYGGIGSTWYASWAKGRFTISKTSTTVDLKITSPTTEDTATYFCGRGDIWGQGTLVTVS | 106 |
|  | Light | VLTQTASPVSAAVGGTVTINCQSSQSVYKNRLSWYQQKPGQSPKRLIYGASTLESGVPSRFKGSGSGTQFTLTISDVQCDDAATYYCLGNYDCSSVDCGAFGGGTEVVVK | 107 |
| 38 | Heavy | QSVEESGGRLVTPGTPLTLTCTVSGFSFSAYYMTWVRQAPGKGLEFIGVTIPIGRTYYASWAKGRFTISKTSTTVHLKITSPTTEDTAAYFCAGGPTGNSHFTLWGQGTLVTVS | 108 |
|  | Light | VMTQTPSSKSVPVGDTVTINCQASESVYNNNQLSWYQQKPGQPPKLLIYQASKLESGVPSRFKGSGSGTQFTLTISDVVCDDAATYYCAGYKSPTTDGIAFGGGTEVVVK | 109 |
| 36 | Heavy | QSVEESGGRLVTPGTPLTLTCTVSGFSLSSYAMSWVRQAPGKGLEWIGFIYNYETYYANWAKGRFTISKTSTSVVLKITSPTTDDTATYFCARDIFRTNTNLWGQGTLVTVS | 110 |
|  | Light | VLTQTASPVSAVVGSTVTINCQASQSVYKNNGLSWYQQKPGQPPKGLISFTSTLASGVSSRFKGSGSGTQFTLTISDVQCDDAATYYCLGGYDCSSRVCGAFGGGTEVVVK | 111 |
| 28 | Heavy | QSLEESGGRLVTPGTPLTLTCTVSGFSLSSYNMGWVRQAPGEGLEWIGVIGTGGITHYATWAKGRVAISRTSTTVGLRMTSPTTEDTATYFCVRSSGSDWWFHIWGQGTLVTVS | 128 |
|  | Light | VLTQTTSPVSAAVGGTVTISCQSSQSVYNNNNLAWFQQKPGQPPKLLIYRASNLPSGVPSRFRGSGSGSQFTLTISEVQCDDAATYYCQGYFSGFITTFGGGTEVVVK | 129 |
| 3E8 | Heavy | DVKLVESGGGLVKLGGSLKLSCAASGFTFSSYYMSWVRQTPEKRLELVATINSNGGSTYYPDTVKGRITISRDNAKNTLQLQMSSLRSEDTALYYCVRQNYEGAYWGQGTLVTVSA | 138 |
|  | Light | DVLMTQTPLSLPVTLGDQASISCRSSQSIVHSNGNTYLEWYLQKPGQSPKLLIYKVSNRFSGVPDRFSGSGSGTDFTLKISRVEAEDLGVYYCFQSSHVPWTFGGGTKLEIK | 139 |
| 2F7 | Heavy | DVKLVESGGGLVKLGGSLKLSCAASGFTFSSYYMSWVRQTPEKRLELVATINSNGGSTYYPDTVKGRITISRDNAKNTLQLQMSSLRSEDTALYYCVRQNYEGAYWGQGTLVTVSA | 138 |
|  | Light | DVLMTQTPLSLPVTLGDQASISCRSSQSIVHSNGNTYLEWYLQKPGQSPKLLIYKVSNRFSGVPDRFSGSGSGTDFTLKISRVEAEDLGVYYCFQSSHVPWTFGGGTKLEIK | 139 |
| 3F11 | Heavy | DVKLVESGGDLVKLGGSLKLSCAASGFTFSSYYMSWVRQTPEKRLELVAVINTNGGSTYYPDTVKGRFTISRDNAKNTLYLQMSSLKSEDTALYYCVRQNYEGAYWGQGTLVTVSA | 148 |
|  | Light | DVLMTQTPLSLPVSLGDQASISCRSSQSIVHSNGNTYLEWYLQKPGQSPKLLIYKVSNRFSGVPDRFSGSGSGTDFTLKISRVEAEDLGVYYCFQSSHVPWTFGGGTKLEIK | 149 |

Example 8

Direct Binding Assays

Binding of antisera, hybridoma supernatants or purified antibodies to peptides (conjugated to BSA) can be examined by surface plasmon resonance using a Biacore™ 3000 instrument (GE Healthcare).

Binding analysis is carried out using a high density (at least 1000 response units (RU)) of antigen immobilized on flow cells. Dilutions of a selected clone are sequentially injected over the surface to assess binding.

For affinity kinetics and specificity analysis, a peptide comprising DAQWGNL (SEQ ID NO: 1) or GWG and conjugated to BSA, is immobilized at low densities (50-100 RU) on adjacent flow cells. Serial 2-fold dilutions of a selected clone (4.7 nM to 75 nM) are then sequentially injected over the surfaces at 60 µl/minute for 3 minutes, followed by a dissociation phase. Following a double-reference subtraction, the sensorgrams are fitted to a Langmuir 1:1 binding model. Up to three separate analyses are performed on 3 consecutive days using the same sensorchip and the same conditions.

Binding analysis can also be carried out also using Molecular Affinity Screening System (MASS-2) (Sierra Sensors GmbH, Hamburg, Germany). MASS-2 is a Surface Plasmon Resonance (SPR) Imaging analytical biosensor that employs high intensity laser light and high speed optical scanning to monitor binding interactions in real time. The peptide-BSA conjugates are covalently immobilized on separate flow cells of a High Amine Capacity (HAC) sensor chip, using standard amine-coupling chemistry, and unreacted sites blocked. Adjacent flow cells are similarly immobilized with BSA as a reference control surface.

Binding Kinetics of Monoclonal Antibodies

Surface plasmon resonance (SPR) analysis was used to measure the binding kinetics of monoclonal antibodies to the peptide epitope. Peptide conjugated to bovine serum albumin (BSA) was immobilized at a very low density (approximately 50 RUs) on flow cells of a sensor chip. Purified mouse or rabbit monoclonal antibodies diluted 4-fold from 31.25 nM to 0.24 nM were injected sequentially over the surfaces for approximately 5 min followed by dissociation in buffer and surface regeneration. Binding parameters were calculated using kinetic curve fitting and a Langmuir 1:1 interaction model. Both mouse and rabbit monoclonal antibodies showed high subnanomolar affinity for the peptide epitope, as shown in FIGS. 3A to 3E and in Table 5 below. Rabbit monoclonal antibodies showed greater affinity ($10^{-11}$ nM range) compared to mouse monoclonal antibodies ($10^{-10}$ nM range).

TABLE 5

| Binding kinetics of monoclonal antibodies | | | |
|---|---|---|---|
| mAb | $k_{ON}$ ($M^{-1}s^{-1}$) | $k_{OFF}$ ($s^{-1}$) | $K_D$ (M) |
| Mouse 2F7 | 2.83E+06 | 1.76E-03 | 6.22E-10 |
| Mouse 3E8 | 2.77E+06 | 2.00E-03 | 7.22E-10 |
| Rabbit 1 | 4.03E+05 | 2.50E-05 | 6.20E-11 |
| Rabbit 17 | 4.70E+05 | 4.32E-05 | 9.19E-11 |
| Rabbit 14 | 5.99E+05 | 9.04E-06 | 1.51E-11 |

Example 9

Figure 4:
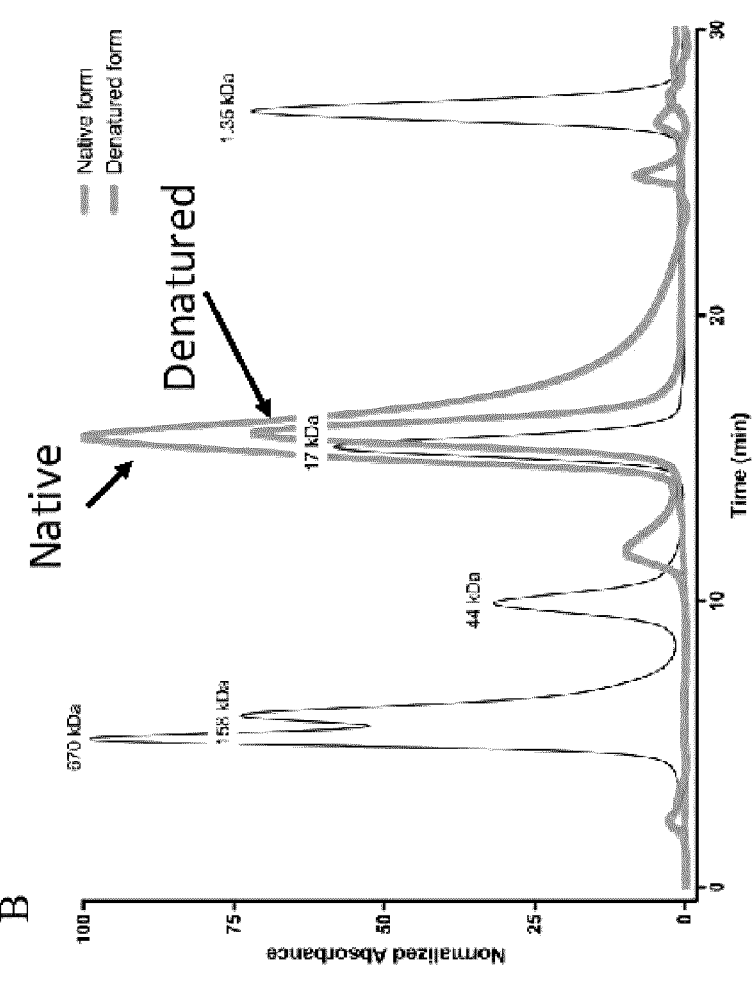
FIGS. 4A and 4B show recognition of the epitope by antibody in denatured but not natively folded TDP43 N-terminal domain.
Figure 4:
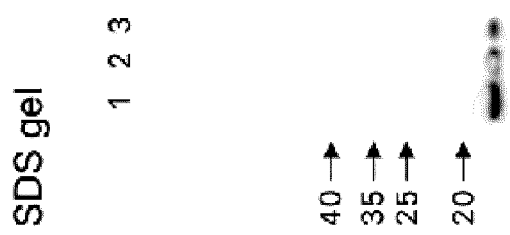
Figure 4:
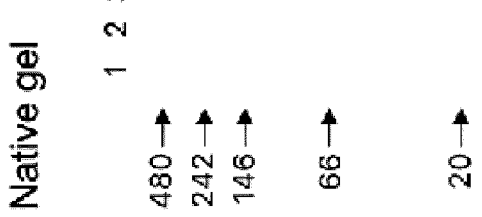

Epitope Recognized by Antibody in Denatured but not Natively Folded TDP N-Terminal Domain The N-terminal domain of TDP-43 (residues 1-80) was expressed from plasmid in *Escherichia coli* and purified as described previously (Wang et al. 2018 EMBO). Purified TDP-43 NTD was dialyzed against PBS, concentrated to 0.5 mg/ml, and stored at −80° C. For Western blot analysis, native-PAGE was carried out using the Novex Bis-Tris system according to the manufacturer's specifications. Protein samples were mixed with the NativePAGE™ Sample Buffer. Pre-cast NativePAGE™ 4-16% Bis-Tris gel was run at 4° C. at 150 V constant for 60 min, then at 250 V for 30 min. Denaturing SDS-PAGE was carried out using the Novex Bis-Tris system according to the manufacturer's specifications. Protein samples were mixed with the NuPAGE™ LDS Sample Buffer. Pre-cast NuPAGE™ 4-12% Bis-Tris gel was run at RT at 200 V constant for 35 min. Proteins were then blotted onto PVDF (Thermo Fisher Scientific, USA) membranes using the XCell II Blot Module (Invitrogen, USA) following the manufacturer's protocol. Blots were blocked in 5% milk powder in TBST, and then were incubated with purified rabbit polyclonal antibody GS240 overnight at 4° C. For detection on the ChemiDoc MP (Biorad, USA), a donkey anti-Rabbit IgG HRP-labelled secondary antibodies (GE Healthcare Life Sciences, USA) was used. The SuperSignal West Femto (Thermo Scientific, USA) substrate was used according to the manufacturer's instructions. As shown in FIG. 4A, the antibody only recognized and stained denatured TDP-43 NTD on the SDS-PAGE gel, and not TDP-43 NTD on the native PAGE gel thereby confirming that the epitope is not accessible in natively folded TDP-43 and only becomes exposed upon misfolding (lanes 1, 2, 3 contain 0.6, 0.3, 0.15 ug/lane, respectively). Size exclusion chromatography (SEC) (FIG. 4B) shows that TDP-43 NTD in native form or denatured form remains monomeric. Molecular weight markers are superimposed for reference. SEC was performed using high performance liquid chromatography instrument on a Superdex 75 (10/300) HPLC column (GE Healthcare Life Sciences, USA). TDP-43 NTD (0.5 mg/ml) was denatured by incubation in 6 M Guanidine-HCl, 50 mM Tris-HCl buffer (pH 7.5.), 150 mM NaCl, 20 mM DTT, for 10 min at 37° C. The protein sample obtained (100 µl) was loaded onto the column pre-equilibrated with the same buffer and eluted at 0.5 ml/min. Native form was loaded onto the column pre-equilibrated with the 1x PBS buffer containing 5 mM DTT and eluted at 0.5 ml/min.

Example 10

Immunohistochemistry of Patient Samples

Brain and spinal cord samples were obtained from The Netherlands Brain Bank and were processed and stained at the Netherlands Institute for Neuroscience (Amsterdam, The Netherlands). Sections (8 UM thick) from formalin-fixed, paraffin-embedded tissue were mounted on Superfrost plus tissue slides (Menzel-Glaser, Germany) and dried overnight at 37° C. Sections were deparaffinized and subsequently immersed in 0.3% $H_2O_2$ in phosphate-buffered saline (PBS) for 30 min to quench endogenous peroxidase activity. Formalin fixation forms protein cross-links that could mask antigenic sites in tissue specimens. To break protein cross-links, slides were pre-treated with heat and Tris-EDTA (pH 9). Primary test antibodies were diluted in antibody diluent (Sigma) and incubated overnight at 4° C. at a dilution of 1:4000 (rabbit polyclonal GS240 antibody, 3E8 mouse monoclonal antibody) or 1:2000 (mouse monoclonal antibodies 3F11 and 2F7). Secondary EnVision HRP-conjugated goat anti-rabbit/mouse antibody (EV-GaM HRP, DAKO) was added for 30 min at room temperature followed by the chromogen 3,3,-Diaminobenzidine (DAKO) for 10 minutes. Sections were counterstained with haematoxylin to visualize the nuclei of the cells, dehydrated and mounted using Quick-D mounting medium (Klinipath).

Figure 5:
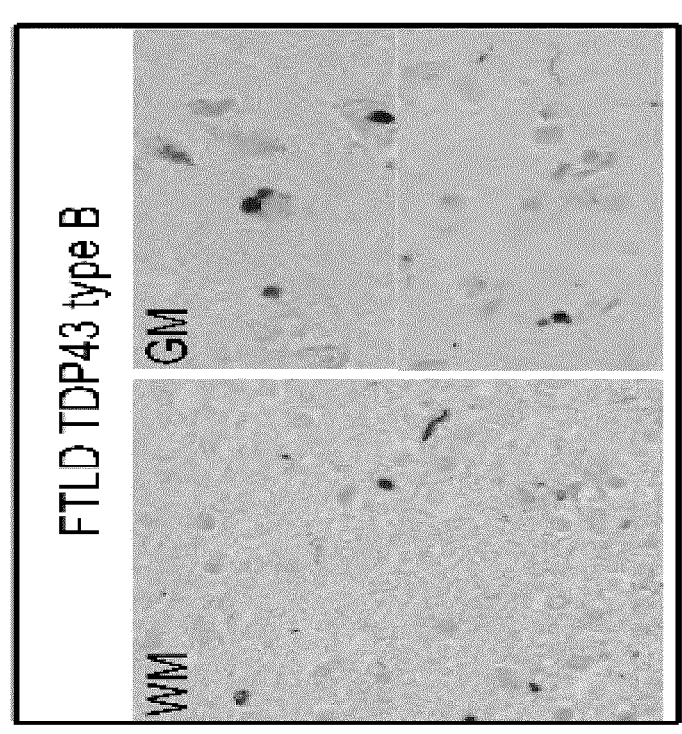
FIGS. 5A and 5B are images showing staining of sections from FTD brain (5A) and ALS spinal cord (5B) by rabbit polyclonal GS240 antibody.
FIGS. 5C-5E are images showing staining of sections from FTD brain by mouse monoclonal antibodies.
Figure 5:
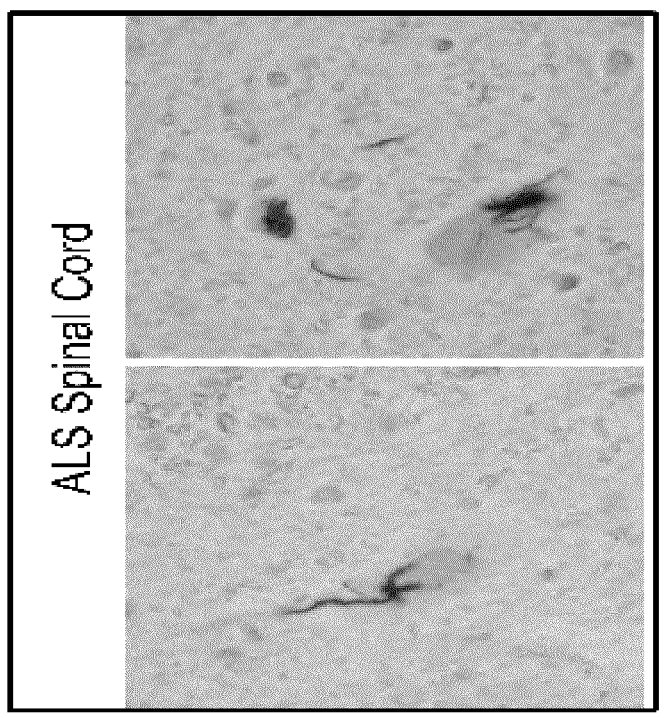
Figure 5:
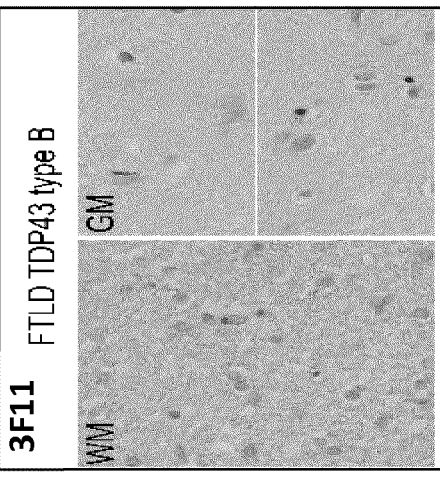
Figure 5:
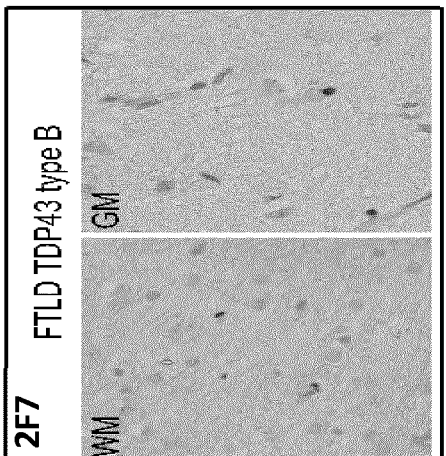
Figure 5:
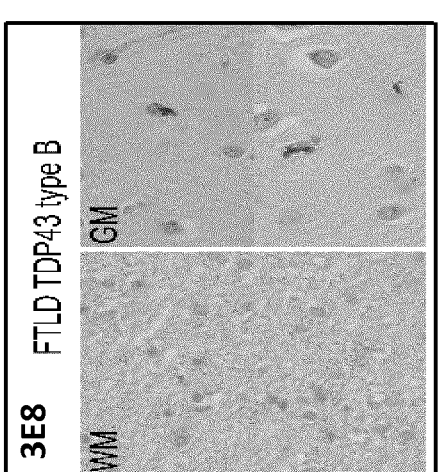

Staining of brain sections from a frontotemporal lobar degeneration (FTLD) type B patient is shown in FIGS. 5A, 5C, 5D and 5E. As shown in FIG. 5A, the rabbit polyclonal GS240 antibody shows staining of pathologic TDP43 in both white matter (WM) and grey matter (GM). The 3F11 (FIG. 5C) and 3E8 (FIG. 5E) monoclonal antibodies primarily detect pathologic TDP-43 in GM while the 2F7 monoclonal antibody (FIG. 5D) shows staining in both WM and GM. The rabbit polyclonal GS240 antibody was also tested on ALS spinal cord sections (FIG. 5B) and showed positivity in motor neurons and surrounding tissues. These results indicate that the antibodies are able to recognize epitopes of pathogenic TDP-43 as presented in situ in diseased tissues.

Example 11

Figure 6:
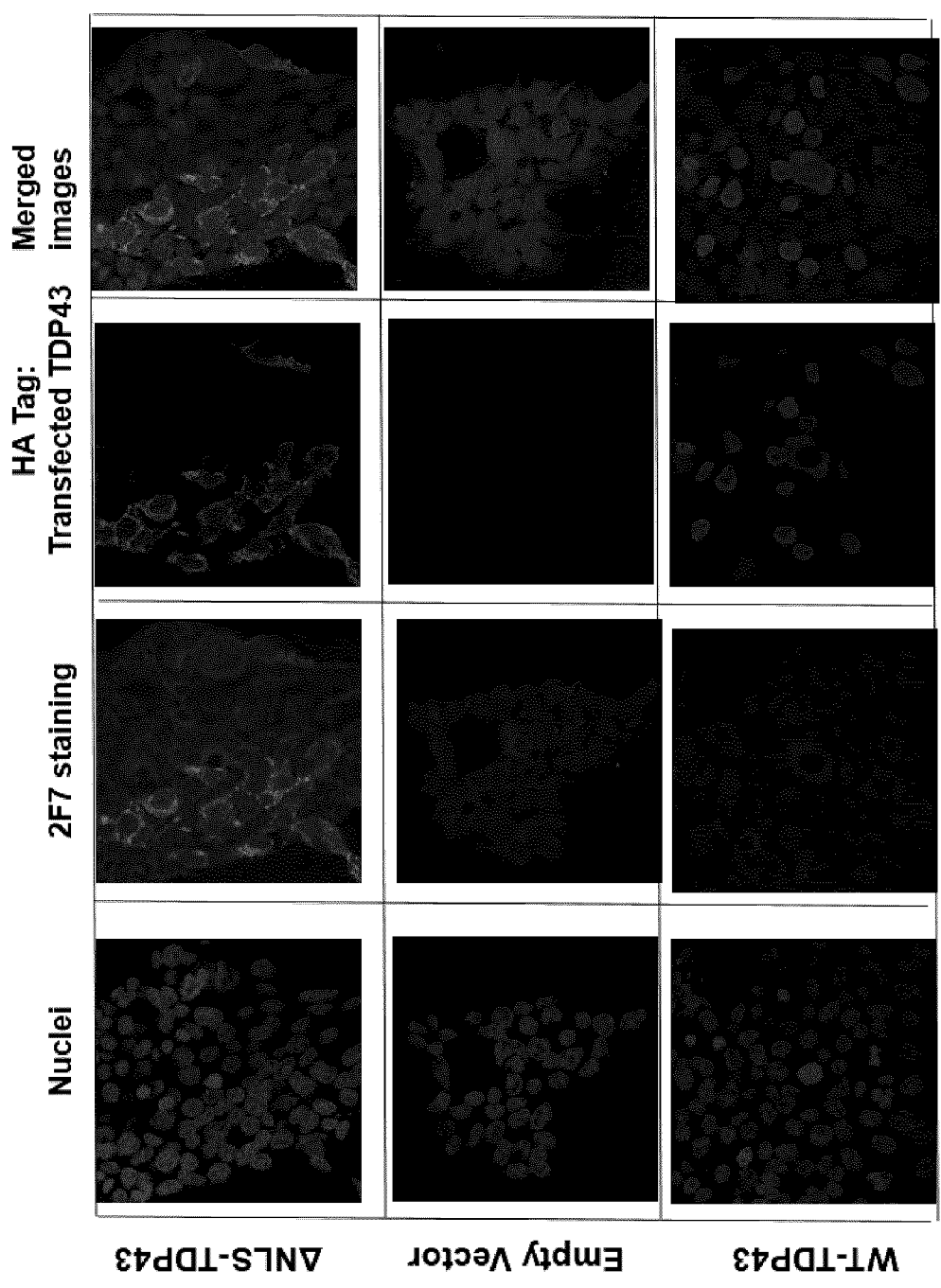
FIG. 6 is a series of images showing co-localization of mouse monoclonal Ab 2F7 staining with cytoplasmic TDP43 aggregates in ΔNLS-TDP43-HA transfected cells, but not WT nuclear TDP-43-HA.

Representative Staining of Transfected HEK293 Cells by Monoclonal Anti-TDP43 Antibody Mouse and rabbit monoclonal antibodies were tested for selective binding to misfolded TDP-43 in a cell transfection assay using immunohistochemistry as described in Example 4. Briefly, HEK293FT cells were transfected with plasmid encoding either HA-tagged ΔNLS-TDP43 (which forms cytoplasmic aggregates) or HA-tagged wild type (WT) TDP-43 (expressed in the nucleus) or empty vector. The anti-TDP-43 antibodies were diluted to 10 μg/ml for staining and fluorescently-labeled anti-rabbit IgG or anti-mouse IgG were used as secondary antibodies for detection. A chicken anti-HA tag antibody followed by a fluorescently labeled anti-chicken secondary antibody was used for detection of transfected TDP-43. Representative results obtained with the 2F7 mouse monoclonal antibody are shown in FIG. 6. Transfected ΔNLS-TDP43 mislocalizes to the cytoplasm where it forms aggregates that are readily detected by staining with the anti-HA tag antibody. The 2F7 antibody recognized the same aggregates as confirmed by co-localization of the 2 staining signals in the merged images. In contrast, transfected WT TDP43, which is detected in the nucleus by the HA tag antibody, was not stained by the 2F7 antibody. As expected, cells transfected with empty vector do not show any HA tag staining. They also do not show any staining by the 2F7 antibody indicating that 2F7 also fails to recognize endogenous, nuclear WT TDP-43.

Similar results were obtained with other antibodies tested and are summarized in Table 6. This pattern of staining by the antibodies tested demonstrates their selectivity for misfolded, pathogenic aggregates of TDP-43 vs WT TDP-43.

TABLE 6

| Binding to TDP-43 aggregates and WT TDP-43 | | |
|---|---|---|
| Monoclonal antibody | Binding to ΔNLS TDP-43 cytoplasmic aggregates | Binding to nuclear WT TDP-43 |
| Mouse | | |
| 2F7 | Yes | No |
| 3E8 | Yes | No |
| 3F11 | Yes | No |
| Rabbit | | |
| 1 (1H3-1K3) | Yes | No |
| 14 (14H1-14K2) | Yes | No |
| 17 (17H3-17K3) | Yes | No |
| 20 (20H2.2-20K1) | Yes | No |
| 28 (28H3-28K1) | Yes | No |
| 30 (30H3-30K1) | Yes | No |
| 36 (36H3-36K2) | Yes | No |
| 38 (38H1-38K1) | Yes | No |

Example 12

Immunocytochemistry of Physiologic Stress Granules

Figure 7:
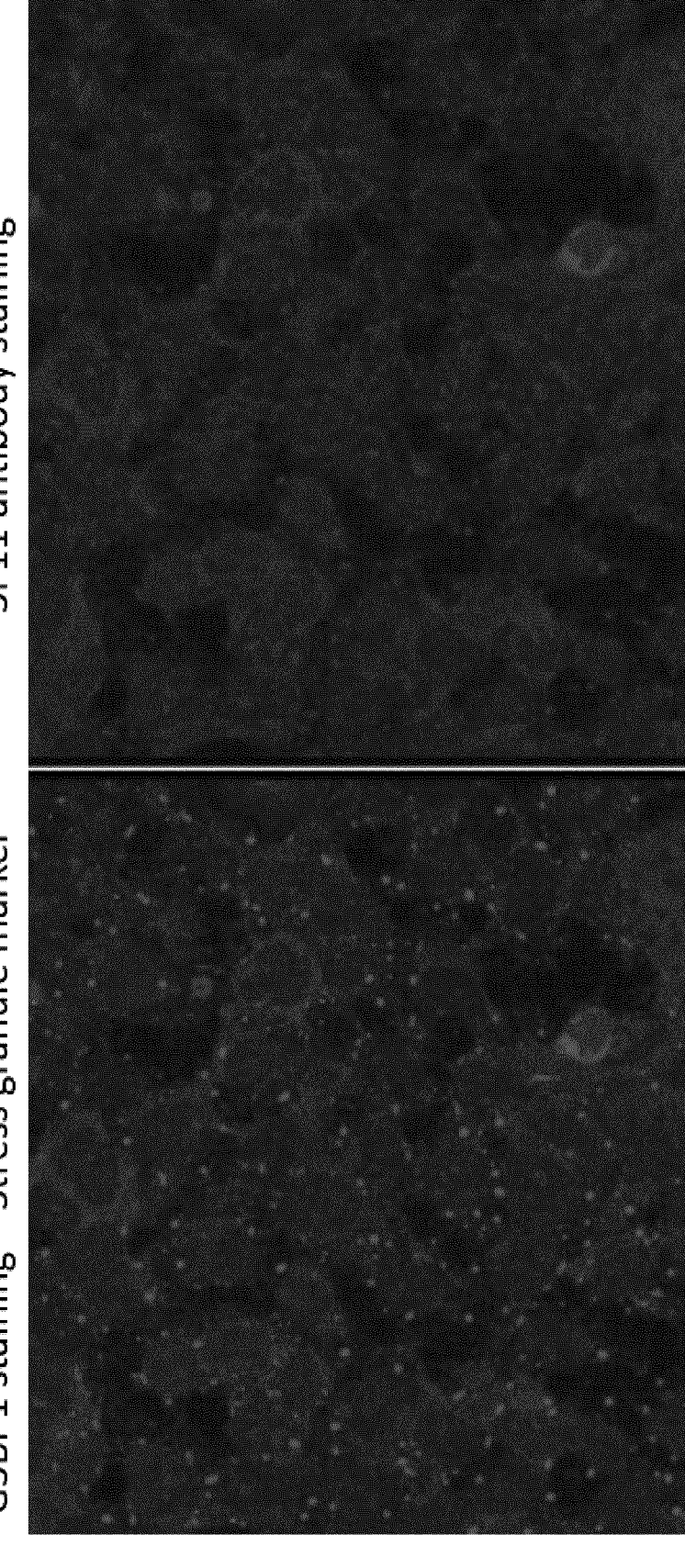
FIGS. 7A and 7B are images showing that 3F11 mouse monoclonal antibody to disease-associated N-terminal TDP43 epitope does not react with physiologic stress granules.

To determine whether the monoclonal antibodies to misfolded TDP-43 reacted with physiologic stress granules, staining was performed on stressed HEK293FT cells. Briefly, HEK293FT cells were stressed by exposure to 1 nM sodium arsenite for 60 min. The cells were then stained with fluorescently labeled antibody against the stress granule marker G3BP1 or with monoclonal anti-TDP-43 test antibodies at 10 μg/ml followed by detection with labeled secondary antibody. Representative results obtained with the mouse monoclonal antibody 3F11 are shown in FIGS. 7A and 7B. With the exception of one antibody, similar results were obtained with other antibodies tested and are included in Table 7 below. Stressed cells showed abundant punctate staining of G3BP1+ stress granules in the cytoplasm (FIG. 7A). By comparison, the same cells stained with 3F11 antibody (FIG. 7B) did not show the presence of cytoplasmic granules in locations with G3BP1 staining indicating that 3F11 does not react with the stress granules in these cells. The lack of binding of the antibodies tested to TDP-43 in physiologic stress granules suggests that they are unlikely to interfere with the protective function of these stress granules.

TABLE 7

| Binding of antibodies to stress granules | |
|---|---|
| Monoclonal antibody | Binding to stress granules |
| Mouse | |
| 2F7 | No |
| 3E8 | No |
| 3F11 | No |
| Rabbit | |
| 1 (1H3-1K3) | No |
| 14 (14H1-14K2) | No |
| 17 (17H3-17K3) | No |
| 20 (20H2.2-20K1) | Yes |
| 28H3-28K1 | No |
| 30 (30H3-30K1) | No |
| 36 (36H3-36K2) | No |
| 38 (38H1-38K1) | No |

Example 13

Characterization of Selected mAbs

Figure 8:
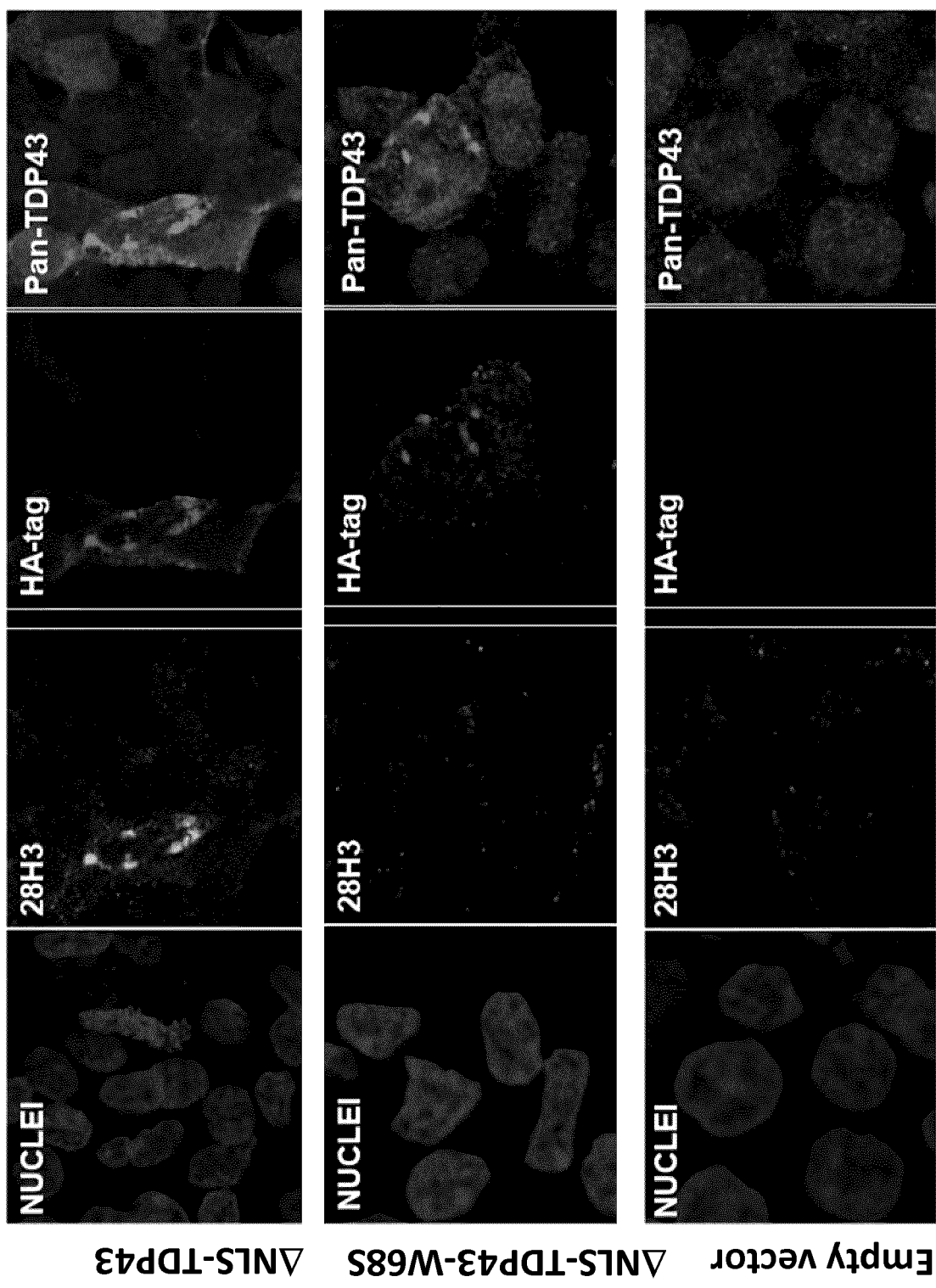
FIG. 8 is a series of images showing co-localization of rabbit monoclonal Ab 28H3 staining with cytoplasmic TDP43 aggregages in ΔNLS-TDP-43 transfected cells, but not ΔNLS-TDP-43-W68S transfected cells.

Monoclonal antibodies were tested as described in example 4 for recognition of cytoplasmic aggregates formed in HEK293FT cells transfected with HA-tagged ΔNLS-TDP-43 vs HA-tagged ΔNLS-TDP-43 in which tryptophan 68 (Trp68) was mutated to serine (W68S). Empty vector was used as a control. In the representative example shown in FIG. 8, cells were stained with either the TDP-43 rabbit monoclonal antibody 28H3-28K1 at 2 μg/ml, mouse pan-TDP43 at 1 μg/ml or chicken anti-HA tag at 0.5 ug/ml. Fluorescently-labeled secondary antibodies Alexa Fluor 488-anti-rabbit, Alexa Fluor 647 anti-mouse and Alexa Fluor 568-anti-chicken were used for detection of bound primary antibody. Nuclei were stained with Hoechst 33342 dye. In cells transfected with HA-tagged ΔNLS-TDP-43, the 28H3-28K1 antibody stained cytoplasmic aggregates that co-localized with HA-positive aggregates of misfolded ΔNLS-TDP-43. In contrast, there was no staining of cytoplasmic aggregates formed by ΔNLS-TDP-43-W68S lacking Trp68. As expected, cells transfected with empty vector did not show any HA tag staining. They also did not show any staining by 28H3-28K1 confirming that the antibody does not recognize endogenous, nuclear WT TDP-43. The pan-TDP-43 antibody recognized cytoplasmic aggregates formed by both forms of transfected TDP-43 as well as endogenous nuclear TDP-43.

Similar results were obtained with most other antibodies tested and are summarized in Table 8. As observed with polyclonal rabbit antibody, this pattern of staining by the monoclonal antibodies tested demonstrates their selectivity for misfolded TDP-43 NTD comprising solvent-exposed Trp68 residue. Clone 20, bound some aggregates of ΔNLS-TDP-43-W68S, and bound to physiological stress granules.

TABLE 8

Summary of binding data for antibodies

| Antibody | Binding to ΔNLS TDP-43 cytoplasmic aggregates | Binding to nuclear WT TDP43 | Binding to stress granules | Requires TRP68 for binding* |
|---|---|---|---|---|
| Mouse 2F7 | Yes | No | No | Yes |
| 3E8 | Yes | No | No | Not determined |
| 3F11 | Yes | No | No | Not Determined |
| Rabbit 1 (1H3-1K3) | Yes | No | No | Yes |
| 14 (14H1-14K2) | Yes | No | No | Yes |
| 17 (17H3-17K3) | Yes | No | No | Yes |
| 20 (20H2.2-20K1) | Yes | No | Yes | +/− (binds some W68S aggregates) |
| 28 (28H3-28K1) | Yes | No | No | Yes |
| 30 (30H3-30K1) | Yes | No | No | Yes |
| 36 (36H3-36K2) | Yes | No | No | Yes |
| 38 (38H1-38K1) | Yes | No | No | Not determined |

*Does not stain aggregates in cells transduced with ΔNLS-W68S TDP43 where tryptophan 68 is mutated to a serine residue Example 14

Antibody Blocking of Misfolded TDP-43 Transmission in HEK293 Cells.

Donor HEK293 cells were transiently transfected with an HA-tagged nuclear-localization signal defective mutant of TDP-43, HA-ΔNLS-TDP43, to express misfolded TDP-43. 48 h post transfection, conditioned medium was collected from donor cells, and centrifuged at 1,000 g for 10 min to remove floating cell debris from the medium. Clarified conditioned media were incubated with 30 μg/ml of each individual TDP-43 misfolding specific antibodies or control mouse IgG1 (Biogen) for 1 h at room temperature with constant rotation prior to adding it to naïve recipient HEK293 cells. The antibodies tested included three mouse monoclonal antibodies to the N-terminal epitope of TDP-43 (3F11, 2F7, 3E8) and two antibodies (9C5, 5B7) against a conformational RRM1 epitope (PCT CA/2018/050634 published as WO 2018/218352). After 48 h of incubation, recipient cell medium was removed, cells were washed with cold PBS twice, and lysed in 2% SDS. Protein concentrations were measured using a BCA assay. 25 μg of lysate was separated on a 10% NuPage gel (Thermo) and transferred onto a PVDF membrane, followed by Western blotting with antibodies against the HA tag (Abcam, rabbit, 1:1000) or GAPDH (Thermo, mouse, 1:50K) as a loading control. HA and GAPDH immuno-reactivity was detected on the Chemi-Doc Imaging System, and intensity was quantitated using Image Lab.

Figure 9:
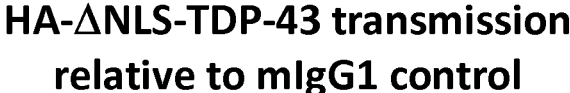
FIG. 9 shows antibody blocking of misfolded TDP-43 transmission in HEK293 cells.
Figure 9:
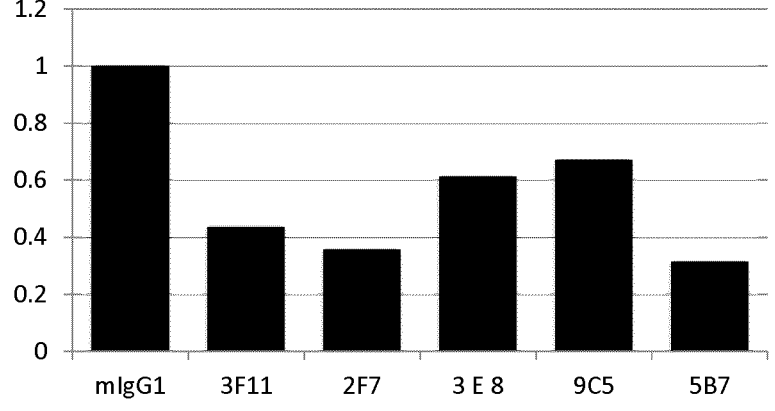

Donor cells transfected with HA-dNLS-TDP43 contained high amounts of HA-tagged TDP-43. Naïve recipient cells incubated with donor cell supernatant treated with control mouse IgG1 (mIgG1) contained detectable amounts of HA-tagged TDP-43 indicating that misfolded aggregates of HA-dNLS-TDP-43 protein were transmitted extracellularly from donor cells to recipient cells. Recipient cells incubated with donor cell supernatant pre-treated with misfolding-specific TDP-43 antibodies contained relatively lower amounts of HA-tagged TDP-43 showing inhibition of transmission by the antibodies. As a negative control, recipient cells incubated with supernatant from untransfected donor cells did not contain any detectable HA-tagged TDP-43. Quantitative analysis of the Western blots is shown in FIG. 9. For each antibody, the HA tag signal was first normalized to the GAPDH signal (HA intensity/GAPDH intensity) and the value obtained for the test antibody was divided by the value obtained with control mIgG1. Relative to control mIgG1, all antibodies tested inhibited transmission of misfolded HA-dNLS-TDP-43 from donor cell supernatant resulting in lower levels of HA-tagged TDP-43 in the recipient cells.

Example 15

Generation of Antibodies Selective for Misfolded, Disease-Associated TDP-43

Misfolded molecular species of TDP-43 have been implicated in the neurotoxicity and prion-like cell-to-cell propagation in amyotrophic lateral sclerosis (ALS) and frontotemporal lobar dementia (FTLD). It was found that a tryptophan (Trp68) in the TDP-43 N-terminal domain (NTD) participates in the cross-seeding of SOD1 misfolding propagation, despite being inaccessible in the natively folded NTD [9]. It was hypothesized that NTD Trp68 becomes exposed when TDP-43 is cytosolically mislocalized/aggregated.

Design/Methods

Rabbits were immunized with an unfolded NTD linear peptide epitope including Trp68 to generate polyclonal and monoclonal antibodies (pAb, mAb). Mice were immunized with the same epitope to generate mAbs. Monoclonal antibody affinity to the immunizing peptide was determined by surface plasmon resonance (SPR). NTD was expressed in *E. coli*, and properly folded monomer status was confirmed by size exclusion chromatography, followed by studies with denaturing and native gel electrophoresis and immunoblotting. Antibody specificity was confirmed by immunohistochemistry (IHC) on patient samples, and immunocytochemistry (ICC) of HEK293 cells transfected with TDP-43 triple-tandem mutation of the nuclear localization sequence (ΔNLS). The ability of antibodies to inhibit the cell to cell transmission of misfolded TDP-43 was assessed in vitro.

Results

SPR of mAbs revealed picomolar affinity to the epitope. Recombinant NTD displayed pAb immunoreactivity only under denaturing conditions. IHC of ALS/FTLD CNS sections, but not normal CNS, was reactive to antibodies. ICC revealed immunoreactivity for mislocalized/aggregated ΔNLS-TDP-43, but not nuclear wild-type TDP-43. Antibodies also failed to recognize TDP-43 in physiologic stress granules in HEK293 cells. A ΔNLS-TDP-43 construct in which Trp68 was mutated to serine did not display immunoreactivity in transfected cells, indicating that Trp68 is immunodominant in the immunizing peptide. Antibodies tested in a cell culture assay were able to inhibit cell to cell transmission of misfolded TDP-43, a process believed to be central to disease pathogenesis (refs. 10, 11,12)

CONCLUSION

A family of antibodies sensitive to solvent exposure of NTD Trp68 that are selective for misfolded/aggregated, disease-associated TDP-43 while sparing physiologically important molecular species was developed. These antibodies may find utility in biomarker and immunotherapy applications for TDP-43 associated diseases.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

[1] Kuo P H, Chiang C H, Wnag Y T, Doudeva L G, Yuan H S, The Crystal Structure of TDP-43 RRM1-DNA Complex Reveals the Specific Recognition for UG- and TG-Rich Nucleic Acids. *Nucleic Acids Res.,* 2014, vol 42, 4712.

[2] DOI: 10.2210/pdb1wf0/pdb (No publication).

[3] Mompean, M., Romano, V., Pantoja-Uceda, D., Stuani, C., Baralle, F. E., Buratti, E., and Laurents, D. V. The TDP-43 N-Terminal Domain Structure at High Resolution. *FEBS J.,* 2016, 283, 1242.

[4] Arai, T., Hasegawa, M., Akiyama, H., Ikeda, K., Nonaka, T., Mori, H., Mann, D., Tsuchiya, K., Yoshida, M., Hashizume, Y., and Oda, T. TDP-43 is a component of ubiquitin-positive tau-negative inclusions in frontotemporal lobar degeneration and amyotrophic lateral sclerosis. *Biochem. Biophys. Res. Commun.,* 2006, 351, 602-611.

[5] Chantelle F. Sephton, Shannon K. Good, Stan Atkin, Colleen M. Dewey, Paul Mayer III, Joachim Herz, and Gang Yu *J. Biol. Chem.* 2010, vol. 285, No. 9, 6826-6834.

[6] Abel, O., Powell, J. F., Andersen, P. M., and Al-Chalabi, A. *Hum Mutat,* 2012, 33:1345-51.

[7] Hamley, I. W. PEG-Peptide Conjugates 2014; 15, 1543-1559; dx.doi.org/10.1021/bm500246w.

[8] Roberts, M J et al *Chemistry for peptide and protein PEGylation* 64:116-127.

[9] Afroz, T et al. Functional and dynamic polymerization of the ALS-linked protein TDP-43 antagonizes its pathologic aggregation. *Nat Comm* (2017) 8:45.

Porta, S et al. Patient-derived frontotemporal lobar degeneration brain extracts induce formation and spreading of TDP-43 pathology in vivo. *Nature Comm* (2018) 9:4220.

Brettschneider, J et al. Sequential distribution of pTDP-43 pathology in behavioral variant frontotemporal dementia (bvFTD). *Acta Neuropathol* (2014) 127:423.

Feiler, M. S. et al. TDP-43 is intercellularly transmitted across axon terminals. *J Cell Biol* (2015) 211:897.

The invention claimed is:

1. An antibody that binds TDP-43 sequence DAGWGNL (SEQ ID NO: 1) in misfolded TDP-43 compared to native TDP-43, the antibody comprising a light chain variable region and a heavy chain variable region, the heavy chain variable region comprising complimentary determining regions CDR-H1, CDR-H2 and CDR-H3, the light chain variable region comprising complementarity determining regions CDR-L1, CDR-L2 and CDR-L3 and with the amino acid sequences of said CDRs comprising the sequences:

```
CDR-H1:
                                          SEQ ID NO: 10
GFSLSRYY;

CDR-H2:
                                          SEQ ID NO: 11
IIPGGTT;

CDR-H3:
                                          SEQ ID NO: 12
AGGPTGNSHFTL;

CDR-L1:
                                          SEQ ID NO: 13
ESVYNNNH;

CDR-L2:
                                          SEQ ID NO: 14
EAS; and

CDR-L3:
                                          SEQ ID NO: 15
SGYKRVTTDGIA,

CDR-H1:
                                          SEQ ID NO: 16
GFSFSSNYV;

CDR-H2:
                                          SEQ ID NO: 17
IWFAGIVDTT;

CDR-H3:
                                          SEQ ID NO: 18
ARNPVGSVNL;
```

```
CDR-L1:
                                          SEQ ID NO: 19
ESVYSNNR;

CDR-L2:
                                          SEQ ID NO: 20
YAS; and

CDR-L3:
                                          SEQ ID NO: 21
AGWRGARTDGVD,

CDR-H1:
                                          SEQ ID NO: 22
GFSFSSSYV;

CDR-H2:
                                          SEQ ID NO: 23
SDTGINT ;

CDR-H3:
                                          SEQ ID NO: 24
ARRYTGDTYLGNFNL ;

CDR-L1:
                                          SEQ ID NO: 25
QSVYKNNY ;

CDR-L2:
                                          SEQ ID NO: 26
KAS ; and

CDR-L3:
                                          SEQ ID NO: 27
AGGWRSLNA,

CDR-H1:
                                          SEQ ID NO: 28
EFSFSSRYW;

CDR-H2:
                                          SEQ ID NO: 29
IYTGSIDAT;

CDR-H3:
                                          SEQ ID NO: 30
VRGSDAWGLYFNL;
```

-continued

CDR-L1:

QSIHKNNY;                                    SEQ ID NO: 31

CDR-L2:

FAS; and                                     SEQ ID NO: 32

CDR-L3:

AGVYSGRIFA,                                  SEQ ID NO: 33

CDR-H1:

GFSLSSYT;                                    SEQ ID NO: 34

CDR-H2:

IYGGIGST;                                    SEQ ID NO: 35

CDR-H3:

GRGDI;                                       SEQ ID NO: 36

CDR-L1:

QSVYKNR;                                     SEQ ID NO: 37

CDR-L2:

GAS; and                                     SEQ ID NO: 38

CDR-L3:

LGNYDCSSVDCGA,                               SEQ ID NO: 39

CDR-H1:

GFSFSAYY;                                    SEQ ID NO: 40

CDR-H2:

TIPIGRT;                                     SEQ ID NO: 41

CDR-H3:

AGGPTGNSHFTL;                                SEQ ID NO: 42

CDR-L1:

ESVYNNNQ;                                    SEQ ID NO: 43

CDR-L2:

QAS; and                                     SEQ ID NO: 44

CDR-L3:

AGYKSPTTDGIA,                                SEQ ID NO: 45

CDR-H1:

GFSLSSYA;                                    SEQ ID NO: 46

CDR-H2:

IYNYET;                                      SEQ ID NO: 47

CDR-H3:

ARDIFRTNTNL;                                 SEQ ID NO: 48

CDR-L1:

QSVYKNNG;                                    SEQ ID NO: 49

-continued

CDR-L2:

FTS; and                                     SEQ ID NO: 50

CDR-L3:

LGGYDCSSRVCGA,                               SEQ ID NO: 51

CDR-H1:

GFSLSSYN;                                    SEQ ID NO: 120

CDR-H2:

IGTGGIT;                                     SEQ ID NO: 121

CDR-H3:

VRSSGSDWWFHI;                                SEQ ID NO: 122

CDR-L1:

QSVYNNNN;                                    SEQ ID NO: 123

CDR-L2:

RAS; and                                     SEQ ID NO: 124

CDR-L3:

QGYFSGFITT,                                  SEQ ID NO: 125

CDR-H1:

GFTFSSYY;                                    SEQ ID NO: 130

CDR-H2:

INSNGGST;                                    SEQ ID NO: 131

CDR-H3:

VRQNYEGAY;                                   SEQ ID NO: 132

CDR-L1:

QSIVHSNGNTY;                                 SEQ ID NO: 133

CDR-L2:

KVS; and                                     SEQ ID NO: 134

CDR-L3:

FQSSHVPWT, or                                SEQ ID NO: 135

CDR-H1:

GFTFSSYY;                                    SEQ ID NO: 140

CDR-H2:

INTNGGST;                                    SEQ ID NO: 141

CDR-H3:

VRQNYEGAY;                                   SEQ ID NO: 142

CDR-L1:

QSIVHSNGNTY;                                 SEQ ID NO: 143

CDR-L2:

KVS; and                                     SEQ ID NO: 144

CDR-L3:

FQSSHVPWT.                                   SEQ ID NO: 145

2. The antibody of claim 1, a. wherein the antibody specifically binds at least W68 in the context of DAGWGNL (SEQ ID NO: 1);

b. wherein the antibody preferentially binds misfolded TDP-43 that is not associated with stress granules;

c. wherein the antibody binds DAGWG (SEQ ID NO: 2), AGWGN (SEQ ID NO: 3), GWGNL (SEQ ID NO: 4) and/or AGWGNL (SEQ ID NO: 5); and/or d. wherein the antibody is raised and/or screened using:

i. an isolated peptide comprising all or part of DAGWGNL (SEQ ID NO: 1), wherein the part is at least 5 or more contiguous amino acids and comprises GWG, optionally wherein the part is DAGWG (SEQ ID NO: 2), AGWGN (SEQ ID NO: 3), or GWGNL (SEQ ID NO: 4); or ii. an immunogen comprising a peptide, the peptide comprising all or part of DAGWGNL (SEQ ID NO: 1) wherein the part is at least 5 or more contiguous amino acids of SEQ ID NO: 1, optionally wherein i) the immunogen comprises multiple peptides, each peptide comprising all or part of DAGWGNL (SEQ ID NO: 1), wherein the multiple peptides are synthesized as a multiple antigenic peptide (MAP), or ii) the peptide is coupled to a carrier protein, optionally bovine serum albumin (BSA) or keyhole limpet haemocyanin (KLH) and optionally wherein the immunogen is used to produce an antibody that that specifically binds at least W68 in the context of DAGWGNL (SEQ ID NO: 1), and/or wherein the antibody preferentially binds misfolded TDP-43.

3. The antibody of claim 1, wherein the antibody is a monoclonal antibody, a single chain antibody and/or wherein the antibody is affinity purified.

4. The antibody of claim 1, wherein the antibody is a binding fragment selected from Fab, Fab', F(ab')2, scFv, dsFv, ds-scFv, dimers, minibodies, diabodies, and multimers thereof.

5. The antibody of claim 1, wherein the amino acid sequence of said CDRs are as set forth in:

```
CDR-H1:
                              SEQ ID NO: 10
GFSLSRYY;

CDR-H2:
                              SEQ ID NO: 11
IIPGGTT;

CDR-H3:
                              SEQ ID NO: 12
AGGPTGNSHFTL;

CDR-L1:
                              SEQ ID NO: 13
ESVYNNNH;

CDR-L2:
                              SEQ ID NO: 14
EAS; and

CDR-L3:
                              SEQ ID NO: 15
SGYKRVTTDGIA,

CDR-H1:
                              SEQ ID NO: 16
GFSFSSNYV;

CDR-H2:
                              SEQ ID NO: 17
IWFAGIVDTT;
```

-continued

```
CDR-H3:
                              SEQ ID NO: 18
ARNPVGSVNL;

CDR-L1:
                              SEQ ID NO: 19
ESVYSNNR;

CDR-L2:
                              SEQ ID NO: 20
YAS; and

CDR-L3:
                              SEQ ID NO: 21
AGWRGARTDGVD,

CDR-H1:
                              SEQ ID NO: 22
GFSFSSSYV;

CDR-H2:
                              SEQ ID NO: 23
SDTGINT ;

CDR-H3:
                              SEQ ID NO: 24
ARRYTGDTYLGNFNL ;

CDR-L1:
                              SEQ ID NO: 25
QSVYKNNY ;

CDR-L2:
                              SEQ ID NO: 26
KAS ; and

CDR-L3:
                              SEQ ID NO: 27
AGGWRSLNA,

CDR-H1:
                              SEQ ID NO: 34
GFSLSSYT;

CDR-H2:
                              SEQ ID NO: 35
IYGGIGST;

CDR-H3:
                              SEQ ID NO: 36
GRGDI;

CDR-L1:
                              SEQ ID NO: 37
QSVYKNR;

CDR-L2:
                              SEQ ID NO: 38
GAS; and

CDR-L3:
                              SEQ ID NO: 39
LGNYDCSSVDCGA,

CDR-H1:
                              SEQ ID NO: 40
GFSFSAYY;

CDR-H2:
                              SEQ ID NO: 41
TIPIGRT;

CDR-H3:
                              SEQ ID NO: 42
AGGPTGNSHFTL;

CDR-L1:
                              SEQ ID NO: 43
ESVYNNNQ;
```

-continued

```
CDR-L2:
                                      SEQ ID NO: 44
QAS; and

CDR-L3:
                                      SEQ ID NO: 45
AGYKSPTTDGIA,

CDR-H1:
                                      SEQ ID NO: 46
GFSLSSYA;

CDR-H2:
                                      SEQ ID NO: 47
IYNYET;

CDR-H3:
                                      SEQ ID NO: 48
ARDIFRTNTNL;

CDR-L1:
                                      SEQ ID NO: 49
QSVYKNNG;

CDR-L2:
                                      SEQ ID NO: 50
FTS; and

CDR-L3:
                                      SEQ ID NO: 51
LGGYDCSSRVCGA,

CDR-H1:
                                      SEQ ID NO: 120
GFSLSSYN;

CDR-H2:
                                      SEQ ID NO: 121
IGTGGIT;

CDR-H3:
                                      SEQ ID NO: 122
VRSSGSDWWFHI;

CDR-L1:
                                      SEQ ID NO: 123
QSVYNNNN;

CDR-L2:
                                      SEQ ID NO: 124
RAS; and

CDR-L3:
                                      SEQ ID NO: 125
QGYFSGFITT,

CDR-H1:
                                      SEQ ID NO: 130
GFTFSSYY;

CDR-H2:
                                      SEQ ID NO: 131
INSNGGST;

CDR-H3:
                                      SEQ ID NO: 132
VRQNYEGAY;

CDR-L1:
                                      SEQ ID NO: 133
QSIVHSNGNTY;

CDR-L2:
                                      SEQ ID NO: 134
KVS; and

CDR-L3:
                                      SEQ ID NO: 135
FQSSHVPWT.
```

6. The antibody of claim 1, wherein the antibody comprises a heavy chain variable region comprising: i) an amino acid sequence as set forth in SEQ ID NO: 98, wherein the CDRs are as set forth in SEQ ID NOs: 10-12, ii) an amino acid sequence with at least 80% or at least 90% sequence identity to SEQ ID NO: 98, wherein the CDR sequences are as set forth in SEQ ID NOs: 10-12, or iii) a conservatively substituted amino acid sequence of i), wherein the CDRs are as set forth in SEQ ID NOs: 10-12, and/or wherein the antibody comprises a light chain variable region comprising an amino acid sequence as set forth in SEQ ID NO: 99, wherein the CDR sequences are as set forth in SEQ ID NOs: 13-15, ii) an amino acid sequence with at least 80% or at least 90% sequence identity to SEQ ID NO: 99, wherein the CDR sequences are as set forth in SEQ ID NOs: 13-15, or iii) a conservatively substituted amino acid sequence of i), wherein the CDR sequences are as set forth in SEQ ID NOs: 13-15, optionally wherein the heavy chain variable region amino acid sequence is encoded by a nucleotide sequence as set out in SEQ ID NO: 76 or a codon degenerate or optimized version thereof and/or the light chain variable region amino acid sequence is encoded by a nucleotide sequence as set out in SEQ ID NO: 77 or a codon degenerate or optimized version thereof; wherein the antibody comprises a heavy chain variable region comprising: i) an amino acid sequence as set forth in SEQ ID NO: 100, wherein the CDR sequences are as set forth in SEQ ID NOs: 16-18, ii) an amino acid sequence with at least 80% or at least 90% sequence identity to SEQ ID NO: 100, wherein the CDR sequences are as set forth in SEQ ID NOs: 16-18, or iii) a conservatively substituted amino acid sequence of i), wherein the CDR sequences are as set forth in SEQ ID NOs: 16-18, and/or wherein the antibody comprises a light chain variable region comprising an amino acid sequence as set forth in SEQ ID NO: 101, wherein the CDR sequences are as set forth in SEQ ID NOs: 19-21, ii) an amino acid sequence with at least 80% or at least 90% sequence identity to SEQ ID NO: 101, wherein the CDR sequences are as set forth in SEQ ID NOs: 19-21, or iii) a conservatively substituted amino acid sequence of i), wherein the CDR sequences are as set forth in SEQ ID NOs: 19-21, optionally wherein the heavy chain variable region amino acid sequence is encoded by a nucleotide sequence as set out in SEQ ID NO: 78 or a codon degenerate or optimized version thereof and/or the light chain variable region amino acid sequence is encoded by a nucleotide sequence as set out in SEQ ID NO: 79 or a codon degenerate or optimized version thereof;

wherein the antibody comprises a heavy chain variable region comprising: i) an amino acid sequence as set forth in SEQ ID NO: 102, wherein the CDR sequences are as set forth in SEQ ID NOs: 22-24, ii) an amino acid sequence with at least 80% or at least 90% sequence identity to SEQ ID NO: 102, wherein the CDR sequences are as set forth in SEQ ID NOs: 22-24, or iii) a conservatively substituted amino acid sequence of i), wherein the CDR sequences are as set forth in SEQ ID NOs: 22-24, and/or wherein the antibody comprises a light chain variable region comprising an amino acid sequence as set forth in SEQ ID NO: 103, wherein the CDR sequences are as set forth in SEQ ID NOs: 25-27, ii) an amino acid sequence with at least 80% or at least 90% sequence identity to SEQ ID NO: 103, wherein the CDR sequences are as set forth in SEQ ID NOs: 25-27, or iii) a conservatively substituted amino acid sequence of i), wherein the CDR sequences are as set forth in SEQ ID NOs: 25-27, optionally wherein the heavy chain variable region amino acid sequence is encoded by a nucleotide sequence as set out in SEQ ID NO: 80 or a codon degenerate or optimized version thereof and/or the light chain variable region amino acid sequence is encoded by a nucleotide sequence as set out in SEQ ID NO: 81 or a codon degenerate or optimized version thereof;

wherein the antibody comprises a heavy chain variable region comprising: i) an amino acid sequence as set forth in SEQ ID NO: 104, wherein the CDR sequences are as set forth in SEQ ID NOs: 28-30, ii) an amino acid sequence with at least 80% or at least 90% sequence identity to SEQ ID NO: 104, wherein the CDR sequences are as set forth in SEQ ID NOs: 28-30, or iii) a conservatively substituted amino acid sequence of i), wherein the CDR sequences are as set forth in SEQ ID NOs: 28-30, and/or wherein the antibody comprises a light chain variable region comprising an amino acid sequence as set forth in SEQ ID NO: 105, wherein the CDR sequences are as set forth in SEQ ID NOs: 31-33, ii) an amino acid sequence with at least 80% or at least 90% sequence identity to SEQ ID NO: 105, wherein the CDR sequences are as set forth in SEQ ID NOs: 31-33, or iii) a conservatively substituted amino acid sequence of i), wherein the CDR sequences are as set forth in SEQ ID NOs: 31-33, optionally wherein the heavy chain variable region amino acid sequence is encoded by a nucleotide sequence as set out in SEQ ID NO: 82 or a codon degenerate or optimized version thereof and/or the light chain variable region amino acid sequence is encoded by a nucleotide sequence as set out in SEQ ID NO: 83 or a codon degenerate or optimized version thereof;

wherein the antibody comprises a heavy chain variable region comprising: i) an amino acid sequence as set forth in SEQ ID NO: 106, wherein the CDR sequences are as set forth in SEQ ID NOs: 34-36, ii) an amino acid sequence with least 80% or at least 90% sequence identity to SEQ ID NO: 106, wherein the CDR sequences are as set forth in SEQ ID NOs: 34-36, or iii) a conservatively substituted amino acid sequence of i), and/or wherein the antibody comprises a light chain variable region comprising an amino acid sequence as set forth in SEQ ID NO: 107, wherein the CDR sequences are as set forth in SEQ ID NOs: 37-39, ii) an amino acid sequence with at least 80% or at least 90% sequence identity to SEQ ID NO: 107, wherein the CDR sequences are as set forth in SEQ ID NOs: 37-39, or iii) a conservatively substituted amino acid sequence of i), wherein the CDR sequences are as set forth in SEQ ID NOs: 34-36, optionally wherein the heavy chain variable region amino acid sequence is encoded by a nucleotide sequence as set out in SEQ ID NO: 84 or a codon degenerate or optimized version thereof and/or the light chain variable region amino acid sequence is encoded by a nucleotide sequence as set out in SEQ ID NO: 85 or a codon degenerate or optimized version thereof;

wherein the antibody comprises a heavy chain variable region comprising: i) an amino acid sequence as set forth in SEQ ID NO: 108, wherein the CDR sequences are as set forth in SEQ ID NOs: 40-42, ii) an amino acid sequence with at least 80% or at least 90% sequence identity to SEQ ID NO: 108, wherein the CDR sequences are as set forth in SEQ ID NOs: 40-42, or iii) a conservatively substituted amino acid sequence of i), wherein the CDR sequences are as set forth in SEQ ID NOs: 40-42, and/or wherein the antibody comprises a light chain variable region comprising an amino acid sequence as set forth in SEQ ID NO: 109, wherein the CDR sequences are as set forth in SEQ ID NOs: 43-45, ii) an amino acid sequence with at least 80% or at least 90% sequence identity to SEQ ID NO: 109, wherein the CDR sequences are as set forth in SEQ ID NOs: 43-45, or iii) a conservatively substituted amino acid sequence of i), wherein the CDR sequences are as set forth in SEQ ID NOs: 43-45, optionally wherein the heavy chain variable region amino acid sequence is encoded by a nucleotide sequence as set out in SEQ ID NO: 86 or a codon degenerate or optimized version thereof and/or the light chain variable region amino acid sequence is encoded by a nucleotide sequence as set out in SEQ ID NO: 87 or a codon degenerate or optimized version thereof;

wherein the antibody comprises a heavy chain variable region comprising: i) an amino acid sequence as set forth in SEQ ID NO: 110, wherein the CDR sequences are as set forth in SEQ ID NOs: 46-48, ii) an amino acid sequence with at least 80% or at least 90% sequence identity to SEQ ID NO: 110, wherein the CDR sequences are as set forth in SEQ ID NOs: 46-48, or iii) a conservatively substituted amino acid sequence of i), wherein the CDR sequences are as set forth in SEQ ID NOs: 46-48, and/or wherein the antibody comprises a light chain variable region comprising an amino acid sequence as set forth in SEQ ID NO: 111, wherein the CDR sequences are as set forth in SEQ ID NOs: 49-51, ii) an amino acid sequence with at least 80% or at least 90% sequence identity to SEQ ID NO: 111, wherein the CDR sequences are as set forth in SEQ ID NOs: 49-51, or iii) a conservatively substituted amino acid sequence of i), wherein the CDR sequences are as set forth in SEQ ID NOs: 49-51, optionally wherein the heavy chain variable region amino acid sequence is encoded by a nucleotide sequence as set out in SEQ ID NO: 88 or a codon degenerate or optimized version thereof and/or the light chain variable region amino acid sequence is encoded by a nucleotide sequence as set out in SEQ ID NO: 89 or a codon degenerate or optimized version thereof;

wherein the antibody comprises a heavy chain variable region comprising: i) an amino acid sequence as set forth in SEQ ID NO: 128, wherein the CDR sequences are as set forth in SEQ ID NOs: 120-122, ii) an amino acid sequence with least 80% or at least 90% sequence identity to SEQ ID NO: 128, wherein the CDR sequences are as set forth in SEQ ID NOs: 120-122, or iii) a conservatively substituted amino acid sequence of i), wherein the CDR sequences are as set forth in SEQ ID NOs: 120-122, and/or wherein the antibody comprises a light chain variable region comprising an amino acid sequence as set forth in SEQ ID NO: 129, wherein the CDR sequences are as set forth in SEQ ID NOs: 123-125, ii) an amino acid sequence with at least 80% or at least 90% sequence identity to SEQ ID NO: 129, wherein the CDR sequences are as set forth in SEQ ID NOs: 123-125, or iii) a conservatively substituted amino acid sequence of i), wherein the CDR sequences are as set forth in SEQ ID NOs: 123-125, optionally wherein the heavy chain variable region amino acid sequence is encoded by a nucleotide sequence as set out in SEQ ID NO: 126 or a codon degenerate or optimized version thereof and/or the light chain variable region amino acid sequence is encoded by a nucleotide sequence as set out in SEQ ID NO: 127 or a codon degenerate or optimized version thereof;

wherein the antibody comprises a heavy chain variable region comprising: i) an amino acid sequence as set forth in SEQ ID NO: 138, wherein the CDR sequences are as set forth in SEQ ID NOs: 130-132, ii) an amino acid sequence at least 80% or at least 90% sequence identity to SEQ ID NO: 138, wherein the CDR sequences are as set forth in SEQ ID NOs: 130-132, or iii) a conservatively substituted amino acid sequence of i), wherein the CDR sequences are as set forth in SEQ ID NOs: 130-132, and/or wherein the antibody comprises a light chain variable region comprising an amino acid sequence as set forth in SEQ ID NO: 139, wherein the CDR sequences are as set forth in SEQ ID NOs: 133-135, ii) an amino acid sequence with at least 80% or at least 90% sequence identity to SEQ ID NO: 139, wherein the CDR sequences are as set forth in SEQ ID NOs: 133-135, or iii) a conservatively substituted amino acid sequence of i), wherein the CDR sequences are as set forth in SEQ ID NOs: 133-135, optionally wherein the heavy chain variable region amino acid sequence is encoded by a nucleotide sequence as set out in SEQ ID NO: 136 or a codon degenerate or optimized version thereof and/or the light chain variable region amino acid sequence is encoded by a nucleotide sequence as set out in SEQ ID NO: 137 or a codon degenerate or optimized version thereof; or wherein the antibody comprises a heavy chain variable region comprising: i) an amino acid sequence as set forth in SEQ ID NO: 148, wherein the CDR sequences are as set forth in SEQ ID NOs: 140-142, ii) an amino acid sequence with at least 80% or at least 90% sequence identity to SEQ ID NO: 148, wherein the CDR sequences are as set forth in SEQ ID NOs: 140-142, or iii) a conservatively substituted amino acid sequence of i), wherein the CDR sequences are as set forth in SEQ ID NOs: 140-142, and/or wherein the antibody comprises a light chain variable region comprising an amino acid sequence as set forth in SEQ ID NO: 149, wherein the CDR sequences are as set forth in SEQ ID NOs: 143-145, ii) an amino acid sequence with least 80% or at least 90% sequence identity to SEQ ID NO: 149, wherein the CDR sequences are as set forth in SEQ ID NOs: 143-145, or iii) a conservatively substituted amino acid sequence of i), wherein the CDR sequences are as set forth in SEQ ID NOs: 143-145, optionally wherein the heavy chain variable region amino acid sequence is encoded by a nucleotide sequence as set out in SEQ ID NO: 146 or a codon degenerate or optimized version thereof and/or the light chain variable region amino acid sequence is encoded by a nucleotide sequence as set out in SEQ ID NO: 147 or a codon degenerate or optimized version thereof.

7. An immunoconjugate comprising the antibody of claim 1 and a detectable label.

8. The antibody of claim 6, wherein the antibody is a monoclonal antibody.

9. The antibody of claim 6, wherein the antibody is a single chain antibody.

10. The antibody of claim 6, wherein the antibody is affinity purified.

11. The antibody of claim 1 wherein:

```
CDR-H1:
                                        SEQ ID NO: 10
GFSLSRYY;

CDR-H2:
                                        SEQ ID NO: 11
IIPGGTT;

CDR-H3:
                                        SEQ ID NO: 12
AGGPTGNSHFTL;

CDR-L1:
                                        SEQ ID NO: 13
ESVYNNNH;

CDR-L2:
                                        SEQ ID NO: 14
EAS; and

CDR-L3:
                                        SEQ ID NO: 15
SGYKRVTTDGIA.
```

12. The antibody of claim 1 wherein:

```
                                        SEQ ID NO: 16
GFSFSSNYV;

CDR-H2:
                                        SEQ ID NO: 17
IWFAGIVDTT;

CDR-H3:
                                        SEQ ID NO: 18
ARNPVGSVNL;

CDR-L1:
                                        SEQ ID NO: 19
ESVYSNNR;

CDR-L2:
                                        SEQ ID NO: 20
YAS; and

CDR-L3:
                                        SEQ ID NO: 21
AGWRGARTDGVD.
```

13. The antibody of claim 1 wherein:

```
CDR-H1:
                                        SEQ ID NO: 22
GFSFSSSYV;

CDR-H2:
                                        SEQ ID NO: 23
SDTGINT ;

CDR-H3:
                                        SEQ ID NO: 24
ARRYTGDTYLGNFNL ;

CDR-L1:
                                        SEQ ID NO: 25
QSVYKNNY ;

CDR-L2:
                                        SEQ ID NO: 26
KAS ; and

CDR-L3:
                                        SEQ ID NO: 27
AGGWRSLNA.
```

14. The antibody of claim 1 wherein:

CDR-H1:
EFSFSSRYW;                           SEQ ID NO: 28

CDR-H2:
IYTGSIDAT;                          SEQ ID NO: 29

CDR-H3:
VRGSDAWGLYFNL;                       SEQ ID NO: 30

CDR-L1:
QSIHKNNY;                           SEQ ID NO: 31

CDR-L2:
FAS; and                            SEQ ID NO: 32

CDR-L3:
AGVYSGRIFA.                         SEQ ID NO: 33

15. The antibody of claim 1 wherein:

CDR-H1:
GFSLSSYT;                           SEQ ID NO: 34

CDR-H2:
IYGGIGST;                           SEQ ID NO: 35

CDR-H3:
GRGDI;                              SEQ ID NO: 36

CDR-L1:
QSVYKNR;                            SEQ ID NO: 37

CDR-L2:
GAS; and                            SEQ ID NO: 38

CDR-L3:
LGNYDCSSVDCGA.                       SEQ ID NO: 39

16. The antibody of claim 1 wherein:

CDR-H1:
GFSFSAYY;                           SEQ ID NO: 40

CDR-H2:
TIPIGRT;                            SEQ ID NO: 41

CDR-H3:
AGGPTGNSHFTL;                        SEQ ID NO: 42

CDR-L1:
ESVYNNNQ;                           SEQ ID NO: 43

CDR-L2:
QAS; and                            SEQ ID NO: 44

CDR-L3:
AGYKSPTTDGIA.                        SEQ ID NO: 45

17. The antibody of claim 1 wherein:

CDR-H1:
GFSLSSYA;                           SEQ ID NO: 46

CDR-H2:
IYNYET;                             SEQ ID NO: 47

CDR-H3:
ARDIFRTNTNL;                         SEQ ID NO: 48

CDR-L1:
QSVYKNNG;                           SEQ ID NO: 49

CDR-L2:
FTS; and                            SEQ ID NO: 50

CDR-L3:
LGGYDCSSRVCGA.                       SEQ ID NO: 51

18. The antibody of claim 1 wherein:

CDR-H1:
GFSLSSYN;                           SEQ ID NO: 120

CDR-H2:
IGTGGIT;                            SEQ ID NO: 121

CDR-H3:
VRSSGSDWWFHI;                        SEQ ID NO: 122

CDR-L1:
QSVYNNNN;                           SEQ ID NO: 123

CDR-L2:
RAS; and                            SEQ ID NO: 124

CDR-L3:
QGYFSGFITT.                         SEQ ID NO: 125

19. The antibody of claim 1 wherein:

CDR-H1:
GFTFSSYY;                           SEQ ID NO: 130

CDR-H2:
INSNGGST;                           SEQ ID NO: 131

CDR-H3:
VRQNYEGAY;                          SEQ ID NO: 132

CDR-L1:
QSIVHSNGNTY;                         SEQ ID NO: 133

CDR-L2:
KVS; and                            SEQ ID NO: 134

CDR-L3:
FQSSHVPWT.                          SEQ ID NO: 135

20. The antibody of claim 1 wherein:

```
CDR-H1:
                              SEQ ID NO: 140
GFTFSSYY;

CDR-H2:
                              SEQ ID NO: 141
INTNGGST;

CDR-H3:
                              SEQ ID NO: 142
VRQNYEGAY;

CDR-L1:
                              SEQ ID NO: 143
QSIVHSNGNTY;

CDR-L2:
                              SEQ ID NO: 144
KVS; and

CDR-L3:
                              SEQ ID NO: 145
FQSSHVPWT.
```

\* \* \* \* \*

SEQUENCE LISTING

```
<160> NUMBER OF SEQ ID NOS: 149

<210> SEQ ID NO 1
<211> LENGTH: 7
<212> TYPE: PRT
<213> ORGANISM: Homo Sapiens

<400> SEQUENCE: 1

Asp Ala Gly Trp Gly Asn Leu
1               5

<210> SEQ ID NO 2
<211> LENGTH: 5
<212> TYPE: PRT
<213> ORGANISM: Homo Sapiens

<400> SEQUENCE: 2

Asp Ala Gly Trp Gly
1               5

<210> SEQ ID NO 3
<211> LENGTH: 6
<212> TYPE: PRT
<213> ORGANISM: Homo Sapiens

<400> SEQUENCE: 3

Asp Ala Gly Trp Gly Asn
1               5

<210> SEQ ID NO 4
```

```
<211> LENGTH: 5
<212> TYPE: PRT
<213> ORGANISM: Homo Sapiens

<400> SEQUENCE: 4

Ala Gly Trp Gly Asn
1               5

<210> SEQ ID NO 5
<211> LENGTH: 6
<212> TYPE: PRT
<213> ORGANISM: Homo Sapiens

<400> SEQUENCE: 5

Ala Gly Trp Gly Asn Leu
1               5

<210> SEQ ID NO 6
<211> LENGTH: 5
<212> TYPE: PRT
<213> ORGANISM: Homo Sapiens

<400> SEQUENCE: 6

Gly Trp Gly Asn Leu
1               5

<210> SEQ ID NO 7
<211> LENGTH: 21
<212> TYPE: PRT
<213> ORGANISM: Homo Sapiens

<400> SEQUENCE: 7

Glu Gly Ile Leu His Ala Pro Asp Ala Gly Trp Gly Asn Leu Val Tyr
1               5                   10                  15

Val Val Asn Tyr Pro
            20

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Cys Asp Ala Gly Trp Gly Asn Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Asp Ala Gly Trp Gly Asn Leu Cys
1               5

<210> SEQ ID NO 10
<211> LENGTH: 8
<212> TYPE: PRT
<213> ORGANISM: Oryctolagus cuniculus

<400> SEQUENCE: 10
```

```
Gly Phe Ser Leu Ser Arg Tyr Tyr
1               5

<210> SEQ ID NO 11
<211> LENGTH: 7
<212> TYPE: PRT
<213> ORGANISM: Oryctolagus cuniculus

<400> SEQUENCE: 11

Ile Ile Pro Gly Gly Thr Thr
1               5

<210> SEQ ID NO 12
<211> LENGTH: 12
<212> TYPE: PRT
<213> ORGANISM: Oryctolagus cuniculus

<400> SEQUENCE: 12

Ala Gly Gly Pro Thr Gly Asn Ser His Phe Thr Leu
1               5                   10

<210> SEQ ID NO 13
<211> LENGTH: 8
<212> TYPE: PRT
<213> ORGANISM: Oryctolagus cuniculus

<400> SEQUENCE: 13

Glu Ser Val Tyr Asn Asn Asn His
1               5

<210> SEQ ID NO 14
<211> LENGTH: 3
<212> TYPE: PRT
<213> ORGANISM: Oryctolagus cuniculus

<400> SEQUENCE: 14

Glu Ala Ser
1

<210> SEQ ID NO 15
<211> LENGTH: 12
<212> TYPE: PRT
<213> ORGANISM: Oryctolagus cuniculus

<400> SEQUENCE: 15

Ser Gly Tyr Lys Arg Val Thr Thr Asp Gly Ile Ala
1               5                   10

<210> SEQ ID NO 16
<211> LENGTH: 9
<212> TYPE: PRT
<213> ORGANISM: Oryctolagus cuniculus

<400> SEQUENCE: 16

Gly Phe Ser Phe Ser Ser Asn Tyr Val
1               5

<210> SEQ ID NO 17
<211> LENGTH: 10
<212> TYPE: PRT
<213> ORGANISM: Oryctolagus cuniculus

<400> SEQUENCE: 17

Ile Trp Phe Ala Gly Ile Val Asp Thr Thr
1               5                   10
```

-continued

```
<210> SEQ ID NO 18
<211> LENGTH: 10
<212> TYPE: PRT
<213> ORGANISM: Oryctolagus cuniculus

<400> SEQUENCE: 18

Ala Arg Asn Pro Val Gly Ser Val Asn Leu
1               5               10

<210> SEQ ID NO 19
<211> LENGTH: 8
<212> TYPE: PRT
<213> ORGANISM: Oryctolagus cuniculus

<400> SEQUENCE: 19

Glu Ser Val Tyr Ser Asn Asn Arg
1               5

<210> SEQ ID NO 20
<211> LENGTH: 3
<212> TYPE: PRT
<213> ORGANISM: Oryctolagus cuniculus

<400> SEQUENCE: 20

Tyr Ala Ser
1

<210> SEQ ID NO 21
<211> LENGTH: 12
<212> TYPE: PRT
<213> ORGANISM: Oryctolagus cuniculus

<400> SEQUENCE: 21

Ala Gly Trp Arg Gly Ala Arg Thr Asp Gly Val Asp
1               5               10

<210> SEQ ID NO 22
<211> LENGTH: 9
<212> TYPE: PRT
<213> ORGANISM: Oryctolagus cuniculus

<400> SEQUENCE: 22

Gly Phe Ser Phe Ser Ser Ser Tyr Val
1               5

<210> SEQ ID NO 23
<211> LENGTH: 7
<212> TYPE: PRT
<213> ORGANISM: Oryctolagus cuniculus

<400> SEQUENCE: 23

Ser Asp Thr Gly Ile Asn Thr
1               5

<210> SEQ ID NO 24
<211> LENGTH: 15
<212> TYPE: PRT
<213> ORGANISM: Oryctolagus cuniculus

<400> SEQUENCE: 24

Ala Arg Arg Tyr Thr Gly Asp Thr Tyr Leu Gly Asn Phe Asn Leu
1               5               10              15
```

-continued

```
<210> SEQ ID NO 25
<211> LENGTH: 8
<212> TYPE: PRT
<213> ORGANISM: Oryctolagus cuniculus

<400> SEQUENCE: 25

Gln Ser Val Tyr Lys Asn Asn Tyr
1               5

<210> SEQ ID NO 26
<211> LENGTH: 3
<212> TYPE: PRT
<213> ORGANISM: Oryctolagus cuniculus

<400> SEQUENCE: 26

Lys Ala Ser
1

<210> SEQ ID NO 27
<211> LENGTH: 9
<212> TYPE: PRT
<213> ORGANISM: Oryctolagus cuniculus

<400> SEQUENCE: 27

Ala Gly Gly Trp Arg Ser Leu Asn Ala
1               5

<210> SEQ ID NO 28
<211> LENGTH: 9
<212> TYPE: PRT
<213> ORGANISM: Oryctolagus cuniculus

<400> SEQUENCE: 28

Glu Phe Ser Phe Ser Ser Arg Tyr Trp
1               5

<210> SEQ ID NO 29
<211> LENGTH: 9
<212> TYPE: PRT
<213> ORGANISM: Oryctolagus cuniculus

<400> SEQUENCE: 29

Ile Tyr Thr Gly Ser Ile Asp Ala Thr
1               5

<210> SEQ ID NO 30
<211> LENGTH: 13
<212> TYPE: PRT
<213> ORGANISM: Oryctolagus cuniculus

<400> SEQUENCE: 30

Val Arg Gly Ser Asp Ala Trp Gly Leu Tyr Phe Asn Leu
1               5                   10

<210> SEQ ID NO 31
<211> LENGTH: 8
<212> TYPE: PRT
<213> ORGANISM: Oryctolagus cuniculus

<400> SEQUENCE: 31

Gln Ser Ile His Lys Asn Asn Tyr
1               5

<210> SEQ ID NO 32
<211> LENGTH: 3
```

```
<212> TYPE: PRT
<213> ORGANISM: Oryctolagus cuniculus

<400> SEQUENCE: 32

Phe Ala Ser
1

<210> SEQ ID NO 33
<211> LENGTH: 10
<212> TYPE: PRT
<213> ORGANISM: Oryctolagus cuniculus

<400> SEQUENCE: 33

Ala Gly Val Tyr Ser Gly Arg Ile Phe Ala
1               5                   10

<210> SEQ ID NO 34
<211> LENGTH: 8
<212> TYPE: PRT
<213> ORGANISM: Oryctolagus cuniculus

<400> SEQUENCE: 34

Gly Phe Ser Leu Ser Ser Tyr Thr
1               5

<210> SEQ ID NO 35
<211> LENGTH: 8
<212> TYPE: PRT
<213> ORGANISM: Oryctolagus cuniculus

<400> SEQUENCE: 35

Ile Tyr Gly Gly Ile Gly Ser Thr
1               5

<210> SEQ ID NO 36
<211> LENGTH: 5
<212> TYPE: PRT
<213> ORGANISM: Oryctolagus cuniculus

<400> SEQUENCE: 36

Gly Arg Gly Asp Ile
1               5

<210> SEQ ID NO 37
<211> LENGTH: 7
<212> TYPE: PRT
<213> ORGANISM: Oryctolagus cuniculus

<400> SEQUENCE: 37

Gln Ser Val Tyr Lys Asn Arg
1               5

<210> SEQ ID NO 38
<211> LENGTH: 3
<212> TYPE: PRT
<213> ORGANISM: Oryctolagus cuniculus

<400> SEQUENCE: 38

Gly Ala Ser
1

<210> SEQ ID NO 39
<211> LENGTH: 13
<212> TYPE: PRT
<213> ORGANISM: Oryctolagus cuniculus
```

<400> SEQUENCE: 39

Leu Gly Asn Tyr Asp Cys Ser Ser Val Asp Cys Gly Ala
1               5                   10

<210> SEQ ID NO 40
<211> LENGTH: 8
<212> TYPE: PRT
<213> ORGANISM: Oryctolagus cuniculus

<400> SEQUENCE: 40

Gly Phe Ser Phe Ser Ala Tyr Tyr
1               5

<210> SEQ ID NO 41
<211> LENGTH: 7
<212> TYPE: PRT
<213> ORGANISM: Oryctolagus cuniculus

<400> SEQUENCE: 41

Thr Ile Pro Ile Gly Arg Thr
1               5

<210> SEQ ID NO 42
<211> LENGTH: 12
<212> TYPE: PRT
<213> ORGANISM: Oryctolagus cuniculus

<400> SEQUENCE: 42

Ala Gly Gly Pro Thr Gly Asn Ser His Phe Thr Leu
1               5                   10

<210> SEQ ID NO 43
<211> LENGTH: 8
<212> TYPE: PRT
<213> ORGANISM: Oryctolagus cuniculus

<400> SEQUENCE: 43

Glu Ser Val Tyr Asn Asn Asn Gln
1               5

<210> SEQ ID NO 44
<211> LENGTH: 3
<212> TYPE: PRT
<213> ORGANISM: Oryctolagus cuniculus

<400> SEQUENCE: 44

Gln Ala Ser
1

<210> SEQ ID NO 45
<211> LENGTH: 12
<212> TYPE: PRT
<213> ORGANISM: Oryctolagus cuniculus

<400> SEQUENCE: 45

Ala Gly Tyr Lys Ser Pro Thr Thr Asp Gly Ile Ala
1               5                   10

<210> SEQ ID NO 46
<211> LENGTH: 8
<212> TYPE: PRT
<213> ORGANISM: Oryctolagus cuniculus

<400> SEQUENCE: 46

-continued

```
Gly Phe Ser Leu Ser Ser Tyr Ala
1               5

<210> SEQ ID NO 47
<211> LENGTH: 6
<212> TYPE: PRT
<213> ORGANISM: Oryctolagus cuniculus

<400> SEQUENCE: 47

Ile Tyr Asn Tyr Glu Thr
1               5

<210> SEQ ID NO 48
<211> LENGTH: 11
<212> TYPE: PRT
<213> ORGANISM: Oryctolagus cuniculus

<400> SEQUENCE: 48

Ala Arg Asp Ile Phe Arg Thr Asn Thr Asn Leu
1               5                   10

<210> SEQ ID NO 49
<211> LENGTH: 8
<212> TYPE: PRT
<213> ORGANISM: Oryctolagus cuniculus

<400> SEQUENCE: 49

Gln Ser Val Tyr Lys Asn Asn Gly
1               5

<210> SEQ ID NO 50
<211> LENGTH: 3
<212> TYPE: PRT
<213> ORGANISM: Oryctolagus cuniculus

<400> SEQUENCE: 50

Phe Thr Ser
1

<210> SEQ ID NO 51
<211> LENGTH: 13
<212> TYPE: PRT
<213> ORGANISM: Oryctolagus cuniculus

<400> SEQUENCE: 51

Leu Gly Gly Tyr Asp Cys Ser Ser Arg Val Cys Gly Ala
1               5                   10

<210> SEQ ID NO 52
<211> LENGTH: 8
<212> TYPE: PRT
<213> ORGANISM: Oryctolagus cuniculus

<400> SEQUENCE: 52

Gly Phe Thr Phe Ser Ala Tyr Tyr
1               5

<210> SEQ ID NO 53
<211> LENGTH: 7
<212> TYPE: PRT
<213> ORGANISM: Oryctolagus cuniculus

<400> SEQUENCE: 53

Thr Ile Pro Arg Gly Ile Thr
```

-continued

```
1               5

<210> SEQ ID NO 54
<211> LENGTH: 12
<212> TYPE: PRT
<213> ORGANISM: Oryctolagus cuniculus

<400> SEQUENCE: 54

Ala Gly Gly Pro Thr Gly Asn Ser His Phe Thr Leu
1               5                   10

<210> SEQ ID NO 55
<211> LENGTH: 8
<212> TYPE: PRT
<213> ORGANISM: Oryctolagus cuniculus

<400> SEQUENCE: 55

Glu Ser Val Tyr Ala Asn Asn Gln
1               5

<210> SEQ ID NO 56
<211> LENGTH: 3
<212> TYPE: PRT
<213> ORGANISM: Oryctolagus cuniculus

<400> SEQUENCE: 56

Gln Ala Ser
1

<210> SEQ ID NO 57
<211> LENGTH: 12
<212> TYPE: PRT
<213> ORGANISM: Oryctolagus cuniculus

<400> SEQUENCE: 57

Ser Gly Tyr Val Arg Thr Thr Thr Asp Gly Ile Ala
1               5                   10

<210> SEQ ID NO 58
<211> LENGTH: 8
<212> TYPE: PRT
<213> ORGANISM: Oryctolagus cuniculus

<400> SEQUENCE: 58

Gly Phe Ser Leu Ile Arg Tyr Tyr
1               5

<210> SEQ ID NO 59
<211> LENGTH: 7
<212> TYPE: PRT
<213> ORGANISM: Oryctolagus cuniculus

<400> SEQUENCE: 59

Thr Ile Pro Arg Gly Ile Thr
1               5

<210> SEQ ID NO 60
<211> LENGTH: 12
<212> TYPE: PRT
<213> ORGANISM: Oryctolagus cuniculus

<400> SEQUENCE: 60

Ala Gly Gly Pro Thr Gly Asn Ser His Phe Thr Leu
1               5                   10
```

```
<210> SEQ ID NO 61
<211> LENGTH: 8
<212> TYPE: PRT
<213> ORGANISM: Oryctolagus cuniculus

<400> SEQUENCE: 61

Glu Ser Val Tyr Asn Asn Asn Gln
1               5

<210> SEQ ID NO 62
<211> LENGTH: 3
<212> TYPE: PRT
<213> ORGANISM: Oryctolagus cuniculus

<400> SEQUENCE: 62

Gln Ala Ser
1

<210> SEQ ID NO 63
<211> LENGTH: 12
<212> TYPE: PRT
<213> ORGANISM: Oryctolagus cuniculus

<400> SEQUENCE: 63

Ser Gly Tyr Lys Ser Thr Thr Thr Asp Gly Ile Ala
1               5                   10

<210> SEQ ID NO 64
<211> LENGTH: 9
<212> TYPE: PRT
<213> ORGANISM: Oryctolagus cuniculus

<400> SEQUENCE: 64

Gly Phe Ser Phe Ser Ser Ser Tyr Val
1               5

<210> SEQ ID NO 65
<211> LENGTH: 9
<212> TYPE: PRT
<213> ORGANISM: Oryctolagus cuniculus

<400> SEQUENCE: 65

Ile Tyr Phe Ala Gly Ile Asp Thr Ile
1               5

<210> SEQ ID NO 66
<211> LENGTH: 10
<212> TYPE: PRT
<213> ORGANISM: Oryctolagus cuniculus

<400> SEQUENCE: 66

Ala Arg Asn Pro Ile Gly Ser Val Asn Leu
1               5                   10

<210> SEQ ID NO 67
<211> LENGTH: 8
<212> TYPE: PRT
<213> ORGANISM: Oryctolagus cuniculus

<400> SEQUENCE: 67

Gln Ser Val Tyr Ser Asn Asn Arg
1               5

<210> SEQ ID NO 68
```

```
<211> LENGTH: 3
<212> TYPE: PRT
<213> ORGANISM: Oryctolagus cuniculus

<400> SEQUENCE: 68

Tyr Leu Ser
1

<210> SEQ ID NO 69
<211> LENGTH: 12
<212> TYPE: PRT
<213> ORGANISM: Oryctolagus cuniculus

<400> SEQUENCE: 69

Ala Gly Trp Arg Gly Ala Thr Thr Asp Gly Val Asp
1               5                   10

<210> SEQ ID NO 70
<211> LENGTH: 9
<212> TYPE: PRT
<213> ORGANISM: Oryctolagus cuniculus

<400> SEQUENCE: 70

Gly Phe Ser Phe Asn Ser Asn Tyr Val
1               5

<210> SEQ ID NO 71
<211> LENGTH: 10
<212> TYPE: PRT
<213> ORGANISM: Oryctolagus cuniculus

<400> SEQUENCE: 71

Ile Trp Phe Ala Gly Ser Gly Asp Val Ile
1               5                   10

<210> SEQ ID NO 72
<211> LENGTH: 10
<212> TYPE: PRT
<213> ORGANISM: Oryctolagus cuniculus

<400> SEQUENCE: 72

Ala Arg Asn Pro Val Gly Ser Val Asn Leu
1               5                   10

<210> SEQ ID NO 73
<211> LENGTH: 8
<212> TYPE: PRT
<213> ORGANISM: Oryctolagus cuniculus

<400> SEQUENCE: 73

Glu Ser Val Tyr Ile Asn Asn Arg
1               5

<210> SEQ ID NO 74
<211> LENGTH: 3
<212> TYPE: PRT
<213> ORGANISM: Oryctolagus cuniculus

<400> SEQUENCE: 74

Tyr Ala Ser
1

<210> SEQ ID NO 75
<211> LENGTH: 12
<212> TYPE: PRT
```

<213> ORGANISM: Oryctolagus cuniculus

<400> SEQUENCE: 75

Ala Gly Trp Arg Gly Ala Thr Thr Asp Gly Ile Asp
1               5                   10

<210> SEQ ID NO 76
<211> LENGTH: 341
<212> TYPE: DNA
<213> ORGANISM: Oryctolagus cuniculus

<400> SEQUENCE: 76
cagtcggtgg aggagtccgg gggtcgcctg gtcacgcctg ggacacccct gacactcacc      60
tgcacagtct ctggattctc cctcagtagg tactacatga cctgggtccg ccaggctcca     120
gggaaggggc tggaatacat cggggtcatt attcctggtg gtaccacata ctacgcgagc     180
tgggcgaaag gccgattcac catctccaaa acctcgacca cggtggatct gagaatcacc     240
agtccgacaa ccgaggacac ggccacttat ttctgtgccg gaggtcctac tggtaacagc     300
cactttacat tgtggggcca gggcaccctg gtcaccgtct c                         341

<210> SEQ ID NO 77
<211> LENGTH: 331
<212> TYPE: DNA
<213> ORGANISM: Oryctolagus cuniculus

<400> SEQUENCE: 77
gtgatgaccc agactccatc ttccaagtct gtccctgtgg gaggcacagt caccatcaat      60
tgccaggcca gtgagagtgt ttataataac aaccacttat cctggtatca gcagaaatca     120
gggcagcctc ccaagctcct gatctacgaa gcatccaaac tggaatctgg ggtcccaccg     180
cggttcaaag gcagtggatc tgggacacag ttcactctca ccatcagcga tgtggtgtgt     240
gacgatgctg ccacttacta ctgttcagga tataaacgtg ttactactga tggtattgct     300
ttcggcggag ggaccgaggt ggtggtcaaa g                                    331

<210> SEQ ID NO 78
<211> LENGTH: 353
<212> TYPE: DNA
<213> ORGANISM: Oryctolagus cuniculus

<400> SEQUENCE: 78
caggagcagc tggaggagtc cggggggagac ctggtcaagc ctgagggatc cctgacactc      60
acctgcacag cctctggatt ctccttcagt agcaactacg tgatgtgctg ggtccgccag     120
gctccaggga aggggctgga gtgggtcgca tgcatttggt ttgctggtat tgttgatact     180
acttactacg cgacctgggc gaaaggccga ttcaccatct ccaaaacctc gtcgaccacg     240
gtgactctgc aaatgaccag tctgacagcc gcggacacgg ccacctattt ctgtgcgaga     300
aatcctgttg gtagtgtgaa cttgtggggc agggcaccc tggtcaccgt ctc             353

<210> SEQ ID NO 79
<211> LENGTH: 331
<212> TYPE: DNA
<213> ORGANISM: Oryctolagus cuniculus

<400> SEQUENCE: 79
gtgatgaccc agactccatc ttccaagtct gtccctgtgg gaggctcagt caccatcaat      60
tgccaggcca gtgagagtgt ttatagtaac aaccgcttat cctggtatca gcagaaacca     120

```
gggcagcctc ctaagctcct gatctattat gcatccactc tggaatctgg ggtcccatcg      180
cggttcaaag gcagtggatt tgggacacac ttcactctca ccatcagcgg cgcgcagtgt      240
gacgatgctg ccacttacta ctgtgcagga tggagaggtg ctaggactga tggtgtagat      300
ttcggcggag ggaccgaggt ggtggtcaaa g                                     331
```

```
<210> SEQ ID NO 80
<211> LENGTH: 359
<212> TYPE: DNA
<213> ORGANISM: Oryctolagus cuniculus

<400> SEQUENCE: 80
caggagcagc tggtggagtc cggggggaggc ctggtccagc ctggggcatc cctgacactc       60
acctgcacag cctctggatt ctccttcagt agcagctacg tgatgtgctg ggtccgccag      120
gctccaggga aggggctgga atggatcaca tgcagtgata ctggtattaa cacatggtac      180
gcgagctggg cgaaaggccg attcaccatc tccaaaacct cgtcgaccac ggtgactctg      240
caaatgacca gtctgacagc cgcggacacg gccacctatt tctgtgcgag acgttatact      300
ggcgatactt atttgggaaa ctttaacttg tggggccagg gcaccctggt caccgtctc       359
```

```
<210> SEQ ID NO 81
<211> LENGTH: 328
<212> TYPE: DNA
<213> ORGANISM: Oryctolagus cuniculus

<400> SEQUENCE: 81
gcccaagtgc tgacccagac tccagcctcg gtgtctgcag ctgtgggagg cacagtcacc       60
atcaactgcc aggccagtca gagtgtttat aagaacaact acttatcctg gtatcagcag      120
aaaccagggc agcctcccaa gctcctgatc tacaaggctt ccactctggc atctgggggtc      180 ccatcgcggt tcaagggcag tggatctggg acacagttca ctctcaccat cagcgacgtg      240
cagtgtgacg atgctgccac ttactactgt gcaggcggtt ggcgtagtct aaatgctttc      300
ggcggaggga ccgaggtggt ggtcaaag                                         328
```

```
<210> SEQ ID NO 82
<211> LENGTH: 359
<212> TYPE: DNA
<213> ORGANISM: Oryctolagus cuniculus

<400> SEQUENCE: 82
caggagcagc tggaggagtc cggggggagac ctggtcaagc ctggggcatc cctgacactc       60
acctgcacag cctctgaatt ctccttcagt agtagatact gggcatgctg ggtccgccag      120
gctccaggga aggggctgga gtggagcgca tgcatttata ctggtagtat tgatgctact      180
tactacgcga gctgggcgaa aggccgattc accatctcca aaacctcgtc gaccacggtg      240
actctgcaag tgaccagtct gacagccgcg gacacggcca cctatttctg tgtgaggggg      300
agtgatgcct ggggtctcta ctttaacttg tggggccagg gcaccctggt caccgtctc       359
```

```
<210> SEQ ID NO 83
<211> LENGTH: 324
<212> TYPE: DNA
<213> ORGANISM: Oryctolagus cuniculus

<400> SEQUENCE: 83
tgctgaccca gactccatcc tccgtgtctg cagctgtggg aggcacagtc accgtcagtt       60
gccagtccag tcagagtatt cataagaata attacttagc ctggtatcag cagaaaccag      120
```

-continued

```
ggcagcctcc caagctcctg atctattttg catccactct ggcatctggg gtcccatcgc      180
ggttcaaagg cagtggatct gggacacagt tcactctcac catcagtgac ctggagtgtg      240
acgatgctgc cacttactac tgtgcaggcg tttatagtgg tcgtattttt gctttcggcg      300
gagggaccga ggtggtggtc aaag                                             324

<210> SEQ ID NO 84
<211> LENGTH: 323
<212> TYPE: DNA
<213> ORGANISM: Oryctolagus cuniculus

<400> SEQUENCE: 84
cagtcggtgg aggagtccgg gggtcgcctg gtcacgcctg ggacacccct gacactcacc       60
tgcaaagtct ctggattctc cctcagtagc tatacaatga tctgggtccg ccaggctcca      120
gggaaggggc tggagtggat cgggtacatt tatggtggta ttggtagcac atggtacgcg      180
agctgggcga aaggccgatt caccatctcc aaaacctcga ccacggtgga tctgaaaatc      240
accagtccga caaccgagga cacggccacc tatttctgtg cagaggggga catctggggc      300
cagggcaccc tggtcaccgt ctc                                              323

<210> SEQ ID NO 85
<211> LENGTH: 331
<212> TYPE: DNA
<213> ORGANISM: Oryctolagus cuniculus

<400> SEQUENCE: 85
gtgctgaccc agactgcatc ccccgtgtct gcggctgtgg gaggcacagt caccatcaat       60
tgccagtcca gtcagagtgt ttataagaac cgcttatcct ggtatcagca gaaaccaggg      120
cagtctccca agcgcctgat ctatggtgca tccactctgg aatctggggt cccatcgcgg      180
ttcaaaggca gcggatctgg gacgcagttc actctcacca tcagcgacgt gcagtgtgac      240
gatgctgcca cttactactg tctaggcaat tatgattgta gtagtgttga ttgtggtgct      300
ttcggcggag ggaccgaggt ggtggtcaaa g                                     331

<210> SEQ ID NO 86
<211> LENGTH: 341
<212> TYPE: DNA
<213> ORGANISM: Oryctolagus cuniculus

<400> SEQUENCE: 86
cagtcggtgg aggagtccgg gggtcgcctg gtcacgcctg ggacacccct gacactcacc       60
tgcacagtct ctggattctc cttcagtgcc tactacatga cctgggtccg ccaggctcca      120
gggaaggggc tggaattcat cggagtcact atacctattg ccgcacgta ctacgcgagc      180 tgggcgaaag gccgattcac catctccaaa acctcgacca cggtgcatct gaaaatcacc      240
agtccgacaa ccgaggacac ggccgcttat ttctgtgccg gaggtcctac tggtaatagc      300
cactttacat tgtggggcca gggcaccctg gtcaccgtct c                          341

<210> SEQ ID NO 87
<211> LENGTH: 331
<212> TYPE: DNA
<213> ORGANISM: Oryctolagus cuniculus

<400> SEQUENCE: 87
gtgatgaccc agactccatc ttccaagtct gtccctgtgg gagacacagt taccatcaat       60
```

-continued

```
tgccaggcca gtgagagtgt ttataataac aaccaattat cctggtatca gcagaaacca   120
gggcagcctc ccaagctcct gatctaccag gcatccaaac tggaatctgg ggtcccatcg   180
cggttcaaag gcagtggatc tgggacacag ttcactctca ccatcagcga tgtggtgtgt   240
gacgatgctg ccacttacta ctgtgcagga tataaaagtc ctactactga tggtattgct   300
ttcggcggag ggaccgaggt ggtggtcaaa g                                  331
```

```
<210> SEQ ID NO 88
<211> LENGTH: 335
<212> TYPE: DNA
<213> ORGANISM: Oryctolagus cuniculus

<400> SEQUENCE: 88
cagtcggtgg aggagtccgg gggtcgcctg gtcacgcctg ggacacccct gacactcacc    60
tgcacagtct ctggattctc cctcagtagc tatgcaatga gctgggtccg ccaggctcca   120
gggaaggggc tggaatggat cggattcatt tataattatg aaacatacta cgcgaactgg   180
gcgaaaggcc gattcaccat ctccaaaacc tcgacctcgg tggttctgaa aatcaccagt   240
ccgacaaccg acgacacggc cacctatttc tgtgccagag atattttttcg tactaatact   300 aacttgtggg gccagggcac cctggtcacc gtctc                              335
```

```
<210> SEQ ID NO 89
<211> LENGTH: 334
<212> TYPE: DNA
<213> ORGANISM: Oryctolagus cuniculus

<400> SEQUENCE: 89
gtgctgaccc agactgcatc gcccgtgtct gcagttgtgg aagcacagt caccatcaat     60 tgccaggcca gtcagagtgt ttataagaac aacggcttat cctggtatca gcagaaacca   120
gggcagcctc ccaaaggcct gatctctttt acatcgactc tggcatctgg ggtctcatcg   180
cggttcaaag gcagtggatc tgggacacag tttactctca ccatcagcga cgtgcagtgt   240
gacgatgctg ccacttacta ctgtctaggc ggttatgatt gtagtagtcg tgtttgtggt   300
gctttcggcg gagggaccga ggtggtggtc aaag                              334
```

```
<210> SEQ ID NO 90
<211> LENGTH: 341
<212> TYPE: DNA
<213> ORGANISM: Oryctolagus cuniculus

<400> SEQUENCE: 90
cagtcggtgg aggagtccgg gggtcgcctg gtcacgcctg ggacacccct gacactcacc    60
tgcaccgtct ctggattcac cttcagtgcc tactacatga gctgggtccg ccaggctcca   120
gggaaggggc tggaatacat cggagtcacc attcctagag gtatcacata ttacgcgaac   180
tgggcgaaag gccgattcac catctccaaa acctcgacca cggtggatct gagaatcacc   240
agtccgacaa ccgaggacac ggccacttat ttctgtgccg aggtcctac tggtaatagc   300 cactttacat tgtggggcca gggcaccctg gtcaccgtct c                      341
```

```
<210> SEQ ID NO 91
<211> LENGTH: 331
<212> TYPE: DNA
<213> ORGANISM: Oryctolagus cuniculus

<400> SEQUENCE: 91
gtgatgaccc agactccatc ttccaagtct gtccctgtgg gagacacagt caccatcaat    60
```

```
tgccaggcca gtgagagtgt ttatgcgaac aaccaattat cctggtatca gcagaaacaa        120
gggcagcctc ccaagctcct gatctaccag gcatccaaac tggaatctgg ggtcccatcg        180
cggttcagtg gcagtggatc tgggacacag ttcgctctca ccatcaccga cgtgcagtgt        240
gacgatgctg ccacttacta ctgttcagga tatgtgcgta ctactactga tggtattgct        300
ttcggcggag ggaccgaggt ggtggtcaaa g                                        331
```

<210> SEQ ID NO 92
<211> LENGTH: 341
<212> TYPE: DNA
<213> ORGANISM: Oryctolagus cuniculus

<400> SEQUENCE: 92

```
cagtcggtgg aggagtccgg gggtcgcctg gtcacgcctg ggacacccct gacactcacc         60
tgcacagtct ctggattctc cctcattaga tactacgtga cctgggtccg ccaggctcca        120
gggaaggggc tggaatacat cggagtcact attcccaggg gtatcacata ctacgcgagc        180
tgggcgaaag ccgattcac catctccaaa acctcgacca cggtggacct gaaaatcacc         240
agtccgacaa ccgaggacac ggccacttat ttctgtgccg gaggtcctac tggtaatagc        300
cactttacat tgtggggcca gggcaccctg gtcaccgtct c                            341
```

<210> SEQ ID NO 93
<211> LENGTH: 331
<212> TYPE: DNA
<213> ORGANISM: Oryctolagus cuniculus

<400> SEQUENCE: 93

```
gtgatgaccc agaccccatc ttccaagtct gtccctgtgg gagacacagt caccatcaat         60
tgccaggcca gtgagagtgt ttataataac aaccaattat cttggtatca gcagaaacca        120
gggcagcctc ccaagctcct gatctaccag gcatccaaac tggaatctgg ggtcccatcg        180
catttcagtg gcagtggatc tgggacacag ttcactctca ccatcagcga cgtgcagtgt        240
gacgatgctg ccacttacta ctgttcagga tataaaagta ctactactga tggtattgct        300
ttcggcggag ggaccgaggt ggtggtcaaa g                                        331
```

<210> SEQ ID NO 94
<211> LENGTH: 350
<212> TYPE: DNA
<213> ORGANISM: Oryctolagus cuniculus

<400> SEQUENCE: 94

```
caggagcagt tggaggagtc cggggggagac ctggtcaagc ctggggcatc cctgacactc         60
acctgcaaag cctctggatt ctccttcagt agcagctacg tgatgtgctg ggtccgccag        120
gctccaggga aggggctgga gtggatcgca tgcatttatt ttgctggtat tgatactatc        180
tactacgcga gctgggcgaa aggccgattc accatctcca aaacctcgtc gaccacggtg        240
actctgcaaa tgaccagtct gacagccgcg gacacggcca cctatttctg tgcgagaaat        300
cctattggta gtgtgaattt gtggggccag ggcaccctgg tcaccgtctc                    350
```

<210> SEQ ID NO 95
<211> LENGTH: 332
<212> TYPE: DNA
<213> ORGANISM: Oryctolagus cuniculus

<400> SEQUENCE: 95

-continued

```
cgtgatgacc cagactccat cttccaagtc tgtccctgtg ggaggcacag tcaccatcaa      60
ttgccaggcc agtcagagtg tttatagtaa caaccgctta tcctggtttc agcagaaacc     120
agggcagcct cccaagctcc tgatctatta tttatccact ctggcatctg gggtcccatc     180
gcggttcaaa ggcagtggat ctgggacaca gttcactctc accatcagcg acgtgcagtg     240
tgacgatgct gccacttact actgtgcagg atggagaggt gccactactg atggtgttga     300
tttcggcgga gggaccgagg tggtggtcaa ag                                   332
```

<210> SEQ ID NO 96
<211> LENGTH: 353
<212> TYPE: DNA
<213> ORGANISM: Oryctolagus cuniculus

<400> SEQUENCE: 96

```
caggagcagc tggaggagtc cggggggagac ctggtcacgc ctggaggaac cctgacactc      60
acctgcaaag cctctggatt ctccttcaat agcaactacg tgatgtgctg ggtccgccag     120
gctccaggga aggggctgga gtggatcgca tgcatttggt ttgctggtag tggtgatgtt     180
atctactatg cgagctgggc gaaaggccga ttcaccatct ccaaaacctc gtcgaccacg     240
gtgactctgc aaatgaccag tctgacagcc gcggacacgg ccacccattt ctgtgcgaga     300
aatcctgttg gtagtgtgaa cttgtggggc agggcaccc tggtcaccgt ctc            353
```

<210> SEQ ID NO 97
<211> LENGTH: 332
<212> TYPE: DNA
<213> ORGANISM: Oryctolagus cuniculus

<400> SEQUENCE: 97

```
cgtgatgacc cagactccat cttccaagtc tgtccctgtg ggaggcacag tcaccatcaa      60
ttgccaggcc agtgagagtg tttatattaa caaccgctta tcctggtttc agcagaaacc     120
agggcaacct cccaagctcc tgatctatta tgcatccact ctggcatctg gggtcccatc     180
gcggttcaaa ggcagtggat ctgggacaca gttcactctc accatcagcg gcgtgcagtg     240
tgacgatgct gccacttact actgtgcagg atggaggggt gctactactg atggtattga     300
tttcggcgga gggaccgagg tggtggtcaa ag                                   332
```

<210> SEQ ID NO 98
<211> LENGTH: 114
<212> TYPE: PRT
<213> ORGANISM: Oryctolagus cuniculus

<400> SEQUENCE: 98

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Arg Tyr Tyr
            20                  25                  30

Met Thr Trp Val Arg Gln Ala Pro Gly Lys Gly Leu Glu Tyr Ile Gly
        35                  40                  45

Val Ile Ile Pro Gly Gly Thr Thr Tyr Tyr Ala Ser Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Gly Gly Pro
                85                  90                  95

Thr Gly Asn Ser His Phe Thr Leu Trp Gly Gln Gly Thr Leu Val Thr
```

```
              100              105              110

Val Ser

<210> SEQ ID NO 99
<211> LENGTH: 110
<212> TYPE: PRT
<213> ORGANISM: Oryctolagus cuniculus

<400> SEQUENCE: 99

Val Met Thr Gln Thr Pro Ser Ser Lys Ser Val Pro Val Gly Gly Thr
1               5                   10                  15

Val Thr Ile Asn Cys Gln Ala Ser Glu Ser Val Tyr Asn Asn Asn His
            20                  25                  30

Leu Ser Trp Tyr Gln Gln Lys Ser Gly Gln Pro Pro Lys Leu Leu Ile
        35                  40                  45

Tyr Glu Ala Ser Lys Leu Glu Ser Gly Val Pro Pro Arg Phe Lys Gly
    50                  55                  60

Ser Gly Ser Gly Thr Gln Phe Thr Leu Thr Ile Ser Asp Val Val Cys
65                  70                  75                  80

Asp Asp Ala Ala Thr Tyr Tyr Cys Ser Gly Tyr Lys Arg Val Thr Thr
                85                  90                  95

Asp Gly Ile Ala Phe Gly Gly Gly Thr Glu Val Val Val Lys
            100                 105                 110

<210> SEQ ID NO 100
<211> LENGTH: 118
<212> TYPE: PRT
<213> ORGANISM: Oryctolagus cuniculus

<400> SEQUENCE: 100

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Asn
            20                  25                  30

Tyr Val Met Cys Trp Val Arg Gln Ala Pro Gly Lys Gly Leu Glu Trp
        35                  40                  45

Val Ala Cys Ile Trp Phe Ala Gly Ile Val Asp Thr Thr Tyr Tyr Ala
    50                  55                  60

Thr Trp Ala Lys Gly Arg Phe Thr Ile Ser Lys Thr Ser Ser Thr Thr
65                  70                  75                  80

Val Thr Leu Gln Met Thr Ser Leu Thr Ala Ala Asp Thr Ala Thr Tyr
                85                  90                  95

Phe Cys Ala Arg Asn Pro Val Gly Ser Val Asn Leu Trp Gly Gln Gly
            100                 105                 110

Thr Leu Val Thr Val Ser
        115

<210> SEQ ID NO 101
<211> LENGTH: 110
<212> TYPE: PRT
<213> ORGANISM: Oryctolagus cuniculus

<400> SEQUENCE: 101

Val Met Thr Gln Thr Pro Ser Ser Lys Ser Val Pro Val Gly Gly Ser
1               5                   10                  15

Val Thr Ile Asn Cys Gln Ala Ser Glu Ser Val Tyr Ser Asn Asn Arg
            20                  25                  30
```

```
Leu Ser Trp Tyr Gln Gln Lys Pro Gly Gln Pro Pro Lys Leu Leu Ile
        35                  40                  45

Tyr Tyr Ala Ser Thr Leu Glu Ser Gly Val Pro Ser Arg Phe Lys Gly
        50                  55                  60

Ser Gly Phe Gly Thr His Phe Thr Leu Thr Ile Ser Gly Ala Gln Cys
65                  70                  75                  80

Asp Asp Ala Ala Thr Tyr Tyr Cys Ala Gly Trp Arg Gly Ala Arg Thr
                85                  90                  95

Asp Gly Val Asp Phe Gly Gly Gly Thr Glu Val Val Val Lys
            100                 105                 110

<210> SEQ ID NO 102
<211> LENGTH: 120
<212> TYPE: PRT
<213> ORGANISM: Oryctolagus cuniculus

<400> SEQUENCE: 102

Gln Glu Gln Leu Val Glu Ser Gly Gly Gly Leu Val Gln Pro Gly Ala
1               5                   10                  15

Ser Leu Thr Leu Thr Cys Thr Ala Ser Gly Phe Ser Phe Ser Ser Ser
            20                  25                  30

Tyr Val Met Cys Trp Val Arg Gln Ala Pro Gly Lys Gly Leu Glu Trp
        35                  40                  45

Ile Thr Cys Ser Asp Thr Gly Ile Asn Thr Trp Tyr Ala Ser Trp Ala
        50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Arg Tyr Thr Gly Asp Thr Tyr Leu Gly Asn Phe Asn Leu Trp Gly
            100                 105                 110

Gln Gly Thr Leu Val Thr Val Ser
            115                 120

<210> SEQ ID NO 103
<211> LENGTH: 109
<212> TYPE: PRT
<213> ORGANISM: Oryctolagus cuniculus

<400> SEQUENCE: 103

Ala Gln Val Leu Thr Gln Thr Pro Ala Ser Val Ser Ala Ala Val Gly
1               5                   10                  15

Gly Thr Val Thr Ile Asn Cys Gln Ala Ser Gln Ser Val Tyr Lys Asn
            20                  25                  30

Asn Tyr Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Trp Arg Ser
                85                  90                  95

Leu Asn Ala Phe Gly Gly Gly Thr Glu Val Val Val Lys
            100                 105

<210> SEQ ID NO 104
<211> LENGTH: 120
```

<212> TYPE: PRT
<213> ORGANISM: Oryctolagus cuniculus

<400> SEQUENCE: 104

Gln Glu Gln Leu Glu Glu Ser Gly Gly Asp Leu Val Lys Pro Gly Ala
1               5                   10                  15

Ser Leu Thr Leu Thr Cys Thr Ala Ser Glu Phe Ser Phe Ser Ser Arg
            20                  25                  30

Tyr Trp Ala Cys Trp Val Arg Gln Ala Pro Gly Lys Gly Leu Glu Trp
        35                  40                  45

Ser Ala Cys Ile Tyr Thr Gly Ser Ile Asp Ala Thr Tyr Tyr Ala Ser
    50                  55                  60

Trp Ala Lys Gly Arg Phe Thr Ile Ser Lys Thr Ser Ser Thr Thr Val
65                  70                  75                  80

Thr Leu Gln Val Thr Ser Leu Thr Ala Ala Asp Thr Ala Thr Tyr Phe
                85                  90                  95

Cys Val Arg Gly Ser Asp Ala Trp Gly Leu Tyr Phe Asn Leu Trp Gly
            100                 105                 110

Gln Gly Thr Leu Val Thr Val Ser
        115                 120

<210> SEQ ID NO 105
<211> LENGTH: 107
<212> TYPE: PRT
<213> ORGANISM: Oryctolagus cuniculus

<400> SEQUENCE: 105

Leu Thr Gln Thr Pro Ser Ser Val Ser Ala Ala Val Gly Gly Thr Val
1               5                   10                  15

Thr Val Ser Cys Gln Ser Ser Gln Ser Ile His Lys Asn Asn Tyr Leu
            20                  25                  30

Ala Trp Tyr Gln Gln Lys Pro Gly Gln Pro Pro Lys Leu Leu Ile Tyr
        35                  40                  45

Phe Ala Ser Thr Leu Ala Ser Gly Val Pro Ser Arg Phe Lys Gly Ser
    50                  55                  60

Gly Ser Gly Thr Gln Phe Thr Leu Thr Ile Ser Asp Leu Glu Cys Asp
65                  70                  75                  80

Asp Ala Ala Thr Tyr Tyr Cys Ala Gly Val Tyr Ser Gly Arg Ile Phe
                85                  90                  95

Ala Phe Gly Gly Gly Thr Glu Val Val Val Lys
            100                 105

<210> SEQ ID NO 106
<211> LENGTH: 108
<212> TYPE: PRT
<213> ORGANISM: Oryctolagus cuniculus

<400> SEQUENCE: 106

Gln Ser Val Glu Glu Ser Gly Gly Arg Leu Val Thr Pro Gly Thr Pro
1               5                   10                  15

Leu Thr Leu Thr Cys Lys Val Ser Gly Phe Ser Leu Ser Ser Tyr Thr
            20                  25                  30

Met Ile Trp Val Arg Gln Ala Pro Gly Lys Gly Leu Glu Trp Ile Gly
        35                  40                  45

Tyr Ile Tyr Gly Gly Ile Gly Ser Thr Trp Tyr Ala Ser Trp Ala Lys
    50                  55                  60

Gly Arg Phe Thr Ile Ser Lys Thr Ser Thr Thr Val Asp Leu Lys Ile

-continued

```
65                  70                  75                  80

Thr Ser Pro Thr Thr Glu Asp Thr Ala Thr Tyr Phe Cys Gly Arg Gly
                85                  90                  95

Asp Ile Trp Gly Gln Gly Thr Leu Val Thr Val Ser
            100                 105

<210> SEQ ID NO 107
<211> LENGTH: 110
<212> TYPE: PRT
<213> ORGANISM: Oryctolagus cuniculus

<400> SEQUENCE: 107

Val Leu Thr Gln Thr Ala Ser Pro Val Ser Ala Ala Val Gly Gly Thr
1               5                   10                  15

Val Thr Ile Asn Cys Gln Ser Ser Gln Ser Val Tyr Lys Asn Arg Leu
                20                  25                  30

Ser Trp Tyr Gln Gln Lys Pro Gly Gln Ser Pro Lys Arg Leu Ile Tyr
            35                  40                  45

Gly Ala Ser Thr Leu Glu Ser Gly Val Pro Ser Arg Phe Lys Gly Ser
        50                  55                  60

Gly Ser Gly Thr Gln Phe Thr Leu Thr Ile Ser Asp Val Gln Cys Asp
65                  70                  75                  80

Asp Ala Ala Thr Tyr Tyr Cys Leu Gly Asn Tyr Asp Cys Ser Ser Val
                85                  90                  95

Asp Cys Gly Ala Phe Gly Gly Gly Thr Glu Val Val Val Lys
            100                 105                 110

<210> SEQ ID NO 108
<211> LENGTH: 114
<212> TYPE: PRT
<213> ORGANISM: Oryctolagus cuniculus

<400> SEQUENCE: 108

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Phe Ser Ala Tyr Tyr
                20                  25                  30

Met Thr Trp Val Arg Gln Ala Pro Gly Lys Gly Leu Glu Phe Ile Gly
            35                  40                  45

Val Thr Ile Pro Ile Gly Arg Thr Tyr Tyr Ala Ser Trp Ala Lys Gly
        50                  55                  60

Arg Phe Thr Ile Ser Lys Thr Ser Thr Thr Val His Leu Lys Ile Thr
65                  70                  75                  80

Ser Pro Thr Thr Glu Asp Thr Ala Ala Tyr Phe Cys Ala Gly Gly Pro
                85                  90                  95

Thr Gly Asn Ser His Phe Thr Leu Trp Gly Gln Gly Thr Leu Val Thr
            100                 105                 110

Val Ser

<210> SEQ ID NO 109
<211> LENGTH: 110
<212> TYPE: PRT
<213> ORGANISM: Oryctolagus cuniculus

<400> SEQUENCE: 109

Val Met Thr Gln Thr Pro Ser Ser Lys Ser Val Pro Val Gly Asp Thr
1               5                   10                  15
```

```
Val Thr Ile Asn Cys Gln Ala Ser Glu Ser Val Tyr Asn Asn Asn Gln
            20              25              30

Leu Ser Trp Tyr Gln Gln Lys Pro Gly Gln Pro Pro Lys Leu Leu Ile
        35              40              45

Tyr Gln Ala Ser Lys Leu Glu Ser Gly Val Pro Ser Arg Phe Lys Gly
    50              55              60

Ser Gly Ser Gly Thr Gln Phe Thr Leu Thr Ile Ser Asp Val Val Cys
65              70              75              80

Asp Asp Ala Ala Thr Tyr Tyr Cys Ala Gly Tyr Lys Ser Pro Thr Thr
                85              90              95

Asp Gly Ile Ala Phe Gly Gly Gly Thr Glu Val Val Val Lys
            100             105             110

<210> SEQ ID NO 110
<211> LENGTH: 112
<212> TYPE: PRT
<213> ORGANISM: Oryctolagus cuniculus

<400> SEQUENCE: 110

Gln Ser Val Glu Glu Ser Gly Gly Arg Leu Val Thr Pro Gly Thr Pro
1               5               10              15

Leu Thr Leu Thr Cys Thr Val Ser Gly Phe Ser Leu Ser Ser Tyr Ala
            20              25              30

Met Ser Trp Val Arg Gln Ala Pro Gly Lys Gly Leu Glu Trp Ile Gly
        35              40              45

Phe Ile Tyr Asn Tyr Glu Thr Tyr Tyr Ala Asn Trp Ala Lys Gly Arg
    50              55              60

Phe Thr Ile Ser Lys Thr Ser Thr Ser Val Val Leu Lys Ile Thr Ser
65              70              75              80

Pro Thr Thr Asp Asp Thr Ala Thr Tyr Phe Cys Ala Arg Asp Ile Phe
                85              90              95

Arg Thr Asn Thr Asn Leu Trp Gly Gln Gly Thr Leu Val Thr Val Ser
            100             105             110

<210> SEQ ID NO 111
<211> LENGTH: 111
<212> TYPE: PRT
<213> ORGANISM: Oryctolagus cuniculus

<400> SEQUENCE: 111

Val Leu Thr Gln Thr Ala Ser Pro Val Ser Ala Val Val Gly Ser Thr
1               5               10              15

Val Thr Ile Asn Cys Gln Ala Ser Gln Ser Val Tyr Lys Asn Asn Gly
            20              25              30

Leu Ser Trp Tyr Gln Gln Lys Pro Gly Gln Pro Pro Lys Gly Leu Ile
        35              40              45

Ser Phe Thr Ser Thr Leu Ala Ser Gly Val Ser Ser Arg Phe Lys Gly
    50              55              60

Ser Gly Ser Gly Thr Gln Phe Thr Leu Thr Ile Ser Asp Val Gln Cys
65              70              75              80

Asp Asp Ala Ala Thr Tyr Tyr Cys Leu Gly Gly Tyr Asp Cys Ser Ser
                85              90              95

Arg Val Cys Gly Ala Phe Gly Gly Gly Thr Glu Val Val Val Lys
            100             105             110

<210> SEQ ID NO 112
<211> LENGTH: 114
```

<212> TYPE: PRT
<213> ORGANISM: Oryctolagus cuniculus

<400> SEQUENCE: 112

Gln Ser Val Glu Glu Ser Gly Gly Arg Leu Val Thr Pro Gly Thr Pro
1               5                   10                  15

Leu Thr Leu Thr Cys Thr Val Ser Gly Phe Thr Phe Ser Ala Tyr Tyr
            20                  25                  30

Met Ser Trp Val Arg Gln Ala Pro Gly Lys Gly Leu Glu Tyr Ile Gly
        35                  40                  45

Val Thr Ile Pro Arg Gly Ile Thr Tyr Tyr Ala Asn Trp Ala Lys Gly
    50                  55                  60

Arg Phe Thr Ile Ser Lys Thr Ser Thr Thr Val Asp Leu Arg Ile Thr
65                  70                  75                  80

Ser Pro Thr Thr Glu Asp Thr Ala Thr Tyr Phe Cys Ala Gly Gly Pro
                85                  90                  95

Thr Gly Asn Ser His Phe Thr Leu Trp Gly Gln Gly Thr Leu Val Thr
            100                 105                 110

Val Ser

<210> SEQ ID NO 113
<211> LENGTH: 110
<212> TYPE: PRT
<213> ORGANISM: Oryctolagus cuniculus

<400> SEQUENCE: 113

Val Met Thr Gln Thr Pro Ser Ser Lys Ser Val Pro Val Gly Asp Thr
1               5                   10                  15

Val Thr Ile Asn Cys Gln Ala Ser Glu Ser Val Tyr Ala Asn Asn Gln
            20                  25                  30

Leu Ser Trp Tyr Gln Gln Lys Gln Gly Gln Pro Pro Lys Leu Leu Ile
        35                  40                  45

Tyr Gln Ala Ser Lys Leu Glu Ser Gly Val Pro Ser Arg Phe Ser Gly
    50                  55                  60

Ser Gly Ser Gly Thr Gln Phe Ala Leu Thr Ile Thr Asp Val Gln Cys
65                  70                  75                  80

Asp Asp Ala Ala Thr Tyr Tyr Cys Ser Gly Tyr Val Arg Thr Thr Thr
                85                  90                  95

Asp Gly Ile Ala Phe Gly Gly Gly Thr Glu Val Val Val Lys
            100                 105                 110

<210> SEQ ID NO 114
<211> LENGTH: 114
<212> TYPE: PRT
<213> ORGANISM: Oryctolagus cuniculus

<400> SEQUENCE: 114

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ile Arg Tyr Tyr
            20                  25                  30

Val Thr Trp Val Arg Gln Ala Pro Gly Lys Gly Leu Glu Tyr Ile Gly
        35                  40                  45

Val Thr Ile Pro Arg Gly Ile Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

-continued

Ser Pro Thr Thr Glu Asp Thr Ala Thr Tyr Phe Cys Ala Gly Gly Pro
                85                  90                  95

Thr Gly Asn Ser His Phe Thr Leu Trp Gly Gln Gly Thr Leu Val Thr
            100                 105                 110

Val Ser

<210> SEQ ID NO 115
<211> LENGTH: 110
<212> TYPE: PRT
<213> ORGANISM: Oryctolagus cuniculus

<400> SEQUENCE: 115

Val Met Thr Gln Thr Pro Ser Ser Lys Ser Val Pro Val Gly Asp Thr
1               5                   10                  15

Val Thr Ile Asn Cys Gln Ala Ser Glu Ser Val Tyr Asn Asn Asn Gln
                20                  25                  30

Leu Ser Trp Tyr Gln Gln Lys Pro Gly Gln Pro Pro Lys Leu Leu Ile
            35                  40                  45

Tyr Gln Ala Ser Lys Leu Glu Ser Gly Val Pro Ser His Phe Ser Gly
        50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ser Gly Tyr Lys Ser Thr Thr Thr
                85                  90                  95

Asp Gly Ile Ala Phe Gly Gly Gly Thr Glu Val Val Val Lys
            100                 105                 110

<210> SEQ ID NO 116
<211> LENGTH: 117
<212> TYPE: PRT
<213> ORGANISM: Oryctolagus cuniculus

<400> SEQUENCE: 116

Gln Glu Gln Leu Glu Glu Ser Gly Gly Asp Leu Val Lys Pro Gly Ala
1               5                   10                  15

Ser Leu Thr Leu Thr Cys Lys Ala Ser Gly Phe Ser Phe Ser Ser Ser
            20                  25                  30

Tyr Val Met Cys Trp Val Arg Gln Ala Pro Gly Lys Gly Leu Glu Trp
        35                  40                  45

Ile Ala Cys Ile Tyr Phe Ala Gly Ile Asp Thr Ile Tyr Tyr Ala Ser
        50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asn Pro Ile Gly Ser Val Asn Leu Trp Gly Gln Gly Thr
            100                 105                 110

Leu Val Thr Val Ser
        115

<210> SEQ ID NO 117
<211> LENGTH: 110
<212> TYPE: PRT
<213> ORGANISM: Oryctolagus cuniculus

<400> SEQUENCE: 117

Val Met Thr Gln Thr Pro Ser Ser Lys Ser Val Pro Val Gly Gly Thr

-continued

```
1               5                   10                  15

Val Thr Ile Asn Cys Gln Ala Ser Gln Ser Val Tyr Ser Asn Asn Arg
            20                  25                  30

Leu Ser Trp Phe Gln Gln Lys Pro Gly Gln Pro Pro Lys Leu Leu Ile
        35                  40                  45

Tyr Tyr Leu Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Trp Arg Gly Ala Thr Thr
                85                  90                  95

Asp Gly Val Asp Phe Gly Gly Gly Thr Glu Val Val Val Lys
            100                 105                 110
```

<210> SEQ ID NO 118
<211> LENGTH: 118
<212> TYPE: PRT
<213> ORGANISM: Oryctolagus cuniculus

<400> SEQUENCE: 118

```
Gln Glu Gln Leu Glu Glu Ser Gly Gly Asp Leu Val Thr Pro Gly Gly
1               5                   10                  15

Thr Leu Thr Leu Thr Cys Lys Ala Ser Gly Phe Ser Phe Asn Ser Asn
            20                  25                  30

Tyr Val Met Cys Trp Val Arg Gln Ala Pro Gly Lys Gly Leu Glu Trp
        35                  40                  45

Ile Ala Cys Ile Trp Phe Ala Gly Ser Gly Asp Val Ile Tyr Tyr Ala
    50                  55                  60

Ser Trp Ala Lys Gly Arg Phe Thr Ile Ser Lys Thr Ser Ser Thr Thr
65                  70                  75                  80

Val Thr Leu Gln Met Thr Ser Leu Thr Ala Ala Asp Thr Ala Thr His
                85                  90                  95

Phe Cys Ala Arg Asn Pro Val Gly Ser Val Asn Leu Trp Gly Gln Gly
            100                 105                 110

Thr Leu Val Thr Val Ser
        115
```

<210> SEQ ID NO 119
<211> LENGTH: 110
<212> TYPE: PRT
<213> ORGANISM: Oryctolagus cuniculus

<400> SEQUENCE: 119

```
Val Met Thr Gln Thr Pro Ser Ser Lys Ser Val Pro Val Gly Gly Thr
1               5                   10                  15

Val Thr Ile Asn Cys Gln Ala Ser Glu Ser Val Tyr Ile Asn Asn Arg
            20                  25                  30

Leu Ser Trp Phe Gln Gln Lys Pro Gly Gln Pro Pro Lys Leu Leu Ile
        35                  40                  45

Tyr Tyr Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Gln Cys
65                  70                  75                  80

Asp Asp Ala Ala Thr Tyr Tyr Cys Ala Gly Trp Arg Gly Ala Thr Thr
                85                  90                  95

Asp Gly Ile Asp Phe Gly Gly Gly Thr Glu Val Val Val Lys
```

```
              100                105                110
```

```
<210> SEQ ID NO 120
<211> LENGTH: 8
<212> TYPE: PRT
<213> ORGANISM: Oryctolagus cuniculus

<400> SEQUENCE: 120

Gly Phe Ser Leu Ser Ser Tyr Asn
1               5

<210> SEQ ID NO 121
<211> LENGTH: 7
<212> TYPE: PRT
<213> ORGANISM: Oryctolagus cuniculus

<400> SEQUENCE: 121

Ile Gly Thr Gly Gly Ile Thr
1               5

<210> SEQ ID NO 122
<211> LENGTH: 12
<212> TYPE: PRT
<213> ORGANISM: Oryctolagus cuniculus

<400> SEQUENCE: 122

Val Arg Ser Ser Gly Ser Asp Trp Trp Phe His Ile
1               5                   10

<210> SEQ ID NO 123
<211> LENGTH: 8
<212> TYPE: PRT
<213> ORGANISM: Oryctolagus cuniculus

<400> SEQUENCE: 123

Gln Ser Val Tyr Asn Asn Asn Asn
1               5

<210> SEQ ID NO 124
<211> LENGTH: 3
<212> TYPE: PRT
<213> ORGANISM: Oryctolagus cuniculus

<400> SEQUENCE: 124

Arg Ala Ser
1

<210> SEQ ID NO 125
<211> LENGTH: 10
<212> TYPE: PRT
<213> ORGANISM: Oryctolagus cuniculus

<400> SEQUENCE: 125

Gln Gly Tyr Phe Ser Gly Phe Ile Thr Thr
1               5                   10

<210> SEQ ID NO 126
<211> LENGTH: 341
<212> TYPE: DNA
<213> ORGANISM: Oryctolagus cuniculus

<400> SEQUENCE: 126
cagtcgctgg aggagtccgg gggtcgcctg gtcacgcctg ggacacccct gacactcacc      60
tgcacagtct ctggattctc cctcagtagc tacaacatgg gctgggtccg ccaggctcca     120
```

```
ggggaggggc tggagtggat cggagtcatt ggtactggtg gtatcacaca ctacgcgacc      180
tgggcaaaag gccgagtcgc catctccaga acctcgacca cggtgggtct gcgaatgacc      240
agtccgacaa ccgaggacac ggccacctat ttctgtgtca gatctagtgg tagtgattgg      300
tggtttcaca tctggggcca gggcaccctg gtcaccgtct c                          341
```

<210> SEQ ID NO 127
<211> LENGTH: 325
<212> TYPE: DNA
<213> ORGANISM: Oryctolagus cuniculus

<400> SEQUENCE: 127

```
gtgctgaccc agactacatc gcccgtgtct gcagctgtgg gaggcacagt caccatcagt       60
tgccagtcca gtcagagtgt ttataataac aacaacttag cctggtttca gcagaaacca      120
gggcagcctc ccaagctcct gatctacagg gcatccaatc tgccatctgg tgtcccatcg      180
cggttcagag gcagtggatc tgggtcacag ttcactctca caatcagcga agtacagtgt      240
gacgatgctg ccacttacta ctgtcaaggc tattttagtg gatttatcac tactttcggc      300
ggagggaccg aggtggtggt caaag                                           325
```

<210> SEQ ID NO 128
<211> LENGTH: 114
<212> TYPE: PRT
<213> ORGANISM: Oryctolagus cuniculus

<400> SEQUENCE: 128

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asn
            20                  25                  30

Met Gly Trp Val Arg Gln Ala Pro Gly Glu Gly Leu Glu Trp Ile Gly
        35                  40                  45

Val Ile Gly Thr Gly Gly Ile Thr His Tyr Ala Thr Trp Ala Lys Gly
    50                  55                  60

Arg Val Ala Ile Ser Arg Thr Ser Thr Thr Val Gly Leu Arg Met Thr
65                  70                  75                  80

Ser Pro Thr Thr Glu Asp Thr Ala Thr Tyr Phe Cys Val Arg Ser Ser
                85                  90                  95

Gly Ser Asp Trp Trp Phe His Ile Trp Gly Gln Gly Thr Leu Val Thr
            100                 105                 110

Val Ser
```

<210> SEQ ID NO 129
<211> LENGTH: 108
<212> TYPE: PRT
<213> ORGANISM: Oryctolagus cuniculus

<400> SEQUENCE: 129

```
Val Leu Thr Gln Thr Thr Ser Pro Val Ser Ala Ala Val Gly Gly Thr
1               5                   10                  15

Val Thr Ile Ser Cys Gln Ser Ser Gln Ser Val Tyr Asn Asn Asn Asn
            20                  25                  30

Leu Ala Trp Phe Gln Gln Lys Pro Gly Gln Pro Pro Lys Leu Leu Ile
        35                  40                  45

Tyr Arg Ala Ser Asn Leu Pro Ser Gly Val Pro Ser Arg Phe Arg Gly
    50                  55                  60
```

Ser Gly Ser Gly Ser Gln Phe Thr Leu Thr Ile Ser Glu Val Gln Cys
65                  70                  75                  80

Asp Asp Ala Ala Thr Tyr Tyr Cys Gln Gly Tyr Phe Ser Gly Phe Ile
                    85                  90                  95

Thr Thr Phe Gly Gly Gly Thr Glu Val Val Val Lys
            100                 105

<210> SEQ ID NO 130
<211> LENGTH: 8
<212> TYPE: PRT
<213> ORGANISM: Mus musculus

<400> SEQUENCE: 130

Gly Phe Thr Phe Ser Ser Tyr Tyr
1               5

<210> SEQ ID NO 131
<211> LENGTH: 8
<212> TYPE: PRT
<213> ORGANISM: Mus Musculus

<400> SEQUENCE: 131

Ile Asn Ser Asn Gly Gly Ser Thr
1               5

<210> SEQ ID NO 132
<211> LENGTH: 9
<212> TYPE: PRT
<213> ORGANISM: Mus Musculus

<400> SEQUENCE: 132

Val Arg Gln Asn Tyr Glu Gly Ala Tyr
1               5

<210> SEQ ID NO 133
<211> LENGTH: 11
<212> TYPE: PRT
<213> ORGANISM: Mus Musculus

<400> SEQUENCE: 133

Gln Ser Ile Val His Ser Asn Gly Asn Thr Tyr
1               5                   10

<210> SEQ ID NO 134
<211> LENGTH: 3
<212> TYPE: PRT
<213> ORGANISM: Mus Musculus

<400> SEQUENCE: 134

Lys Val Ser
1

<210> SEQ ID NO 135
<211> LENGTH: 9
<212> TYPE: PRT
<213> ORGANISM: Mus Musculus

<400> SEQUENCE: 135

Phe Gln Ser Ser His Val Pro Trp Thr
1               5

<210> SEQ ID NO 136
<211> LENGTH: 348

<212> TYPE: DNA
<213> ORGANISM: Mus Musculus

<400> SEQUENCE: 136
gacgtgaagc tcgtggagtc tgggggaggc ttagtgaagc ttggagggtc cctgaaactc      60
tcctgtgcag cctctggatt cactttcagt agctattaca tgtcttgggt tcgccagact     120
ccagagaaga ggctggagtt ggtcgcaacc attaatagta atggtggtag cacctactat     180
ccagacactg tgaagggccg aatcaccatc tccagagaca atgccaagaa caccctgcag     240
ttgcaaatga gcagtctgag gtctgaggac acagccttgt attactgtgt aagacaaaac     300 tacgagggg cttactgggg ccaagggact ctggtcactg tctctgca                  348

<210> SEQ ID NO 137
<211> LENGTH: 336
<212> TYPE: DNA
<213> ORGANISM: Mus Musculus

<400> SEQUENCE: 137
gatgttttga tgacccaaac tccactctcc ctgcctgtca ctcttggaga tcaagcctcc      60
atctcttgca gatctagtca gagcattgta catagtaatg aaacaccta tttagaatgg      120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaagttc acatgttccg     300
tggacgttcg gtggaggcac caagctggaa atcaaa                              336

<210> SEQ ID NO 138
<211> LENGTH: 116
<212> TYPE: PRT
<213> ORGANISM: Mus Musculus

<400> SEQUENCE: 138

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Thr Ile Asn Ser Asn Gly Gly Ser Thr Tyr Tyr Pro Asp Thr Val
    50                  55                  60

Lys Gly Arg Ile Thr Ile Ser Arg Asp Asn Ala Lys Asn Thr Leu Gln
65                  70                  75                  80

Leu Gln Met Ser Ser Leu Arg Ser Glu Asp Thr Ala Leu Tyr Tyr Cys
                85                  90                  95

Val Arg Gln Asn Tyr Glu Gly Ala Tyr Trp Gly Gln Gly Thr Leu Val
            100                 105                 110

Thr Val Ser Ala
        115

<210> SEQ ID NO 139
<211> LENGTH: 112
<212> TYPE: PRT
<213> ORGANISM: Mus Musculus

<400> SEQUENCE: 139

Asp Val Leu Met Thr Gln Thr Pro Leu Ser Leu Pro Val Thr Leu Gly
1               5                   10                  15

```
Asp Gln Ala Ser Ile Ser Cys Arg Ser Ser Gln Ser Ile Val His Ser
        20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Ser His Val Pro Trp Thr Phe Gly Gly Gly Thr Lys Leu Glu Ile Lys
            100                 105                 110

<210> SEQ ID NO 140
<211> LENGTH: 8
<212> TYPE: PRT
<213> ORGANISM: Mus Musculus

<400> SEQUENCE: 140

Gly Phe Thr Phe Ser Ser Tyr Tyr
1               5

<210> SEQ ID NO 141
<211> LENGTH: 8
<212> TYPE: PRT
<213> ORGANISM: Mus Musculus

<400> SEQUENCE: 141

Ile Asn Thr Asn Gly Gly Ser Thr
1               5

<210> SEQ ID NO 142
<211> LENGTH: 9
<212> TYPE: PRT
<213> ORGANISM: Mus Musculus

<400> SEQUENCE: 142

Val Arg Gln Asn Tyr Glu Gly Ala Tyr
1               5

<210> SEQ ID NO 143
<211> LENGTH: 11
<212> TYPE: PRT
<213> ORGANISM: Mus Musculus

<400> SEQUENCE: 143

Gln Ser Ile Val His Ser Asn Gly Asn Thr Tyr
1               5                   10

<210> SEQ ID NO 144
<211> LENGTH: 3
<212> TYPE: PRT
<213> ORGANISM: Mus Musculus

<400> SEQUENCE: 144

Lys Val Ser
1

<210> SEQ ID NO 145
<211> LENGTH: 9
<212> TYPE: PRT
<213> ORGANISM: Mus Musculus
```

<400> SEQUENCE: 145

Phe Gln Ser Ser His Val Pro Trp Thr
1               5

<210> SEQ ID NO 146
<211> LENGTH: 348
<212> TYPE: DNA
<213> ORGANISM: Mus Musculus

<400> SEQUENCE: 146
gacgtgaagc tcgtggagtc tgggggagac ttagtgaagc ttggagggtc cctgaaactc      60
tcctgtgcag cctctggatt cactttcagt agctattaca tgtcttgggt tcgccagact     120
ccagagaaga ggctggagtt ggtcgcagtc attaatacta atggtggtag cacctactat     180
ccagacactg tgaagggccg attcaccatc tccagagaca atgccaagaa caccctgtac     240
ctgcaaatga gcagtctgaa gtctgaggac acagccttgt attactgtgt aagacaaaac     300 tacgagggg cttactgggg ccaagggact ctggtcactg tctctgca                   348

<210> SEQ ID NO 147
<211> LENGTH: 336
<212> TYPE: DNA
<213> ORGANISM: Mus Musculus

<400> SEQUENCE: 147
gatgttttga tgacccaaac tccactctcc ctgcctgtca gtcttggaga tcaagcctcc      60
atctcttgca gatctagtca gagcattgta catagtaatg aaacaccta tttagaatgg      120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaagttc acatgttccg     300
tggacgttcg gtggaggcac caagctggaa atcaaa                               336

<210> SEQ ID NO 148
<211> LENGTH: 116
<212> TYPE: PRT
<213> ORGANISM: Mus Musculus

<400> SEQUENCE: 148

Asp Val Lys Leu Val Glu Ser Gly Gly Asp Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Val Ile Asn Thr Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Val Arg Gln Asn Tyr Glu Gly Ala Tyr Trp Gly Gln Gly Thr Leu Val
            100                 105                 110

Thr Val Ser Ala
        115

-continued

```
<210> SEQ ID NO 149
<211> LENGTH: 112
<212> TYPE: PRT
<213> ORGANISM: Mus Musculus

<400> SEQUENCE: 149

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Ser His Val Pro Trp Thr Phe Gly Gly Gly Thr Lys Leu Glu Ile Lys
                100                 105                 110
```